US012788812B2

(12) United States Patent
Brownstein et al.

(10) Patent No.: US 12,788,812 B2
(45) **Date of Patent: *Nov. 10, 2026**

(54) DOSING STRATEGY THAT MITIGATES CYTOKINE RELEASE SYNDROME FOR THERAPEUTIC ANTIBODIES

(71) Applicant: Regeneron Pharmaceuticals, Inc., Tarrytown, NY (US)

(72) Inventors: Carrie Brownstein, New York, NY (US); Israel Lowy, Dobbs Ferry, NY (US); Lieve Lucille Adriaens, Westfield, NJ (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 725 days.

This patent is subject to a terminal disclaimer.

(21) Appl. No.: 18/101,310

(22) Filed: Jan. 25, 2023

(65) Prior Publication Data

US 2023/0165959 A1 Jun. 1, 2023

Related U.S. Application Data

(63) Continuation of application No. 16/556,885, filed on Aug. 30, 2019, now Pat. No. 11,590,223.

(60) Provisional application No. 62/861,100, filed on Jun. 13, 2019, provisional application No. 62/774,019, filed on Nov. 30, 2018, provisional application No. 62/726,137, filed on Aug. 31, 2018.

(51) Int. Cl.

| | |
|---|---|
| ***A61K 39/395*** | (2006.01) |
| ***A61K 31/405*** | (2006.01) |
| ***A61K 31/573*** | (2006.01) |
| ***A61K 39/00*** | (2006.01) |
| ***A61K 45/06*** | (2006.01) |
| ***A61P 35/00*** | (2006.01) |
| ***A61P 35/02*** | (2006.01) |
| ***C07K 16/24*** | (2006.01) |
| ***C07K 16/28*** | (2006.01) |

(52) U.S. Cl.

CPC ........ *A61K 39/3955* (2013.01); *A61K 31/405* (2013.01); *A61K 31/573* (2013.01); *A61K 39/0011* (2013.01); *A61K 45/06* (2013.01); *A61P 35/00* (2018.01); *A61P 35/02* (2018.01); *C07K 16/248* (2013.01); *C07K 16/2809* (2013.01); *C07K 16/2818* (2013.01); *C07K 16/2866* (2013.01); *C07K 16/2887* (2013.01); *C07K 16/2896* (2013.01); *A61K 2039/507* (2013.01); *A61K 2039/5156* (2013.01); *A61K 2039/5158* (2013.01); *A61K 2039/545* (2013.01); *C07K 2317/31* (2013.01)

(58) Field of Classification Search

CPC ............ A61K 39/3955; C07K 16/2803; C07K 16/2887

See application file for complete search history.

(56) References Cited

U.S. PATENT DOCUMENTS

| | | | |
|---|---|---|---|
| 5,500,362 | A | 3/1996 | Robinson et al. |
| 5,624,821 | A | 4/1997 | Winter et al. |
| 5,648,260 | A | 7/1997 | Winter et al. |
| 5,658,570 | A | 8/1997 | Newman et al. |
| 5,677,180 | A | 10/1997 | Robinson et al. |
| 5,721,108 | A | 2/1998 | Robinson et al. |
| 5,736,137 | A | 4/1998 | Anderson et al. |
| 5,776,456 | A | 7/1998 | Anderson et al. |
| 5,843,439 | A | 12/1998 | Anderson et al. |
| 6,120,767 | A | 9/2000 | Robinson et al. |
| 6,180,377 | B1 | 1/2001 | Morgan et al. |
| 6,224,866 | B1 | 5/2001 | Barbera-Guillem |
| 6,399,061 | B1 | 6/2002 | Anderson et al. |
| 6,455,043 | B1 | 9/2002 | Grillo-Lopez |
| 6,528,624 | B1 | 3/2003 | Idusogie et al. |
| 6,551,592 | B2 | 4/2003 | Lindhofer et al. |
| 6,652,852 | B1 | 11/2003 | Robinson et al. |
| 6,682,734 | B1 | 1/2004 | Anderson et al. |
| 6,893,625 | B1 | 5/2005 | Robinson et al. |
| 7,151,164 | B2 | 12/2006 | Hansen et al. |
| 7,214,775 | B2 | 5/2007 | Hanai et al. |
| 7,396,917 | B2 | 7/2008 | Bowdish et al. |
| 7,563,441 | B2 | 7/2009 | Graus et al. |
| 7,597,889 | B1 | 10/2009 | Armour et al. |
| 7,608,260 | B2 | 10/2009 | Schenerman et al. |
| 7,700,097 | B2 | 4/2010 | Braslawsky et al. |

(Continued)

FOREIGN PATENT DOCUMENTS

| | | | |
|---|---|---|---|
| EP | 0327378 | B1 | 12/1996 |
| EP | 1400534 | A1 | 3/2004 |

(Continued)

OTHER PUBLICATIONS

"IgG-Fc Engineering for Therapeutic Use," InvivoGen Insight, 1 page, (2006). [Author Unknown] [Retrieved from the Internet Apr. 4, 2014: <URL: http://www.invivogen.comiclocs/Insight200605pdf>].
"IgG-Fe engineering for therapeutic use," Invivogen, 2 pages, (2007). [Author Unknown] [Retrieved from the Internet Jan. 12, 2011: <URL: http://www.invivogen.com/ressource.php?ID=22>].
Aklilu et al., "Depletion of normal B cells with rituximab as an adjunct to IL-2 therapy for renal cell carcinoma and melanoma," Annals of Oncology 15: 1109-1114; Chicago, IL (2004).

(Continued)

*Primary Examiner* — Xiaozhen Xie
(74) *Attorney, Agent, or Firm* — Schwabe, Williamson & Wyatt PC; Aparna Patankar

(57) ABSTRACT

Administration regimens for therapeutic proteins (e.g., T cell-activating bispecific antibodies) that mitigate cytokine release syndrome and infusion-related reaction are disclosed. The methods employ initial fractional dosing with optional administration of additional agents such as steroids or cytokine antagonists that are discontinued with maximal weekly dosing over the course of the dosing regimen.

60 Claims, 1 Drawing Sheet

Specification includes a Sequence Listing.

(56) References Cited

U.S. PATENT DOCUMENTS

| | | | |
|---|---|---|---|
| 7,700,099 | B2 | 4/2010 | Strohl |
| 7,728,114 | B2 | 6/2010 | Mach et al. |
| 7,820,166 | B2 | 10/2010 | Lanzavecchia et al. |
| 7,824,684 | B2 | 11/2010 | Graus |
| 7,867,491 | B2 | 1/2011 | Yang et al. |
| 7,879,984 | B2 | 2/2011 | Martin et al. |
| 7,960,512 | B2 | 6/2011 | Stavenhagen et al. |
| 8,075,884 | B2 | 12/2011 | Bowdish et al. |
| 8,076,459 | B2 | 12/2011 | Hofmeister et al. |
| 8,084,026 | B2 | 12/2011 | Glaser et al. |
| 8,097,713 | B2 | 1/2012 | Martin et al. |
| 8,153,583 | B2 | 4/2012 | Carton et al. |
| 8,236,314 | B2 | 8/2012 | Kai et al. |
| 8,268,972 | B2 | 9/2012 | Whitfield et al. |
| 8,329,181 | B2 | 12/2012 | Martin et al. |
| 8,383,109 | B2 | 2/2013 | Lazar et al. |
| 8,409,568 | B2 | 4/2013 | Gao et al. |
| 8,597,648 | B2 | 12/2013 | Guo et al. |
| 8,961,967 | B2 | 2/2015 | Strohl et al. |
| 9,359,437 | B2 | 6/2016 | Davis et al. |
| 9,657,102 | B2 | 5/2017 | Smith et al. |
| 10,106,610 | B2 | 10/2018 | Davis et al. |
| 10,179,819 | B2 | 1/2019 | Kirshner et al. |
| 10,421,804 | B2 | 9/2019 | Kyratsous et al. |
| 10,550,193 | B2 | 2/2020 | Smith et al. |
| 10,556,952 | B2 | 2/2020 | Davis et al. |
| 10,662,244 | B2 | 5/2020 | Smith et al. |
| 10,738,130 | B2 | 8/2020 | Haber et al. |
| 10,772,972 | B2 | 9/2020 | Rudge et al. |
| 10,941,208 | B2 | 3/2021 | Haber et al. |
| 10,988,537 | B2 | 4/2021 | Davis et al. |
| 11,072,656 | B2 | 7/2021 | Smith et al. |
| 11,117,955 | B2 | 9/2021 | Kyratsous et al. |
| 11,155,621 | B2 | 10/2021 | Smith et al. |
| 11,485,793 | B2 | 11/2022 | Haber et al. |
| 11,590,223 | B2 | 2/2023 | Brownstein et al. |
| 11,633,501 | B2 | 4/2023 | Rudge et al. |
| 11,952,430 | B2 | 4/2024 | Haber et al. |
| 12,054,557 | B2 | 8/2024 | Varghese et al. |
| 12,065,508 | B2 | 8/2024 | Haber et al. |
| 12,077,603 | B2 | 9/2024 | Haber et al. |
| 12,509,514 | B2 | 12/2025 | Davis et al. |
| 12,509,516 | B2 | 12/2025 | Davis et al. |
| 2003/0026804 | A1 | 2/2003 | Grillo-Lopez |
| 2004/0093621 | A1 | 5/2004 | Shitara |
| 2004/0167319 | A1 | 8/2004 | Teeling et al. |
| 2004/0171123 | A1 | 9/2004 | Rosen et al. |
| 2005/0025764 | A1 | 2/2005 | Watkins |
| 2005/0037000 | A1 | 2/2005 | Stavenhagen et al. |
| 2005/0053602 | A1 | 3/2005 | Brunetta |
| 2005/0191297 | A1 | 9/2005 | Brunetta |
| 2005/0226876 | A1 | 10/2005 | Graus et al. |
| 2005/0244403 | A1 | 11/2005 | Lazar et al. |
| 2005/0271658 | A1 | 12/2005 | Brunetta |
| 2006/0024295 | A1 | 2/2006 | Brunetta |
| 2006/0110387 | A1 | 5/2006 | Brunetta |
| 2006/0121032 | A1 | 6/2006 | Dahiyat et al. |
| 2006/0134709 | A1 | 6/2006 | Stavenhagen et al. |
| 2006/0193852 | A1 | 8/2006 | Dorken et al. |
| 2006/0233797 | A1 | 10/2006 | Gujrathi |
| 2006/0240007 | A1 | 10/2006 | Sanders |
| 2006/0263355 | A1 | 11/2006 | Quan et al. |
| 2007/0009523 | A1 | 1/2007 | Presta |
| 2007/0014720 | A1 | 1/2007 | Gazit-Bornstein et al. |
| 2007/0020259 | A1 | 1/2007 | Hansen et al. |
| 2007/0041972 | A1 | 2/2007 | Rother et al. |
| 2007/0081993 | A1 | 4/2007 | Kufer et al. |
| 2009/0022738 | A1 | 1/2009 | Hofmeister et al. |
| 2009/0035322 | A1 | 2/2009 | Martin et al. |
| 2009/0117133 | A1 | 5/2009 | Arnason et al. |
| 2009/0162901 | A1 | 6/2009 | Chen et al. |
| 2009/0252729 | A1 | 10/2009 | Farrington et al. |
| 2010/0105874 | A1 | 4/2010 | Schuurman et al. |
| 2010/0166749 | A1 | 7/2010 | Presta |
| 2010/0178298 | A1 | 7/2010 | Lindhofer |
| 2010/0183554 | A1 | 7/2010 | Mach et al. |
| 2010/0183615 | A1 | 7/2010 | Kufer et al. |
| 2010/0267934 | A1 | 10/2010 | Winkel et al. |
| 2010/0298542 | A1 | 11/2010 | Igawa et al. |
| 2010/0325744 | A1 | 12/2010 | Schuurman et al. |
| 2010/0331527 | A1 | 12/2010 | Davis et al. |
| 2011/0077383 | A1 | 3/2011 | Dall'Acqua et al. |
| 2011/0212087 | A1 | 9/2011 | Strohl et al. |
| 2011/0245473 | A1 | 10/2011 | Igawa et al. |
| 2011/0263830 | A1 | 10/2011 | Goetsch et al. |
| 2011/0293607 | A1 | 12/2011 | Labrijn et al. |
| 2012/0065379 | A1 | 3/2012 | Igawa et al. |
| 2012/0071634 | A1 | 3/2012 | Igawa et al. |
| 2012/0100140 | A1 | 4/2012 | Reyes et al. |
| 2012/0189643 | A1 | 7/2012 | Carton et al. |
| 2012/0225058 | A1 | 9/2012 | Lazar et al. |
| 2012/0237515 | A1 | 9/2012 | Bell et al. |
| 2012/0238729 | A1 | 9/2012 | Kuramochi et al. |
| 2012/0251531 | A1 | 10/2012 | Baehner et al. |
| 2012/0276096 | A1 | 11/2012 | Yang et al. |
| 2012/0276097 | A1 | 11/2012 | Yang |
| 2013/0011386 | A1 | 1/2013 | Brerski et al. |
| 2013/0101581 | A1 | 4/2013 | Kuramochi et al. |
| 2013/0108623 | A1 | 5/2013 | D'Angelo et al. |
| 2013/0129723 | A1 | 5/2013 | Blankenship et al. |
| 2013/0251707 | A1 | 9/2013 | Kontermann et al. |
| 2014/0088295 | A1 | 3/2014 | Smith et al. |
| 2014/0112914 | A1 | 4/2014 | Nezu et al. |
| 2014/0120581 | A1 | 5/2014 | Niwa et al. |
| 2015/0166661 | A1 | 6/2015 | Chen et al. |
| 2015/0203579 | A1 | 7/2015 | Papadopoulos et al. |
| 2015/0266966 | A1 | 9/2015 | Smith et al. |
| 2016/0130347 | A1 | 5/2016 | Bruenker et al. |
| 2016/0168247 | A1 | 6/2016 | Van Den Brink et al. |
| 2016/0347839 | A1 | 12/2016 | Davis et al. |
| 2017/0008951 | A1 | 1/2017 | Block et al. |
| 2017/0051074 | A1 | 2/2017 | Kirshner et al. |
| 2018/0104357 | A1 | 4/2018 | Rudge et al. |
| 2018/0112001 | A1 | 4/2018 | Haber et al. |
| 2018/0118848 | A1 | 5/2018 | Haber et al. |
| 2018/0194841 | A1 | 7/2018 | Smith et al. |
| 2018/0303953 | A1 | 10/2018 | Van Berkel et al. |
| 2019/0127480 | A1 | 5/2019 | Kirshner et al. |
| 2019/0389966 | A1 | 12/2019 | Crawford |
| 2020/0129617 | A1 | 4/2020 | Brownstein et al. |
| 2020/0317810 | A1 | 10/2020 | Haber et al. |
| 2024/0368312 | A1 | 11/2024 | Haber et al. |

FOREIGN PATENT DOCUMENTS

| | | | |
|---|---|---|---|
| EP | 1176981 | B1 | 11/2005 |
| EP | 1185299 | B1 | 1/2007 |
| EP | 2447372 | A2 | 5/2012 |
| EP | 2500353 | A2 | 9/2012 |
| EP | 2918604 | A1 | 9/2015 |
| EP | 3252078 | A1 | 12/2017 |
| WO | 97/028267 | A1 | 8/1997 |
| WO | 99/043713 | A1 | 9/1999 |
| WO | 99/058572 | A1 | 11/1999 |
| WO | 00/042072 | A2 | 7/2000 |
| WO | 03/026490 | A2 | 4/2003 |
| WO | 04/106380 | A2 | 9/2004 |
| WO | 04/106383 | A1 | 12/2004 |
| WO | 05/000901 | A2 | 1/2005 |
| WO | 05/040220 | A1 | 5/2005 |
| WO | 2005/118635 | A3 | 12/2005 |
| WO | 06/130458 | A2 | 12/2006 |
| WO | 07/024715 | A2 | 3/2007 |
| WO | 07/042261 | A2 | 4/2007 |
| WO | 07/093630 | A1 | 8/2007 |
| WO | 08/076379 | A3 | 6/2008 |
| WO | 08/119567 | A2 | 10/2008 |
| WO | 2008/147143 | A2 | 12/2008 |
| WO | 09/018411 | A1 | 2/2009 |
| WO | 09/023540 | A1 | 2/2009 |
| WO | 2009/030368 | A1 | 3/2009 |
| WO | 2009/106096 | A1 | 9/2009 |
| WO | 10/054212 | A1 | 5/2010 |
| WO | 10/063785 | A2 | 6/2010 |

(56) References Cited

FOREIGN PATENT DOCUMENTS

| | | | |
|---|---|---|---|
| WO | 10/085682 | A2 | 7/2010 |
| WO | 2010/151792 | A1 | 12/2010 |
| WO | 11/090762 | A1 | 7/2011 |
| WO | 11/137362 | A1 | 11/2011 |
| WO | 11/163566 | A1 | 12/2011 |
| WO | 12/022982 | A2 | 2/2012 |
| WO | 12/035141 | A1 | 3/2012 |
| WO | 12/073985 | A1 | 6/2012 |
| WO | 12/087746 | A1 | 6/2012 |
| WO | 12/109285 | A2 | 8/2012 |
| WO | 2012/143524 | A2 | 10/2012 |
| WO | 2012/162067 | A2 | 11/2012 |
| WO | 13/012733 | A1 | 1/2013 |
| WO | 13/026839 | A1 | 2/2013 |
| WO | 2013/072406 | A1 | 5/2013 |
| WO | 2013/072415 | A1 | 5/2013 |
| WO | 13/112986 | A1 | 8/2013 |
| WO | 2013/157105 | A1 | 10/2013 |
| WO | 2013/163427 | A1 | 10/2013 |
| WO | 13/184761 | A1 | 12/2013 |
| WO | 14/012085 | A2 | 1/2014 |
| WO | 14/022540 | A1 | 2/2014 |
| WO | 14/047231 | A1 | 3/2014 |
| WO | 14/051433 | A1 | 4/2014 |
| WO | 14/056783 | A1 | 4/2014 |
| WO | 14/121087 | A1 | 8/2014 |
| WO | 15/006749 | A2 | 1/2015 |
| WO | 15/091738 | A1 | 6/2015 |
| WO | 15/143079 | A1 | 9/2015 |
| WO | 16/081490 | A1 | 5/2016 |
| WO | 16/161010 | A2 | 10/2016 |
| WO | 17/053856 | A1 | 3/2017 |
| WO | 17/112762 | A1 | 6/2017 |
| WO | 18/093821 | A1 | 5/2018 |
| WO | 2021/021469 | A1 | 2/2021 |

OTHER PUBLICATIONS

Aalberse et al., "IgG4 breaking the rules," Immunology, 105(1):9-19, (2002).

Advani et al., "New immune strategies for the treatment of acute pymphoblastic leukemia: antiobodies and chimeric antigen receptors," Hematology, vol. 2013 (No. 1): (Dec. 1, 2013).

Alegre et al., "Effect of a Single Amino Acid Mutation on the Activating and Immunosuppressive Properties of a Humanized OKT3 Monoclonal Antibody", J Immunol, 148(11):3461-3468, ISSN: 0022-1767, (1992).

Almagro et al., "Humanization of antibodies," Front Biosci, vol. 13, pp. 1619-163, (2008).

Akbar et al., "A compact vocabulary of paratope-epitope interactions enables predictability of antibody-antigen binding," Cell Reports Article, vol. 34:1-15, (2021).

An et al., "IgG2m4, an engineered antibody isotype with reduced Fc function," Landes Bioscience, 1(6):572-579, (2009).

Anonymous, "Clinical Trails Register: A Phase I Study to Assess Safety and Tolerability of REGN1979, an anti-CD20 x anti- CD3 bispecific monoclonal antibody, and REGN2810, and anti-programmed death-1 (PD-1) monoclonal antibody, in Patients with B-cell Malignancies," p. 1, section A.3; p. 3, section E.1 [Retrieved from the Internet Mar. 14, 2017: <URL: https://www.clinicaltrailsregister.eu/ctr-search/trial/2015-001697-17/ES>].

Anonymous, "Study of REGN2810 and REGN1979 in Patients with Lymphoma or Acute Lymphoblastic Leukemia." [Retrieved from the Internet Mar. 15, 2017: <URL: https://www.api.liveclinicaltrials.com/trialpage?dcn=10963&city=Baltimore&country=UnitedStates&start=20&state=Maryland&conditions=lymphoma&id=207048402254>].

Armour et al., "Differential binding to human FcyRIIa and FcyRIIb receptors by human IgG wildtype and mutant antibodies," Molecular Immunology, 40:585-593, (2003).

Armour et al., "Recombinant human IgG molecules lacking Fcy receptor I binding and monocyte triggering activities", J. Immunol., 29: 2613-2624, (1999).

Baeuerle et al., "Bispecific T-cell engaging antibodies for cancer therapy," Cancer Res, 69(12):4941-4944, doi: 10.1158/0008-5472.CAN-09-0547, (2009).

Bargou et al., "Tumor egression in Cancer Patients by Very Low Doses of a T Cell-Engaging Antibody," Science Magazine, vol. 321: 974-977, (2008).

Bae et al., "Identification of the amino acid residues involved in human IgG transport into egg yolk of Japanese quail," Molucular Immunology, vol. 47:1404-1410, (2010).

Bannerji et al., "Phase 1 Study of REGN1979, an Anti-CD20 x Anti-CD3 Bispecific Monoclonal Antibody, in Patients with CD20+ B-Cell Malignancies Previously Treated with CD20-Directed Antibody Therapy," Blood, vol. 128 (22): 621 (2016). [http://doi.org/10.1182/blood.V128.22.621.621].

Bannerji et al., "Odronextamab, a human CD20xCD3 bispecific antibody in patients with CD20-positive B-cell malignancies (ELM-1): results from the relapsed or refractory non-Hodgkin lymphoma cohort in a single-arm, multicentre, phase 1 trial," Lancet Haematol, pp. 1-13; [published online [https://doi.org/10.1016/ S2352-3026(22)00072-2], Mar. 31, 2022.

Bannerji et al., "Emerging Clinical Activity of REGN1979, an Anti-CD20 x Anti-CD3 Bispecific Antibody, in Patients with Relapsed/Refractory Follicular Lymphoma (FL), Diffuse Large B-Cell Lymphoma (DLBCL), and Other B-Cell Non-Hodgkin Lymphoma (B-NHL) Subtypes," Blood, vol. 132 (Supplement No. 1): 1690, 6 pages (2018).

Bannerji et al., "Clinical Activity of REGN1979, a Bispecific Human, Anti-CD20 x Anti-CD3 Antibody, in Patients with Relapsed/Refractory (R/R) B-Cell Non-Hodgkin Lymphoma (B-NHL) ," Blood, vol. 134 (Supplement No. 1): 762, 7 pages (2019).

Bannerji et al., "Emerging Clinical Activity of REGN1979, an Anti-CD20 x Anti-CD3 Bispecific Antibody, in Patients with Relapsed/Refractory B-Cell Non-Hodgkin Lymphoma (Follicular Lymphoma, Diffuse Large B-Cell Lymphoma, and Other B-Cell Non-Hodgkin Lymphoma Subtypes)," Poster presented at the 2018 American Society of Hematology, December I-4, San Diego, GA, 1 page.

Bock et al., "Bispecific Antibodies for Non-Hodgkin Lymphoma Treatment," Curr. Treat. Options in Oncol. (2022) 23:155-170 DOI 10.1007 /s 11864-021-00925-I.

Bortoletto et al., "Optimizing anti-CD3 affinity for effective T cell targeting against tumor cells," Eur. J. Immunol., vol. 32:3102-3107, (2002).

Becker et al., "Evaluation of a combinatorial cell engineering approach to overcome apoptotic effects in XBP-1(s) expressing cells," Journal of Biotechnology, vol. 164:198-206, (2010).

Blincyto (blinatumomab) for injection, for intravenous use Initial U.S. Approval: 2014, "Highlights of Prescribing Information," package insert.

Bloom et al., "Intrachain disulfide bond in the core hinge region of human IgG4," Protein Science, 6:407-415, (1997).

Boehrer et al., "Cytotoxic effects of the trifunctional bispecific antibody FBTACI5 in ex-vivo cells of chronic lymphocytic leukemia depend on immune-mediated mechanisms," Anti-Cancer Drugs, 22:519-530, (2011).

Brekke et al., "The structural requirements for complement activation by IgG: does it hinge on the hinge?" Today, 16(2):85-90, (1995).

Brownstein et al., "First-in-human study assessing safety and tolerability of REGN1979, a novel CD20xCD3 bispecific antibody, in patients with CD20+ B-cell malignancies previously treated with anti-CD20 therapy," American Society of Clinical Oncology 51st Annual Scientific Meeting, May 29-Jun. 2, 2015; Chicago, IL; 1 page.

Buhmann et al., "Immunotherapy of recurrent B-cell malignancies after allo-SCT with Bi20 (FBTA05), a trifunctional anti-CD3 x anti-CD20 antibody and donor lymphocyte infusion," Bone Marrow Transplantation, 43:383-397, (2009).

Buhmann et al., "Immunotherapy with FBTA05 (Bi20), a trifunctional bispecific anti-CD3 x anti-CD20 antibody and donor lymphocyte

(56) References Cited

OTHER PUBLICATIONS infusion (DLI) in relapsed or refractory B-cell lymphoma after allogeneic stem cell transplantation: study protocol of an investigator-driven, open-label, non-randomized, uncontrolled, dose-escalating Phase I/II-trial," Journal of Translation Medicine, vol. 11:160, (2013); 9 pages. [Retrieved from the Internet at: <http://www.translational-medicine.com/content/11/1/1160>].
Canfield et al., "The Binding Affinity of Human Igg for Its High Affinity FC Receptor is Determined by Multiple Amino Acids in the Ch2 Domain and is Modulated by the Hinge Region," J. Exp. Med., 173(6):1483-1491, (1991).
Cao et al., "Multiformat T-Cell-Engaging Bispecific Antibodies Targeting Human Breast Cancers," Angew Chem Int Ed Engl, 54(24):7022-7027, doi: 10.1002/anie.201500799, (2015).
Carter, "Potent Antibody Therapeutics by Design," Journal of Immunology, Nature Pub. Group, 6:343-357, (2006).
Chan et al., "Therapeutic antibodies for autoimmunity and inflammation," Macmillan Publishers Limited (Nature Reviews, Immunology), vol. (10):301-316, (2010).
Chen et al., "Strategies for Generating Diverse Antibody Reportoires Using Transgenic Animals Expressing Human Antibodies," Front. Immunol. vol. 9, Article 460; Mar. 2018; 7 pages. doi: 10.3389/fimmu.2018.00460.
Chappel et al., "Identification of a Secondary FcγRI Binding Site within a Genetically Engineered Human IgG," Journal of Biological Chemistry, 268(33): 25124-25131, (1993).
Chappel et al., "Identification of the FC-Gamma Receptor Class I Binding Site in Human Igg Through the Use of Recombinant Igg1-Igg2 Hybrid and Point-Mutated Antibodies," Proc. Natl. Acad. Sci. USA, 88(20):9036-9040, (1991).
Chatenoud et al., "CD3-specific antibodies: a portal to the treatment of autoimmunity," Nature, vol. (7): 622-632, (Aug. 2007). [doi:10.1038/nri2134: <URL: www.nature.com/reviews/immunol>].
Chiu et al., "Antibody Structure and Function: The Basis for Engineering Therapeutics," Antibodies, vol. 8 (No. 55): 1-80, (2019). [doi: 10.3390/antib8040055].
Clark, "IgG Effector Mechanisms," Chem Immunol. Basel, Karger, 65:88-110, (1997).
Conrad et al., "TCR and CD3 Antibody Cross-Reactivity in 44 Species," Cytometry Part A, 71A:925-933, (2007).
Dall'Acqua et al., "Modulation of the Effector Functions of a Human IgG1 through Engineering of Its Hinge Region," Journal of Immunology, 177:1129-1138, (2006).
Damschroder et al., "Analysis of human and primate CD2 molecules by protein sequence and epitope mapping with anti-human CD2 antibodies," Molecular Immunology, vol. 41:985-1000, (2004).
Dangl et al., "Segmental flexibility and complement fixation of genetically engineered chimeric human, rabbit and mouse antibodies," The EMBO Journal, 7(7):1989-1994, (1988).
Duncan et al., "Localization of the binding site for the human high-affinity Fc receptor on lgG", Nature, 332:563-564, (1988).
Frey et al., "Cytokine release syndrome: Who is at risk and how to treat," Best Practice & Research Clinical Haematology, vol. 30 (No. 4): 336-340, (Dec. 2017). [Retrieved from the Internet Sep. 11, 2023: <URL: https://www.sciencedirect.com/journal/best-practice-and-research-clinical-haematology>].
Fossati et al., "Immunological changes in the ascites of cancer patients after intraperitoneal administration of the bispecific antibody catumaxomab (anti-EpCAManti-CD3)," Gynecol Oncol, 138(2):343-351, doi: 10.1016/J.YGYNO.2015.06.003, (2015).
Gall et al., "T cells armed with anti-CD3 x anti-CD20 bispecific antibody enhance killing of CD20+ malignant B cells and bypass complement-mediated rituximab resistance in vitro", Experimental Hematology, 33(4):452-459, (2005).
Gergely et al., "The two binding-site models of human IgG binding Fcy receptors", The FASEB Journal, 4:3275-3283, (1990).
Greenwood et al., "Structural Motifs Involved in Human IGG Antibody Effector Functions," Eur. J. Immunology, 23(5):1098-1104, (1993).
Grubb, "Human Immunoglobulin Allotypes and Mendelian Polymorphisms of the Human Immunoglobulin Genes," in Oss CJ, Regenmortel MHV (eds); Immunochemistry, New York, Dekker (1994); pp. 47-68.
Harlow et al., Antibodies, A Laboratory Manual, Cold Spring Harbor Laboratory; (1998) pp. 37-47.
Haso et al., "Anti-CD22-chimeric antigen receptors targeting B-cell precursor acute lymophoblastic leukemia," Blood, vol. 121(No. 7):1165-1174, (2013).
Hezareh et al., "Effector function activities of a panel of mutants of a broadly neutralizing antibody against human immunodeficiency virus type 1," J Virol, 75(24):12161-12168, doi: 10.1128/JVI.75.24.12161-12168.2001, (2001).
Jacobsen et al., "Molecular and Functional Characterization of Cynomolgus Monkey IgG Subclasses," Journal Immunology, 186:341-349, (2011).
Jefferis et al., "Interaction sites on human IgG-Fc for FcyR: current models", Immunology Letters, 82:57-65, (2002).
Jefferis et al., "Recognition sites on human IgG for Fcy receptors: the role of glycosylation," Immunology Letters, 44:111-117, (1995).
Jung et al., "Target Cell-Induced T Cell Activation with Bi- and Trispecific Antibody Fragments", Eur J Immunol, vol. 21, pp. 2431-2435, doi: 10.1002/EJI.1830211020, (1991).
Kapur et al., "IgG-effector functions: The Good, the Bad and the Ugly," El Sevier, vol. 160:139-144, (2014).
Kazutomo, Biochemical Encyclopedia, 1998, 3rd Edition, pp. 265 to 266.
Klein et al., "Progress in overcoming the chain association issue in bispecific heterodimeric IgG antibodies," mAbs, Landes Bioscience, 4(6):1-11, (2012).
Klinger et al., "Immunopharmacologic response of patients with B-lineage acute lymphoblastic leukemia to continuous infusion of T cell-engaging CD19/CD3-bispecific BiTE antibody blinatumomab," Blood, 119:6226-6233, (2012).
Kim et al., Slides for the 64th American Society of Hematology (ASH) Annual Meeting and Exposition "Odronextamab in Patients with Relapsed/Refractory (R/R) Diffuse Large B-Cell Lymphoma (DLBCL): Results from a Prespecified Analysis of the Phase 2 Study ELM-2" Medical writing support was provided by Lewis Cawkwell of Arc, a division of Spirit Medical Communications Group Limited, and funded by Regeneron Pharmaceuticals, Inc.; 16 slides. Oct. 10-13, 2022.
Kim et al., Slides for the 64th American Society of Hematology (ASH) Annual Meeting and Exposition "Odronextamab in Patients with Relapsed/Refractory (R/R) Follicular Lymphoma (FL) Grade 1-3a: Results from a Prespecified Analysis of the Phase 2 Study ELM-2" Medical writing support was provided by Lewis Cawkwell of Arc, a division of Spirit Medical Communications Group Limited, and funded by Regeneron Pharmaceuticals, Inc.; 16 slides. (Oct. 10-13, 2022).
Kim et al., "A Phase 2 Study of Odronextamab (REGN1979), a CD20 x CD3 Bispecific Antibody, in Patients with Relapsed/Refractory B-Cell Non-Hodgkin Lymphoma ," Blood, vol. 136 (Supplement 1) : 28, 4 pages (2020).
Kontermann, "Dual targeting strategies with bispecific antibodies," mAbs, Landes Bioscience, 4(2):182-197, (2012).
Köhnke et al., "Increase of PD-L1 expressing B-precursor ALL cells in a patient resistant to the CD19/CD3-bispecific T cell engager antibody blinatumomab," Journal of Hematoloty & Oncology, vol. 8 (No. 111):5 pages, (2015).
Kumar et al., "Expression of CD20 in B Cell Precursor Acute Lymphoblastic Leukemia," Indian J. Hematol Blood Transfus, vol. 30 (No. 1):16-18, (2014).
Kung et al., "Monoclonal Antibodies Defining Distinctive Human T Cell Surface Antigens," Science, 206:347-349, (1979).
Labrijn et al., "When binding is enough: nonactivating antibody formats", Current Opinion in Immunology, 20:479-485, (2008).
Lau et al., "Chimeric Anti-CD14 IGG2/4 Hybrid Antibodies for Therapeutic Intervention in Pig and Human Models of Inflammation," J Immunol, 191:4769-4777, doi: 10.4049/jimmunol.1301653, (2013).

(56) References Cited

OTHER PUBLICATIONS

Le Tourneau et al., "Dose Escalation Methods in Phase I Cancer Clinical Trials," National Cancer Institute, vol. 101 (Issue 10): 708-720, (2009).
Leonard et al., "Targeted Treatment and New Agents in Diffuse Large B-Cell Lymphoma," Semin Hematol, 45(suppl 2):S11-S16, (2008).
Li et al., "A Novel Bispecific Antibody, S-Fab, Induces Potent Cancer Cell Killing," J Immunother, 38(9):350-356, doi: 10.1097/CJI.0000000000000099, (2015).
Liu et al., "Improvement in soluble expression levels of a diabody by exchanging expression vectors", Protein Expression and Purification, 62:15-20, (2008).
Lum et al., "CD20-Targeted T Cells after Stem Cell Transplantation for High Risk and Refractory Non-Hodgkin's Lymphoma," Pbiol Blood Marrow Transplant, 19(6):925-933, (2013).
Lum et al., "Multiple infusions of CD20-targeted T cells and low-dose IL-2 after SCT for high-risk non-Hodgkin's lymphoma: A pilot study," Bone Marrow Transplantation, 49:73-79, (2004). [Puplished online Sep. 23, 2013].
Lund et al., "Human FcyRI and FcyRII Interact with Distinct but Overlapping Sites on Human IgG", Journal of Immunology, 147(8):2657-2662, (1991).
Lo et al., "Conformational epitope matching and prediction based on protein surface spiral features," BMC Genomics, vol. 22 (No. 2): 1-16, (2021). [https://doi.org/10.1186/s12864-020-07303-5].
Marks et al., "How repertoire data are changing antibody science," JBC Reviews, vol. 295 (No. 29): 9823-937, (2020).
Maude et al., "Managing Cytokine Release Syndrome Associated With Novel T Cell-Engaging Therapies," Cancer Journal, vol. 20(2): 119-122, (2014).
Michaelsen et al., "Antibody Dependent Cell-Mediated Cytotoxicity Induced by Chimeric Mouse-Human IgG Subclasses and IgG3 Antibodies with Altered Hinge Region," Molecular Immunology, 29(3):319-326, (1992).
Morgan et al., "The N-terminal end of the CH2 domain of chimeric human IgG1 anti-HLA-DR is necessary for Gig, FcyRI and FcyRII binding," Immunology, 86:319-324, (1995).
Mueller et al., "Humanized Porcine VCAM-Specific Monoclonal Antibodies with Chimeric IgG2/G4 Constant Regions Block Human Leukocyte Binding to Porcine Endothelial Cells," Molecular Immunology, 34(6): 441-452, (1997).
Nagorsen et al., "Blinatumomab: A historical perspective," Pharmacology & Therapeutics, 136:334-342 (2012).
Natsume et al., "Engineered Antibodies of IgG1IIgG3 Mixed Isotype with Enhanced Cytotoxic Activities," Cancer Research, 68:(10):3863-3872, (2008).
NCBI MedGen 44126 definition for "Pre-B Acute Lymphoblastic Leukemia" retrieved from the Internet on Dec. 11, 2018; pp. 1-4, available at <https://www.ncbi.nlm.nih.gov/medgen/44126> (2018).
Oganesyan et al., "Structural characterization of a human Fc fragment engineered for lack of effector functions," Acta Crystallographica Section D Biological Crystallography, D64:700-704, (2008).
Ontology Lookup Serviec, EFO 0000220, "acute lumphoblastic leukemia" retrieved from the Internet on Dec. 11, 2018, pp. 1-6; available at <http://www.ebi.ac.uk/ols/ontologies/efo/terms?short_form=EFO_0000220> (2018).
Patel et al., "IGG subclass variation of a monoclonal antibody binding to human Fc-gamma receptors", American Journal of Biochemistry and Biotechnology, 9(3):206-218, (2013).
Pessano et al., "The T3/T cell receptor complex: antigenic distinction between the two 20-kd T3 (T3-δ and T3-€) subunits," The EMBO Journal, 4(2):337-344, (1985).
Peters et al., "Engineering an Improved IgG4 Molecule with Reduced Disulfide Bond Heterogeneity and Increased Fab Domain Thermal Stability," Journal of Biological Chemistry, 287(29): 24525-24533, (2012).
Press Release: U.S. FDA Approves DARZALEX® (daratumumab) Split-Dosing Regimen, Feb. 12, 2019. (www.janssen.com).
Reddy et al., "Elimination of Fc Receptor-Dependent Effector Functions of a Modified IgG4 Monoclonal Antibody to Human CD4," Journal of Immunology, 164:1925-1933, (2000).
Removab 10 microgram concentrate for solution for infusion packaeg; Annex 1; Summay of Product Characteristics, 1-44, package insert.
Rother et al., "Discovery and development of the complement inhibitor eculizumab for the treatment of paroxysmal nocturnal hemoglobinuna," Nature Biotechnology, 25(11):1256-1264, (2007).
Roux et al., "Comparisons of the ability of human IgG3 hinge mutants, IgM, IgE and IgA2, to form small immune complexes: Arole for flexibility and geometry," The Journal of Immunology, 161:4083-4090, (1998).
Roux et al., "Flexibility of Human IgG Subclasses," Journal of Immunology, 159:3372-3382, (1997).
Ruf et al., "Induction of a long-lasting antitumor immunity by a trifunctional bispecific antibody," Blood Journal, vol. 98, No. 9: 2526-2534, (2001).
Richards et al., "Optimization of antibody binding to FcyRIIa enhances macrophage phagocytosis of tumor cells," Molecular Cancer Therapeutics (Xencor, Inc.), vol. (8):2517-2527, (2008). [Retrieved from the Internet Sep. 16, 2020: <URL: met.aacrjournals.org>].
Scott et al., "Antibody Therapy of Cancer," Nature, vol. 12:278-287, (Apr. 2012).
Sun, "Structural Recognition of Immunoglobulins by Fcγ Receptors," Elsevier Science & Technology, Ch. 7:131-144, (2013).
Salfeld, "Isotype selection in antibody engineering," Nature Biotechnology, 25(12):1369-1372, (2007).
Sarmay et al., "Mapping and Comparison of the Interaction Sites on the Fc Region of IgG Responsible for Triggering Antibody Dependent Cellular Cytotoxicity (ADCC) through Different Types of Human Fcy Receptor," Molecular Immunology, 29(5):633-639, (1992).
Sathish et al., "Challenges and approaches for the development of safer immunomodulatory biologics," Nature Reviews Drug Discovery, 12:306-324, (2013).
Schaefer et al., "Immunoglobulin domain crossover as a generic approach for the production of bispecific IgG antibodies," PNAS, 108(27):11187-11192, doi: 10.1073/pnas.1019002108, (2011).
Schuster et al., "Immunotherapy with the trifunctional anti-CD20 x anti-CD3 antibody FBTA05 Lymphomun) in paediatric high-risk patients with recurrent CD20-positive B cell malignancies," British Journal of Haematolgy, vol. 169 (No. 1): (Apr. 11, 2015); pp. 90-102.
Segal et al., "Bispecific antibodies in cancer therapy," Current Opinion in Immunology, 11:558-562, (1999).
Sensel et al., "Amino Acid Differences in the N-Terminus of CH2 Influence the Relative Abilities of IgG2 and IgG3 to Activate Complement", Molecular Immunology, 34(14):1019-1029, (1997).
Shields et al., High resolution mapping of the binding site on human IgG1 for FcgammaRI, FcganmaRII, FcgammaRIII, and FcRn and design of IgG1 variants with improved binding to the FcgammaR, J Biol Chem, 276(9):6591-6604, doi: 10.1074/JBC.M009483200, (2001).
Siberil et al., "Molecular aspects of human FcyR interactions with IgG: Functional and therapeutic consequences," Immunology Letters, 106:111-118, (2006).
Siiman et al., "Cell Surface Receptor-Antibody Association Constants and Enumeration of Receptor Sites for Monoclonal Antibodies," Cytometry, 40:316-326, (2000).
Topp et al., "Safety and activity of blinatumomab for adult patients with relapsed or refractory B-precursor acute lymphoblastic leu,aemia: a multiventre, single-arm, phase 2 study," The Lancet, vol. 16:57-66, (2015).
Topp et al., "Safety and Preliminary Antitumor Activity of the Anti-PD-1 Monoclonal Antibody REGN2810 Alone or in Combination with REGN1979, an Anti-CD20 x Anti-CD3 Bispecific Antibody, in Patients with B-Lymphoid Malignancies," Blood, vol. 130 (Supplement No. 1): 1495, (2017).
Tsai et al., "Regulation of CD20 in Rituximab-Resistant Cell Lines and B-cell Non-Hodgkin Lymphoma," Clinical Cancer Research, vol. 18(No. 4):1039-1050, (2012).

(56) References Cited

OTHER PUBLICATIONS

U.S. Appl. No. 14/031,075, Final Office Action mailed Sep. 14, 2016.
U.S. Appl. No. 14/031,075, Non-Final Office Action mailed Apr. 15, 2016.
U.S. Appl. No. 14/031,075, Notice of Allowance mailed Jan. 18, 2014.
U.S. Appl. No. 14/031,075, Requirement for Restriction/Election mailed Nov. 19, 2015.
U.S. Appl. No. 14/170,166, Non-Final Office Action mailed Dec. 21, 2015.
U.S. Appl. No. 14/170,166, Notice of Allowance mailed Apr. 11, 2016.
U.S. Appl. No. 14/170,166, Requirement for Restriction/Election mailed Jul. 27, 2015.
U.S. Appl. No. 14/661,334, Requirement for Restriction/Election mailed Mar. 6, 2017.
U.S. Appl. No. 14/661,334, Requirement for Restriction/Election mailed 09-11- 2017.
U.S. Appl. No. 14/661,334, Non-Final Office Action mailed Dec. 18, 2018.
U.S. Appl. No. 14/661,334, Final Office Action mailed Jun. 27, 2019.
U.S. Appl. No. 14/661,334, Notice of Allowance mailed Sep. 17, 2019.
U.S. Appl. No. 15/147,791, Non-Final Office Action mailed Sep. 27, 2017.
U.S. Appl. No. 15/147,791, Notice of Allowance mailed Mar. 1, 2018.
U.S. Appl. No. 15/147,791, Notice of Allowance mailed Jun. 12, 2018.
U.S. Appl. No. 15/386,443, Requirement for Restriction/Election mailed Apr. 20, 2018.
U.S. Appl. No. 15/386,443, Requirement for Restriction/Election mailed Sep. 19, 2018.
U.S. Appl. No. 15/386,443, Non-Final Office Action mailed Dec. 18, 2018.
U.S. Appl. No. 15/934,447, Requirement for Restriction/Election mailed Oct. 17, 2019.
U.S. Appl. No. 15/489,666, Requirement for Restriction/Election mailed Jun. 18, 2019.
U.S. Appl. No. 15/527,002, Requirement for Restriction/Election mailed Aug. 24, 2018.
U.S. Appl. No. 15/527,002, Non-Final Office Action mailed Mar. 8, 2019.
U.S. Appl. No. 15/562,881, Notice of Allowance mailed Jun. 12, 2019.
U.S. Appl. No. 15/562,881, Notice of Allowance mailed Sep. 25, 2019.
U.S. Appl. No. 15/527,002, Notice of Allowance mailed Jan. 13, 2020.
U.S. Appl. No. 15/489,666, Non-Final Office Action mailed Feb. 11, 2020.
U.S. Appl. No. 15/780,504, Requirement for Restriction/Election mailed 04-07- 2020.
U.S. Appl. No. 15/934,447, Non-Final Office Action mailed May 8, 2020.
U.S. Appl. No. 15/489,666, Final Office Action mailed Sep. 10, 2020.
U.S. Appl. No. 16/128,907, Non-Final Office Action mailed Sep. 22, 2020.
U.S. Appl. No. 15/780,504, Non-Final Office Action mailed Oct. 20, 2020.
U.S. Appl. No. 15/934,447, Final Office Action mailed Dec. 4, 2020.
U.S. Appl. No. 15/489,666, Notice of Allowance mailed Mar. 24, 2021.
U.S. Appl. No. 15/934,447, Notice of Allowance mailed Jun. 24, 2021.
U.S. Appl. No. 16/720,623, Non-Final Office Action mailed Feb. 14, 2022.
U.S. Appl. No. 16/556,885, Requirement for Restriction/Election mailed Nov. 9, 2021.
U.S. Appl. No. 16/556,885, Non-Final Office Action mailed Mar. 29, 2022.
U.S. Appl. No. 16/556,885, Notice of Allowance mailed Oct. 26, 2022.
U.S. Appl. No. 17/355,532, Non-Final Office Action mailed May 19, 2023.
U.S. Appl. No. 17/207,462, Final Office Action mailed Sep. 20, 2023.
U.S. Appl. No. 16/716,980, Notice of Allowance mailed Apr. 28, 2022.
U.S. Appl. No. 16/720,623, Notice of Allowance mailed Jul. 7, 2022.
Vafa, et al., "An engineered Fc variant of an IgG eliminates all immune effector functions via structural perturbations", 65:114-126, (2014). (Published online Jul. 17, 2013).
Van Meerten et al., "CD20-Targeted Therapy: The Next Generation of Antibodies," Semin Hematol, 47:199-210, (2010).
Varghese et al., "A Novel CD20-CD3 Bispecific Fully Human Antibody Induces Potent Anti-Tumor Effects Against B Cell Lymphoma in Mice," Blood, vol. 124 (21) 4501 (2014). [http://doi.org/10.1182/blood.V124.21.4501.4501].
Vajda et al., "Progress toward improved understanding of antibody maturation," ScienceDirect, vol. 67: 226-231, (2021).
Venclexta (venetoclax) tablets, for oral use Initial U.S. Approval: 2016; "Highlights of Prescribing Information.," package insert.
Vidarsson et al., "IgG Subclasses and Allotypes: From Structure to Effector Functions," Frontiers in Immunology, vol. 5, Article 520, 18 pages, doi: 10.3389/fimmu.2014.00520, (2014).
Ward et al., "The effector functions of immunoglobulins: implications for therapy," Therapeutic Immunology, 2:77-94, (1995).
Wark et al., "Latest technologies for the enhancement of antibody affinity", Advanced Drug Delivery Reviews, 58(5-6):657-670, (2006).
Wang et al., "Treatment of CD33-directed Chimeric Antigen Receptor-modified T Cells in One Patient With Relapsed and Refractory Acute Myeloid Leukemia," The American Society of Gene & Cell Therapy, vol. 23 (No. 1), 184-191 (2015).
Winkler et al., "Changing the Antigen Binding Specificity by Single Point Mutations of an Anti-p24 (HIV-1) Antibody," J. Immunol., 165:4505-4514, (2000).
Weinglass et al., "Engineering Conformational Flexibility in the Lactose Permease of *Escherichia coli:* Use of Glycine-Scanning Mutagenesis to Rescue Mutant Glu325-Asp," Biochemistry, vol. 40:769-776, (2001).
WIPO Application No. PCT/US2013/060511, PCT International Search Report and Written Opinion of the International Searching Authority mailed Feb. 20, 2014.
WIPO Application No. PCT/US2014/014175, PCT International Preliminary Report on Patentability mailed Aug. 13, 2015.
WIPO Application No. PCT/US2014/014175, PCT International Search Report and Written Opinion of the International Searching Authority mailed Jul. 9, 2014.
WIPO Application No. PCT/US2015/021322, PCT International Search Report and Written Opinion of the International Searching Authority mailed Jul. 2, 2015.
WIPO Application No. PCT/US2015/061139, PCT International Search Report and Written Opinion of the International Searching Authority mailed Feb. 18, 2016.
WIPO Application No. PCT/US2016/025051, PCT International Search Report and Written Opinion of the International Searching Authority mailed Oct. 12, 2016.
WIPO Application No. PCT/US2016/053525, PCT International Search Report and Written Opinion of the International Searching Authority mailed Mar. 8, 2017.
WIPO Application No. PCT/US2016/068003, PCT International Search Report mailed Mar. 31, 2017.
WIPO Application No. PCT/US2016/068003, PCT Written Opinion of the International Searching Authority mailed Mar. 31, 2017.
WIPO Application No. PCT/US2019/049027, PCT International Search Report and Written Opinion of the International Searching Authority mailed Nov. 28, 2019.

(56) References Cited

OTHER PUBLICATIONS

WIPO Application No. PCT/US2023/013836, PCT International Search Report and Written Opinion of the International Searching Authority mailed Jun. 23, 2023.
Wolach et al., "Blinatumomab for the Treatment of Philadelphia Chromosome-Negative, Precursor B-cell Acute Lymphoblastic Leukemia," Clinical Cancer Research, vol. 21 (No. 19):4262-4269, (2015).
Wu et al., "Fab-based bispecific antibody formats with robust biophysical properties and biological activity," MABS, pp. 470-482, ISSN: 1942-0870, (2015).
Wypych et al., "Human lgG2 Antibodies Display Disulfide-mediated Structural Isoforms," Journal of Biological Chemistry, 283(23):16194-16205, (2008).
Xiong et al., "Efficient inhibition of human B-cell lymphoma xenografts with an anti-CD20 X anti-CD3 bispecific diabody", Cancer Letters, 177:29-39, (2002).
Yuen et al., "B lymphocytes and cancer: a love-hate relationship," Trends Cancer Dec. 2016; 2(12): 747-757.
Xu et al., "Residue at Position 331 in the Igg1 and Igg4 Ch2 Domains Contributes to Their Differential Ability to Blind and Activate Complement," Journal of Biological Chemistry, 269(5):3469-3474, (1994).
P01834 (GenPept, Ig kappa chain C region, pp. 1-4, Feb. 19, 2014). (Year: 2014).
"Bannerji et al., "Safety and Preliminary Clinical Activity of REGN1979, an Anti-CD20 x Anti-CD3 Bispecific Antibody, in Patients with BNHL Previously Treated with CD20-Directed Antibody Therapy," Blood blood, vol. 130 (Suppl_1) :550, pp. 1-4 [http://doi.org/10.1182/blood.V130.Suppl_1.1550.1550]."
Chao et al. (Cancer Management and Research 2013:5 251-269). (Year: 2013).
Hamed Ebtisam et al: "Long-term outcomes of CAR-T cell therapy in DLBCL", Journal of Clinical Oncology, vol. 43, No. 16_suppl, E19004, Jun. 1, 2025 (Jun. 1, 2025), XP093299974, [ISSN: 0732-183X, DOI: 10.1200/JCO.2025.43.16_suppl.e19004].
Lawrence L: "What's the Best Route After CAR-T Failure in B-Cell Lymphoma?" Blood Cancers Today, Feb. 7, 2023 (Feb. 7, 2023), pp. 1-13, XP093299979, [Retrieved from the Internet: URL:https://www.bloodcancerstoday.com/post/an-unclear-path-whats-the-best-route-after-car-t-failure-in-b-cell-lymphoma].
Quintás-Cardama et al., "CD19 directed Car T cell therapy in diffuse large B-cell lymphoma," Oncotarget, vol. 9, (No. 52), pp. 29843-29844 (2018).
Regeneron: "Regeneron CD20xCD3 Bispecific REGN1979 Shows Positive Results in Patients with Relapsed or Refractory B-cell Non-Hodgkin Lymphoma, including in CAR-T Failures", Jun. 14, 2019 (Jun. 14, 2019), pp. 1-3, XP093299866, [Retrieved from the Internet: URL:https://newsroom.regeneron.com/node/22521/pdf].
Sava J. et al: "Odronextamab Shows Efficacy in DLBCL Post CAR T-Cell Therapy", Targeted Oncology, Mar. 10, 2025 (Mar. 10, 2025), pp. 1-7, XP093299969, [Retrieved from the Internet: URL:https://www.targetedonc.com/view/odronextamab-shows-efficacy-in-dlbcl-post-car-t-cell-therapy].
U.S. Appl. No. 18/101,310, Non-Final Office Action mailed Oct. 28, 2025.
U.S. Appl. No. 17/207,462, Notice of Allowance mailed Nov. 12, 2025.
U.S. Appl. No. 18/512,432, Notice of Allowance mailed Dec. 2, 2025.
U.S. Appl. No. 18/114,057, Requirement for Restriction/Election mailed Nov. 18, 2025.
U.S. Appl. No. 17/875,295, Non-Final Office Action mailed Oct. 20, 2025.
U.S. Appl. No. 17/217,567, Non-Final Office Action mailed Nov. 29, 2023.
U.S. Appl. No. 18/512,432, Final Office Action mailed May 12, 2025.
U.S. Appl. No. 17/961,442, Notice of Allowance mailed Aug. 25, 2025.
U.S. Appl. No. 18/512,432, Non-Final Office Action mailed Oct. 16, 2024.
U.S. Appl. No. 17/961,442, Non-Final Office Action mailed Mar. 3, 2025.
U.S. Appl. No. 17/217,567, Final Office Action mailed Apr. 14, 2025.
U.S. Appl. No. 17/875,295, Non-Final Office Action mailed Mar. 13, 2025.
U.S. Appl. No. 17/217,567, Notice of Allowance mailed Aug. 26, 2025.
U.S. Appl. No. 17/217,567, Final Office Action mailed Mar. 7, 2024.
U.S. Appl. No. 17/207,462, Non-Final Office Action mailed Apr. 17, 2024.
U.S. Appl. No. 17/207,462, Non-Final Office Action mailed Mar. 24, 2025.
"Wong et al. (Haematologica. Dec. 2013 98(12):1930-1938, supplemental pages included, document has been renumbered as pp. 1-27). (Year: 2013)".
Zavras PD et al: "Evaluating tisagenlecleucel and its potential in the treatment of relapsed or refractory diffuse large B cell lymphoma: evidence to date", Oncotargets and Therapy, vol. 12, Jun. 11, 2019 (Jun. 11, 2019), pp. 4543-4554, XP093299992, [ISSN: 1178-6930, DOI: 10.2147/OTT.S177844].
Smith et al., "A novel, native-format bispecific antibody triggering T-cell killing of B-cell is robustly active in mouse tumor models and cynomolgus monkeys," Scientific Reports, vol. 5(No. 11):(Dec. 11, 2015); p. 17943.
Stanglmaier et al., "Bi20 (FBTA05), a novel trifunctional bispecific antibody (anti-CD20 x anti-CD3), mediates efficient killing of B-cell lymphoma cells even with very low CD20 expression levels", Int. J. Cancer, 123(5):1181-1189, (2008).
Stel et al., "The role of B cell-mediated T cell costimulation in the efficacy of the T cell retargeting bispecific antibody BIS20x3," J Immunol, 173(10):6009-6016, (2004).
Stevenson, "Chemical Engineering at the Antibody Hinge," Chem Immunol. Basel, Karger, 65:57-72, (1997).
Strop et al., "Generating Bispecific Human IgG1 and IgG2 Antibodies from Any Antibody Pair", J. Mol. Biol., 420(3):204-219, (2012).
Stubenrauch et al., "Impact of Molecular Processing in the Hinge Region of Therapeutic IgG4 Antibodies on Disposition Profiles in Cynomolgus Monkeys," Drug Metabolism and Disposition, vol. 38(No. 1):84-91, (2010).
Sun et al., "Anti-CD20/CD3 T cell-dependent bispecific antibody for the treatment of B cell malignancies," Science Translational Medicine, 7(287):287ra70, 10 pages, (2015).
Supplementary Appendix to Bannerji et al., "Odronextamab, a human CD20xCD3 bispecific antibody in patients with CD20-positive B-cell malignancies (ELM-1): results from the relapsed or refractory non-Hodgkin lymphoma cohort in a single-arm, multicentre, phase 1 trial," Lancet Haematol, pp. 1-21; published online [https://doi.org/10.1016/ S2352-3026(22)00072-2], Mar. 31, 2022.
Tan et al., "Influence of the hinge region on complement activation, C1q binding, and segmental flexibility in chimeric human immunoglobulins,", Proc. Natl. Acad. Sci. USA, 87:162-166, (1990).
Teeling et al., "Characterization of new human CD20 monoclonal antibodies with potent cytolytic activity against non-Hodgkin lymphomas," Blood, 104:1793-1800, (2004).
Thakur et al., "Activated T cells from umbilical cord blood armed with anti-CD3 x anti-CD20 bispecific antibody mediate specific cytotoxicity against CD20+ targets with minimal allogeneic reactivity: a strategy for providing antitumor effects after cord blood transplants", Transfusion, 52:63-75, (2012).
Thakur et al., "Cancer therapy with bispecific antibodies: Clinical experience," NIH Public Access, Curr Opin Mol Ther., vol. 12(3): 340-349, (2010).
Thomas et al., "Chemioimmunotherapy with a modified hyper-CVAD and Rituximab Regiment improves outcome in De Novo Philadelphia Chromosome-Negative Precursor B-Lineage Acute Lymphoblastic Leukemia," Journal of Clinical Oncology, vol. 28 (No. 24):3880-3889, (2010).

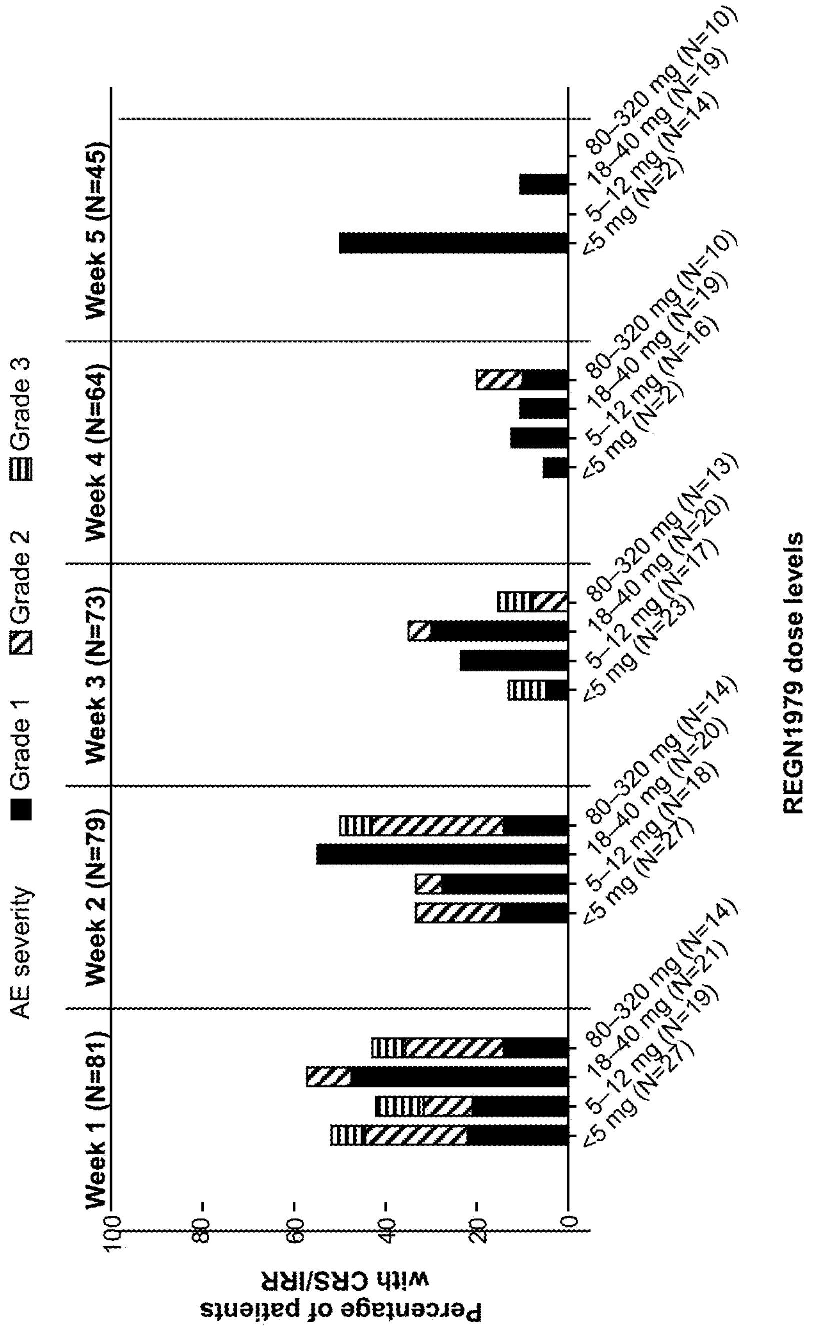
AE severity
Grade 1
Grade 2
Grade 3
Week 1 (N=81)
Week 2 (N=79)
Week 3 (N=73)
Week 4 (N=64)
Week 5 (N=45)
Percentage of patients with CRS/IRR
0
20
40
60
80
100
<5 mg (N=27)
5–12 mg (N=19)
18–40 mg (N=21)
80–320 mg (N=14)
<5 mg (N=27)
5–12 mg (N=18)
18–40 mg (N=20)
80–320 mg (N=14)
<5 mg (N=23)
5–12 mg (N=17)
18–40 mg (N=20)
80–320 mg (N=13)
<5 mg (N=2)
5–12 mg (N=16)
18–40 mg (N=19)
80–320 mg (N=10)
<5 mg (N=2)
5–12 mg (N=14)
18–40 mg (N=19)
80–320 mg (N=10)
REGN1979 dose levels

DOSING STRATEGY THAT MITIGATES CYTOKINE RELEASE SYNDROME FOR THERAPEUTIC ANTIBODIES

CROSS-REFERENCE TO RELATED APPLICATIONS

This application is a continuation of U.S. application Ser. No. 16/556,885, filed Aug. 30, 2019, now U.S. Pat. No. 11,590,223, which claims the benefit under 35 USC §119(e) of US Provisional Application Nos.: 62/726,137, filed Aug. 31, 2018; 62/774,019, filed Nov. 30, 2018; and 62/861,100, filed Jun. 13, 2019, each of which is incorporated herein by reference in its entirety for all purposes.

REFERENCE TO A SEQUENCE LISTING

This application incorporates by reference a computer readable Sequence Listing in ST.26 XML format, titled 10496US02_Sequence, created on Jan. 25, 2023 and containing 48,703 bytes.

FIELD OF THE INVENTION

The present invention lies in the field of medicine, and relates to dosing strategies and administration regimens for therapeutic antibodies (e.g., bispecific antibodies targeting T cells) that mitigate the prevalence and severity of cytokine release syndrome or an infusion-related reaction in patients undergoing immunotherapy.

BACKGROUND

Cytokine release syndrome (CRS) is a systemic inflammatory response that can be triggered by a variety of factors, including certain drugs. T cell-activating cancer immunotherapies carry a particularly high risk of CRS, which is usually due to on-target effects induced by binding of a bispecific antibody or chimeric antigen receptor (CAR) T cell to its antigen and subsequent activation of bystander immune cells and non-immune cells, such as endothelial cells. Activation of the bystander cells results in the massive release of a range of cytokines. IL-6, IL-10, and interferon (IFN)-γ are among the core cytokines that are consistently found to be elevated in serum of patients with CRS. With T cell-activating therapies directed against tumor cells, CRS is triggered by the massive release of IFN-γ by activated T cells or the tumor cells themselves. Secreted IFN-γ induces activation of other immune cells, most importantly macrophages, which in turn produce excessive amounts of additional cytokines such as IL-6, TNF-α, and IL-10. IL-6, in particular, contributes to many of the key symptoms of CRS, including vascular leakage, and activation of the complement and coagulation cascade inducing disseminated intravascular coagulation. In addition, IL-6 likely contributes to cardiomyopathy by promoting myocardial dysfunction. Shimabukaro-Vornhagen et al., *Journal for Immunotherapy of Cancer,* 6:56, pp. 1-14, 2018. In some cases, the symptoms associated with CRS are termed infusion-related reaction (IRR) if they occur less than six hours following the start of infusion, and CRS if they occur from six hours onward following the start of infusion.

The management of the toxicities of cancer immunotherapy is a challenging clinical problem. Mitigating CRS or IRR is a hallmark of administering certain treatment modalities, for example CAR T cells and bispecific antibodies targeting T cells. Low grade CRS is generally treated symptomatically with anti-histamines, antipyretics and fluids. Severe CRS can represent a life-threatening adverse event that requires prompt and aggressive treatment. Reduction of tumor burden, limitations on the dose of administered therapy, and premedication with steroids have reduced the incidence of severe CRS, as have the use of anti-cytokine treatments. Tocilizumab, an anti-IL-6 antibody, has become a standard initial treatment for severe CRS in some circumstances. However, the use of dose limitations and treatments to minimize cytokine activity can have detrimental effects on the efficacy of the immunotherapy. Thus, there remains a need for alternative strategies to mitigate the potential life-threatening effects of CRS without negatively impacting the therapeutic benefits of immunotherapies.

BRIEF SUMMARY OF THE INVENTION

In one aspect, the present invention provides a method of administering a therapeutic protein to a subject in a dosing regimen to mitigate adverse effects of cytokine release syndrome or infusion-related reaction, comprising: (i) administering fractions of a primary dose (D1) of the therapeutic protein in week 1 of the dosing regimen, wherein the primary dose comprises no more than 10 mg of the therapeutic protein, a first dose fraction (F1D1) comprises 40% to 60% of the total primary dose and is administered to the subject on day 1 of week 1, and a second dose fraction (F2D1) comprises the remaining 40% to 60% of the total primary dose and is administered to the subject from 12 to 96 hours following administration of the F1D1; (ii) administering fractions of a secondary dose (D2) of the therapeutic protein in week 2 of the dosing regimen, wherein the secondary dose is no more than one-half of a maximum weekly dose of the therapeutic protein, a first dose fraction (F1D2) comprises 40% to 60% of the total secondary dose, a second dose fraction (F2D2) comprises the remaining 40% to 60% of the total secondary dose, and the F2D2 is administered to the subject from 12 to 96 hours following administration of the F1D2 during week 2 of the dosing regimen; and (iii) administering the maximum weekly dose of the therapeutic protein to the subject as a single dose in a subsequent week of the dosing regimen.

In some cases, the F2D1 is administered to the subject from 24 to 96 hours following administration of the F1D1. In some cases, the F2D1 is administered to the subject from 18 to 72 hours following administration of the F1D1. In some cases, the F2D2 is administered to the subject from 24 to 96 hours following administration of the F1D2. In some cases, the F2D2 is administered to the subject from 18 to 72 hours following administration of the F1D2. In some cases, the subsequent week is week 3 of the dosing regimen. In some cases, the subsequent week is week 4 of the dosing regimen. In some cases, the subsequent week is week 14 of the dosing regimen. In some cases, the subsequent week is any one of weeks 4 to 36 of the dosing regimen.

In some embodiments, the method further comprises: (i) administering fractions of a tertiary dose (D3) of the therapeutic protein in week 3 of the dosing regimen, wherein the tertiary dose is no less than one-half of the maximum weekly dose of the therapeutic protein and no more than the maximum weekly dose of the therapeutic protein, a first dose fraction (F1D3) comprises 40% to 60% of the total tertiary dose, a second dose fraction (F2D3) comprises the remaining 40% to 60% of the total tertiary dose, and the F2D3 is administered to the subject from 12 to 96 hours following administration of the F1D3 during week 3 of the dosing regimen; and (ii) administering the maximum weekly dose of the therapeutic protein to the subject as a single dose in a subsequent week of the dosing regimen.

In some cases, the F2D3 is administered to the subject from 24 to 96 hours following administration of the F1D3. In some cases, the F2D3 is administered to the subject from 18 to 72 hours following administration of the F1D3.

In some cases, the subsequent week is week 4 of the dosing regimen. In some cases, the subsequent week is week 14 of the dosing regimen. In some cases, the subsequent week is any one of weeks 4 to 36 of the dosing regimen. In various embodiments, the tertiary dose is administered as a single dose in weeks 4 to 12 of the dosing regimen.

In one aspect, the present invention provides a method of administering a therapeutic protein to a subject in a dosing regimen to mitigate adverse effects of cytokine release syndrome or infusion-related reaction, comprising: (i) administering fractions of a primary dose (D1) of the therapeutic protein in week 1 of the dosing regimen, wherein the primary dose comprises no more than 10 mg of the therapeutic protein, a first dose fraction (F1D1) comprises 40% to 60% of the total primary dose and is administered to the subject on day 1 of week 1, and a second dose fraction (F2D1) comprises the remaining 40% to 60% of the total primary dose and is administered to the subject from 12 to 96 hours following administration of the F1D1; (ii) administering fractions of a secondary dose (D2) of the therapeutic protein in week 2 of the dosing regimen, wherein the secondary dose is equal to a maximum weekly dose of the therapeutic protein, a first dose fraction (F1D2) comprises 50% of the total secondary dose, a second dose fraction (F2D2) comprises 50% of the total secondary dose, and the F2D2 is administered to the subject from 12 to 96 hours following administration of the F1D2 during week 2 of the dosing regimen; and (iii) administering the maximum weekly dose of the therapeutic protein to the subject as a single dose in a subsequent week of the dosing regimen.

In one aspect, the present invention provides a method of administering a therapeutic protein to a subject in a dosing regimen to mitigate adverse effects of cytokine release syndrome or infusion-related reaction, comprising: (i) administering fractions of a primary dose (D1) of the therapeutic protein in week 1 of the dosing regimen, wherein the primary dose comprises no more than 10 mg of the therapeutic protein, wherein D1 is administered to the subject in multiple dose fractions (e.g., F1D1, F2D1, F3D1, F4D1, F5D1) on subsequent days within week 1; (ii) administering fractions of a secondary dose (D2) of the therapeutic protein in week 2 of the dosing regimen, wherein the secondary dose is equal to or less than a maximum weekly dose of the therapeutic protein, and is administered in multiple fractions (e.g., F1D2, F2D2, F3D2, F4D2, F5D2) to the subject on subsequent days within week 2; and (iii) administering the maximum weekly dose (MD) of the therapeutic protein to the subject as multiple fractions of MD or as a single dose in a subsequent week of the dosing regimen.

In some embodiments, a second dose fraction (F2) is administered to the subject from 12 to 96 (e.g. 24 to 72) hours following administration of the first dose fraction (F1), optionally a third dose fraction (F3) is administered to the subject no less than 24 hours following administration of the second dose fraction (F2), optionally a fourth dose fraction (F4) is administered to the subject no less than 24 hours following administration of the third dose fraction (F3), and optionally a fifth dose fraction (F5) is administered to the subject no less than 24 hours following administration of the fourth dose fraction (F4) during weeks 1, 2 or 3 of the dosing regimen.

In some embodiments, the methods of the present disclosure further comprise administering one or more "maintenance" doses during a maintenance phase of the dosing regimen, which follows completion of a weekly phase of the regimen. In some cases, each maintenance dose is administered 2, 3 or 4 weeks after the immediately preceding dose. In one embodiment, the maintenance dose is the maximum weekly dose of the therapeutic protein administered as a single dose.

In some cases, the maximum weekly dose (MD) of the therapeutic protein is administered to the subject as a single dose for from 1 to 8 weeks, from 1 to 12 weeks, or from 1 to 16 weeks during a weekly phase of the dosing regimen. In some cases, the maximum weekly dose of the therapeutic protein is administered to the subject as a single dose once every two weeks during a maintenance phase of the dosing regimen, which follows completion of a weekly phase of the dosing regimen. In some cases, the maximum weekly dose of the therapeutic protein is administered to the subject as a single dose once every three weeks during a maintenance phase of the dosing regimen, which follows completion of a weekly phase of the dosing regimen. In some cases, the maximum weekly dose of the therapeutic protein is administered to the subject as a single dose once every four weeks during a maintenance phase of the dosing regimen, which follows completion of a weekly phase of the dosing regimen. In some embodiments, the maintenance phase is a period of up to 86 weeks. In some embodiments, the maintenance phase is a period of up to 87 weeks. In some embodiments, the maintenance phase is a period of up to 88 weeks. In some embodiments, the maintenance phase is greater than 86 weeks, greater than 100 weeks, greater than 150 weeks, greater than 200 weeks, or greater than 250 weeks. In some embodiments, the maintenance phase is at least 24 weeks. In some embodiments, the maintenance phase is 24 weeks.

In various embodiments, the primary dose is 1 mg. In various embodiments, the secondary dose is 20 mg. In various embodiments, the tertiary dose is 40 mg. In various embodiments, the tertiary dose is 80 mg. In various embodiments, the tertiary dose is 160 mg. In various embodiments, the tertiary dose is 320 mg.

In various embodiments, the F1D1 comprises 50% of the total primary dose, and the F2D1 comprises 50% of the total primary dose. In various embodiments, the F1D2 comprises 50% of the total secondary dose, and the F2D2 comprises 50% of the total secondary dose. In various embodiments, the F1D3 comprises 50% of the total tertiary dose, and the F2D3 comprises 50% of the total tertiary dose.

In some cases, the maximum weekly dose (MD) of the therapeutic protein is from 5 mg to 320 mg. In various embodiments, the maximum weekly dose of the therapeutic protein is 6-320 mg, 10-320 mg, 5-40 mg, 5-80 mg, 5-160 mg, 12-40 mg, 18-80 mg, 40-80 mg, 80-160 mg, 160-320 mg, 5 mg, 6 mg, 7 mg, 8 mg, 12 mg, 18 mg, 27 mg, 40 mg, 80 mg, 160 mg or 320 mg. In some embodiments, the maximum weekly dose is 80 mg. In some embodiments, the maximum weekly dose is 160 mg. In some embodiments, the maximum weekly dose is 320 mg.

In some cases, maintenance dose of the therapeutic protein is from 5 mg to 320 mg. In various embodiments, the maintenance dose of the therapeutic protein is 6-320 mg, 10-320 mg, 5-40 mg, 5-80 mg, 5-160 mg, 12-40 mg, 18-80 mg, 40-80 mg, 80-160 mg, 160-320 mg, 5 mg, 6 mg, 7 mg, 8 mg, 12 mg, 18 mg, 27 mg, 40 mg, 80 mg, 160 mg or 320 mg. In some embodiments, the maintenance dose is 80 mg. In some embodiments, the maintenance dose is 160 mg. In some embodiments, the maintenance dose is 320 mg.

In some cases, each dose or dose fraction is administered to the subject over a period of from 1 to 6 hours.

In some embodiments, the subject has been diagnosed with a cancer. In some cases, the cancer is a B-cell malignancy. In some cases, the B-cell malignancy is a CD20+ B-cell malignancy. In some cases, the cancer is non-Hodgkin lymphoma, Hodgkin lymphoma, chronic lymphocytic leukemia, acute lymphoblastic leukemia, small lymphocytic lymphoma, diffuse large B-cell lymphoma, follicular lymphoma, mantle cell lymphoma, marginal zone lymphoma, Waldenstrom macroglobulinemia, primary mediastinal B-cell lymphoma, lymphoblastic lymphoma, or Burkitt lymphoma. In some cases, the cancer is selected from pancreatic carcinoma, head and neck cancer, prostate cancer, malignant gliomas, osteosarcoma, colorectal cancer, gastric cancer, malignant mesothelioma, multiple myeloma, ovarian cancer, small cell lung cancer, non-small cell lung cancer, synovial sarcoma, thyroid cancer, breast cancer, melanomaglioma, breast cancer, squamous cell carcinoma, esophageal cancer, clear cell renal cell carcinoma, chromophobe renal cell carcinoma, oncocytoma, transitional cell carcinoma, urothelial carcinoma, bladder adenocarcinoma, or bladder small cell carcinoma. In some embodiments, the subject has been diagnosed with follicular lymphoma (FL). In some cases, the FL is grade 1-3a. In some embodiments, the subject has been diagnosed with diffuse large B-cell lymphoma (DLBCL). In one embodiment, the subject has been diagnosed with relapsed/refractory DLBCL. In some cases, the subject diagnosed with DLBCL has failed prior CAR-T therapy. In some embodiments, the subject has been diagnosed with mantle cell lymphoma (MCL). In some cases, the subject diagnosed with MCL has failed prior Bruton tyrosine kinase (BTK) inhibitor therapy. In some embodiments, the subject has been diagnosed with marginal zone lymphoma (MZL).

In some cases, the subject is a human, a human adult, or a human child (age less than eighteen).

In various embodiments, the therapeutic protein is an antibody or an antigen-binding fragment thereof. In some cases, the antibody is a fully human antibody. In some cases, the antibody is a bispecific antibody or antigen-binding fragment thereof. In some embodiments, the bispecific antibody or antigen-binding fragment comprises a first antigen-binding arm that binds to a T-cell antigen. In some cases, the T-cell antigen is CD3. In some cases, the T-cell antigen is CD28. In some embodiments, the bispecific antibody or antigen-binding fragment comprises a second antigen-binding arm that binds to a tumor cell antigen. In some cases, the tumor cell antigen is selected from the group consisting of AFP, ALK, BAGE proteins, BCMA, BIRC5 (survivin), BIRC7, β-catenin, brc-abl, BRCA1, BORIS, CA9, carbonic anhydrase IX, caspase-8, CALR, CCR5, CD19, CD20 (MS4A1), CD22, CD40, CD70, CDK4, CEA, cyclin-B1, CYP1B1, EGFR, EGFRvIII, ErbB2/Her2, ErbB3, ErbB4, ETV6-AML, EpCAM, EphA2, Fra-1, FOLR1, GAGE proteins (e.g., GAGE-1, -2), GD2, GD3, GloboH, glypican-3, GM3, gp100, Her2, HLA/B-raf, HLA/k-ras, HLA/MAGE-A3, hTERT, LMP2, MAGE proteins (e.g., MAGE-1, -2, -3, -4, -6, and -12), MART-1, mesothelin, ML-IAP, Muc1, Muc2, Muc3, Muc4, Muc5, Muc16 (CA-125), MUM1, NA17, NY-BR1, NY-BR62, NY-BR85, NY-ESO1, p15, p53, PAP, PAX3, PAX5, PCTA-1, PLAC1, PRLR, PRAME, PSMA (FOLH1), RAGE proteins, Ras, RGS5, Rho, SART-1, SART-3, STEAP1, STEAP2, TAG-72, TGF-β, TMPRSS2, Thompson-nouvelle antigen (Tn), TRP-1, TRP-2, tyrosinase, and uroplakin-3.

In some embodiments, the tumor cell antigen is CD20. In some cases, the bispecific antibody is an anti-CD20×anti-CD3 antibody. In some cases, the anti-CD20×anti-CD3 antibody is REGN1979.

In some embodiments, the tumor cell antigen is BCMA. In some cases, the bispecific antibody is an anti-BCMA× anti-CD3 antibody.

In some embodiments, the tumor cell antigen is PSMA. In some cases, the bispecific antibody is an anti-PSMA×anti-CD3 antibody.

In some embodiments, the tumor cell antigen is MUC16. In some cases, the bispecific antibody is an anti-MUC16× anti-CD3 antibody.

In some embodiments, the tumor cell antigen is STEAP2. In some cases, the bispecific antibody is an anti-STEAP2× anti-CD3 antibody.

In various embodiments, the therapeutic protein is maintained at a serum concentration at or above about 2000 micrograms/liter (mcg/L) following administration of the maximum weekly dose for the duration of the dosing regimen. In some cases, the therapeutic protein is maintained at a serum concentration at or above about 2600 mcg/L following administration of the maximum weekly dose for the duration of the dosing regimen. In some embodiments, the therapeutic protein is maintained at a serum concentration at or above about 3700 mcg/L following administration of the maximum weekly dose for the duration of the dosing regimen.

In some embodiments, the therapeutic protein is administered to the subject in combination with a second agent selected from a steroid, an anti-histamine, acetaminophen, a non-steroidal anti-inflammatory drug (NSAID), an IL-6 antagonist, or an IL-6R antagonist. In some cases, the steroid is dexamethasone. In some cases, the NSAID is indomethacin. In some cases, the IL-6 antagonist is an anti-IL-6 antibody, or the IL-6R antagonist is an anti-IL-6R antibody. In some embodiments, the anti-IL-6R antibody is sarilumab. In various embodiments, administration of the second agent is eliminated following a first administration of the maximum weekly dose for the duration of the dosing regimen. In other embodiments, the second agent is administered prior to the administration of the therapeutic protein (e.g., about one to three hours prior to the F1D1, the F2D1, the F1D2, the F2D2, the F1D3 and/or the F2D3). In still other embodiments, the therapeutic protein is administered by infusion over a period of time such as 1, 2, 3, 4, 5, 6, 7, 8, 9, 10, 11, 12, or more hours.

In various embodiments, the therapeutic protein is administered to the subject in combination with a second therapeutic agent. In some embodiments, the second therapeutic agent comprises at least one of rituximab, obinutuzumab, cyclophophamide, doxorubicin, vincristine, prednisone, prednisolone, bendamustine, lenalidomide, chlorambucil, ibritumomab tiuxetan, idelalisib, copanlisib, duvelisib, etoposide, methylprednisolone, cytarabine, cisplatin, mesna, ifosfamide, mitoxantrone, and procarbazine. In some cases, the second therapeutic agent comprises a combination of cyclophosphamide, doxorubicin, vincristine and prednisone. In some cases, the second therapeutic agent comprises a combination of ifosfamide, cisplatin and etoposide. In some cases, the second therapeutic agent comprises a combination of gemcitabine and oxaliplatin. In some cases, the second therapeutic agent comprises a combination of lenalidomide and rituximab. In some cases, the second therapeutic agent is lenalidomide.

In one aspect, the present invention includes a method of treating a B cell cancer in a subject, comprising: (a) selecting a subject diagnosed with a B cell cancer; and (b) administering a therapeutic protein to the subject according to any of the methods discussed above or herein utilizing a dosing regimen to mitigate adverse effects of cytokine release syndrome or infusion-related reaction. In some embodiments, the subject has previously been treated with an anti-CD20 antibody therapy. In some embodiments, the subject has previously been treated with a CAR-T therapy. In some cases, the B cell cancer is selected from the group consisting of follicular lymphoma, diffuse large B-cell lymphoma, mantle cell lymphoma, and marginal zone lymphoma.

In any of the embodiments discussed above or herein, the incidence of grade 3 CRS and IRR is less than 10%. In some cases, the incidence of grade 3 CRS and IRR is less than 7.5% or less than 7%. In some embodiments, the maximum weekly dose is 80 mg or greater when the incidence of CRS and IRR is less than 10%, less than 9%, less than 8%, less than 7.5% or less than 7%. In any of the embodiments, any dose administered as a single dose may be administered in no more than 1 hour.

In various embodiments, any of the features or components of any embodiments discussed above or herein may be combined, and such combinations are encompassed within the scope of the present disclosure. Any specific value discussed above or herein may be combined with another related value discussed above or herein to recite a range with the values representing the upper and lower ends of the range, and such ranges are encompassed within the scope of the present disclosure. A therapeutic protein for use in any of the methods discussed herein, or use of a therapeutic protein in the manufacture of a medicament for use in any of the methods discussed herein are also encompassed within the scope of this disclosure.

Other embodiments will become apparent from a review of the ensuing detailed description.

BRIEF DESCRIPTION OF THE DRAWINGS

FIG. 1 illustrates the incidence of CRS/IRR during the first five weeks of therapy with REGN1979 at various dose levels.

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. The term "about," when used in reference to a particular recited numerical value, means that the value may vary from the recited value by no more than 1%. For example, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

The expression "CD3," refers to an antigen which is expressed on T cells as part of the multimolecular T cell receptor (TCR) and which consists of a homodimer or heterodimer formed from the association of two of four receptor chains: CD3-epsilon, CD3-delta, CD3-zeta, and CD3-gamma. Human CD3-epsilon comprises the amino acid sequence as set forth in SEQ ID NO: 1; human CD3-delta comprises the amino acid sequence as set forth in SEQ ID NO: 2; human CD3-zeta comprises the amino acid sequence as set forth in SEQ ID NO: 3; and CD3-gamma comprises the amino acid sequence as set forth in SEQ ID NO: 4.

All references to proteins, polypeptides and protein fragments herein are intended to refer to the human version of the respective protein, polypeptide or protein fragment unless explicitly specified as being from a non-human species. Thus, the expression "CD3" means human CD3 unless specified as being from a non-human species, e.g., "mouse CD3," "monkey CD3," etc.

"An antigen-binding domain that binds CD3," "an antibody that binds CD3" or an "anti-CD3 antibody" includes antibodies and antigen-binding fragments thereof that specifically recognize a single CD3 subunit (e.g., epsilon, delta, gamma or zeta), as well as antibodies and antigen-binding fragments thereof that specifically recognize a dimeric complex of two CD3 subunits (e.g., gamma/epsilon, delta/epsilon, and zeta/zeta CD3 dimers). The antibodies and antigen-binding fragments of the present invention may bind soluble CD3 and/or cell surface expressed CD3. Soluble CD3 includes natural CD3 proteins as well as recombinant CD3 protein variants such as, e.g., monomeric and dimeric CD3 constructs, that lack a transmembrane domain or are otherwise unassociated with a cell membrane.

The expression "CD20," refers to a non-glycosylated phosphoprotein expressed on the cell membranes of mature B cells. CD20 is considered a B cell tumor-associated antigen because it is expressed by more than 95% of B-cell non-Hodgkin lymphomas (NHLs) and other B-cell malignancies, but it is absent on precursor B-cells, dendritic cells and plasma cells. The human CD20 protein has the amino acid sequence shown in SEQ ID NO: 5.

"An antigen-binding domain that binds CD20," "an antibody that binds CD20" or an "anti-CD20 antibody" includes antibodies and antigen-binding fragments thereof that specifically recognize CD20.

The expression "BCMA," refers to B-cell maturation antigen. BCMA (also known as TNFRSF17 and CD269) is a cell surface protein expressed on malignant plasma cells, and plays a central role in regulating B cell maturation and differentiation into immunoglobulin-producing plasma cells. The amino acid sequence of human BCMA is shown in SEQ ID NO: 6.

"An antigen-binding domain that binds BCMA," "an antibody that binds BCMA" or an "anti-BCMA antibody" includes antibodies and antigen-binding fragments thereof that specifically recognize BCMA.

The expression "PSMA," refers to prostate-specific membrane antigen, also known as folate hydrolase 1 (FOLH1). PSMA is an integral, non-shed membrane glycoprotein that is highly expressed in prostate epithelial cells and is a cell-surface marker for prostate cancer. The amino acid sequence of human PSMA is set forth in SEQ ID NO: 7.

"An antigen-binding domain that binds PSMA," "an antibody that binds PSMA" or an "anti-PSMA antibody"

includes antibodies and antigen-binding fragments thereof that specifically recognize PSMA.

The expression "MUC16," refers to mucin 16. MUC16 is a single transmembrane domain highly glycosylated integral membrane glycoprotein that is highly expressed in ovarian cancer. The amino acid sequence of human MUC16 is set forth in SEQ ID NO: 8.

"An antigen-binding domain that binds MUC16," "an antibody that binds MUC16" or an "anti-MUC16 antibody" includes antibodies and antigen-binding fragments thereof that specifically recognize MUC16.

The expression "STEAP2," refers to six-transmembrane epithelial antigen of prostate 2. STEAP2 is an integral, six-transmembrane-spanning protein that is highly expressed in prostate epithelial cells and is a cell-surface marker for prostate cancer. STEAP2 is a 490-amino acid protein encoded by STEAP2 gene located at the chromosomal region 7q21 in humans. The amino acid sequence of human STEAP2 is set forth in SEQ ID NO: 9.

"An antigen-binding domain that binds STEAP2," "an antibody that binds STEAP2" or an "anti-STEAP2 antibody" includes antibodies and antigen-binding fragments thereof that specifically recognize STEAP2.

The term "therapeutic protein," includes any polypeptide, including antibodies and antigen-binding fragments thereof, and bispecific antibodies and antigen-binding fragments thereof, which is used to prevent, treat or ameliorate any condition, disease or disorder in a subject.

The term "antigen-binding molecule" includes antibodies and antigen-binding fragments of antibodies, including, e.g., bispecific antibodies.

The term "antibody", means any antigen-binding molecule or molecular complex comprising at least one complementarity determining region (CDR) that specifically binds to or interacts with a particular antigen (e.g., CD20, BCMA, PSMA, MUC16, STEAP2 or CD3). The term "antibody" includes immunoglobulin molecules comprising four polypeptide chains, two heavy (H) chains and two light (L) chains inter-connected by disulfide bonds, as well as multimers thereof (e.g., IgM). The term "antibody" also includes immunoglobulin molecules consisting of four polypeptide chains, two heavy (H) chains and two light (L) chains inter-connected by disulfide bonds. Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the antibody (or antigen-binding portion thereof) may be identical to the human germline sequences, or may be naturally or artificially modified. An amino acid consensus sequence may be defined based on a side-by-side analysis of two or more CDRs. The term "antibody" includes a "bispecific antibody" unless otherwise noted.

The term "antibody", also includes antigen-binding fragments of full antibody molecules. The terms "antigen-binding portion" of an antibody, "antigen-binding fragment" of an antibody, and the like, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

The expression "bispecific antigen-binding molecule" refers to a protein, polypeptide or molecular complex comprising at least a first antigen-binding domain and a second antigen-binding domain. Each antigen-binding domain within the bispecific antigen-binding molecule comprises at least one CDR that alone, or in combination with one or more additional CDRs and/or FRs, specifically binds to a particular antigen. Bispecific antigen-binding molecules include bispecific antibodies.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment".

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; $V_H$-$C_L$; $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The antibodies of the present invention may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) Proc. Natl. Acad. Sci. (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity. Antibodies of the present disclosure may include a human IgG heavy chain. In various embodiments, the heavy may be of IgG1, IgG2, IgG3 or IgG4 isotype.

In certain embodiments of the invention, the antibodies or bispecific antibodies are human antibodies. The term "human antibody" is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody" is not intended to include antibodies in which CDR sequences derived from the germline of another mammalian species, such as a mouse, have been grafted onto human framework sequences.

The antibodies of the invention may, in some embodiments, be recombinant human antibodies. The term "recombinant human antibody" is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

The antibodies of the invention may be isolated antibodies. An "isolated antibody" means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The antibodies discussed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes antibodies comprising variants of any of the HCVR, LCVR, and/or CDR amino acid sequences disclosed herein having one or more conservative substitutions. For example, the present invention includes antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth herein, the anti-CD3 antibodies disclosed in WO 2014/047231 or WO 2017/053856, the bispecific anti-CD20×anti-CD3 antibodies disclosed in WO 2014/047231, the anti-PSMA or anti-PSMA×anti-CD3 antibodies disclosed in WO 2017/023761, the anti-MUC16 or anti-MUC16×anti-CD3 antibodies disclosed in WO 2018/067331, the anti-STEAP2 or anti-STEAP2×anti-CD3 antibodies disclosed in WO 2018/058001, or the anti-BCMA or anti-BCMA×anti-CD3 antibodies disclosed in U.S. 62/700,596 (filed Jul. 19, 2018), each of which is incorporated herein by reference.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

Dosing Strategies and Administration Regimens

Dosing strategies were created that provide administration regimens to mitigate the prevalence or severity, or both, of cytokine release syndrome (CRS) or infusion-related reaction (IRR) by administration of a therapeutic protein to a patient for various therapies. According to certain embodiments of the present invention, these strategies include multiple doses of a therapeutic protein or an antigen-binding molecule (e.g., an antibody or a bispecific antibody) that may be administered to a subject over a defined time course to create a regimen. The methods according to this aspect of the invention comprise sequentially administering to a subject multiple doses of a therapeutic protein of the invention. "Sequentially administering" means that each dose of a therapeutic protein is administered to the subject at a different point in time, e.g., on different days separated by a predetermined interval (e.g., hours, days, weeks or months). The present invention includes methods which comprise sequentially administering to the patient a split primary dose of a therapeutic protein, followed by a split secondary dose of the therapeutic protein, optionally followed by a split tertiary dose of the therapeutic protein, followed by single doses of a maximum weekly dose of the therapeutic protein. The present administration regimens allow for higher doses of the therapeutic protein that are desirable for enhancing therapeutic efficacy, but without the deleterious effects associated with CRS or IRR. Without intending to be bound by any particular theory, the present administration regimens provide for priming of the immune response to administration of the therapeutic protein to minimize the incidence and severity of CRS and IRR during initial phases of the treatment regimen, which then permits administration of higher doses of the therapeutic proteins during subsequent phases of the treatment regimen without significant adverse events associated with CRS or IRR.

An exemplary administration regimen includes: (i) administering fractions of a primary dose of the therapeutic protein in week 1 (W1) of the dosing regimen, wherein the primary dose comprises no more than 1 mg of the therapeutic protein, a first dose fraction (F1D1) comprises 50% of the primary dose and is administered to the subject on day 1 of week 1, and a second dose fraction (F2D1) comprises 50% of the total primary dose and is administered to the subject within 96 hours following administration of the F1D1; (ii) administering fractions of a secondary dose of the therapeutic protein in week 2 (W2) of the dosing regimen, wherein the secondary dose is no more than one-half of a maximum weekly dose of the therapeutic protein, a first dose fraction (F1D2) comprises 50% of the secondary dose, a second dose fraction (F2D2) comprises 50% of the secondary dose, and the F1D2 and the F2D2 are administered to the subject within 96 hours of one another during week 2 of the dosing regimen; and (iii) administering the maximum weekly dose of the therapeutic protein to the subject as a single dose in a subsequent week (Ws) of the dosing regimen.

Another exemplary administration regimen includes: (i) administering fractions of a primary dose of the therapeutic protein in week 1 (W1) of the dosing regimen, wherein the primary dose comprises no more than 1 mg of the therapeutic protein, a first dose fraction (F1D1) comprises 50% of the primary dose and is administered to the subject on day 1 of week 1, and a second dose fraction (F2D1) comprises 50% of the total primary dose and is administered to the subject within 96 hours following administration of the F1D1; (ii) administering fractions of a secondary dose of the therapeutic protein in week 2 (W2) of the dosing regimen, wherein the secondary dose is no more than one-half of a maximum weekly dose of the therapeutic protein, a first dose fraction (F1D2) comprises 50% of the secondary dose, a second dose fraction (F2D2) comprises 50% of the secondary dose, and the F1D2 and the F2D2 are administered to the subject within 96 hours of one another during week 2 of the dosing regimen; (iii) administering fractions of a tertiary dose of the therapeutic protein in week 3 (W3) of the dosing regimen, wherein the tertiary dose is no less than one-half of the maximum weekly dose of the therapeutic protein and no more than the maximum weekly dose of the therapeutic protein, a first dose fraction (F1D3) comprises 50% of the tertiary dose, a second dose fraction (F2D3) comprises 50% of the tertiary dose, and the F1D3 and the F2D3 are administered to the subject within 96 hours of one another during week 3 of the dosing regimen; and (iv) administering the maximum weekly dose of the therapeutic protein to the subject as a single dose in a subsequent week (Ws) of the dosing regimen.

In various embodiments, the primary dose of the therapeutic protein can range from 0.1 mg to 10 mg or more. In some cases, the primary dose of the therapeutic protein is from 0.5 mg to 10 mg, from 1-10 mg, from 2-5 mg, or from 5-10 mg. In some cases, the primary dose of the therapeutic protein is 0.5, 1, 1.5, 2, 2.5, 3, 3.5, 4, 4.5, 5, 5.5, 6, 6.5, 7, 7.5, 8, 8.5, 9, 9.5 or 10 mg. In various embodiments, the primary dose of the therapeutic protein comprises a range including any of the values noted above as the upper or lower end of the range (e.g., 1-5 mg)

In various embodiments, the maximum weekly dose of the therapeutic protein is from 5 mg to 320 mg. In some embodiments, the maximum weekly dose of the therapeutic protein is from greater than 5 mg up to 320 mg. In some cases, the maximum weekly dose of the therapeutic protein is 6-320 mg, 10-320 mg, 5-40 mg, 5-80 mg, 5-160 mg, 12-40 mg, 18-80 mg, 40-80 mg, 80- 160 mg, 160-320 mg, 5 mg, 6 mg, 7 mg, 8 mg, 12 mg, 18 mg, 27 mg, 40 mg, 80 mg, 160 mg or 320 mg. In some cases, the maximum weekly dose of the therapeutic protein is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, or 320 mg. In various embodiments, the maximum weekly dose of the therapeutic protein comprises a range including any of the values noted above as the upper or lower end of the range (e.g., 200-300 mg).

In various embodiments, the secondary dose comprises 50% of the maximum weekly dose of the therapeutic protein. In some cases, the secondary dose comprises 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, or 10% of the maximum weekly dose of the therapeutic protein. In some cases, the secondary dose of the therapeutic protein comprises a percentage range of the maximum weekly dose including any of the values noted above as the upper or lower end of the range (e.g., 35-50%).

In various embodiments, the tertiary dose comprises 50% of the maximum weekly dose of the therapeutic protein. In some cases, the tertiary dose comprises 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, or 90% of the maximum weekly dose of the therapeutic protein. In some cases, the tertiary dose of the therapeutic protein comprises a percentage range of the maximum weekly dose including any of the values noted above as the upper or lower end of the range (e.g., 50-75%).

In various embodiments, the first dose fraction and the second dose fraction of the primary, secondary, and/or tertiary doses each comprise 50% of the dose. In some cases, the first dose fraction and the second dose fraction of the primary, secondary, and/or tertiary doses comprise different percentages (totaling 100%) of the total dose. For example, the first dose fraction may comprise 45% of the dose, and the second dose fraction may comprise 55% of the dose. Alternatively, the first dose fraction may comprise 55% of the dose, and the second dose fraction may comprise 45% of the dose. In various embodiments, the first and second dose fractions may include 10%/90%, 15%/85%, 20%/80%, 25%/75%, 30%/70%, 35%/65%, 40%/60%, 46%/54%, 47%/53%, 48%/52%, 49%/51%, or vice versa, of the total primary, secondary, or tertiary dose, respectively.

In various embodiments, the primary, secondary and/or tertiary doses (D1, D2 and/or D3) can be split into two or more fractions. Various options for splitting the doses into two fractions are discussed above. In some cases, however, the doses are split into 3, 4 or 5 fractions. For example, the primary dose could be split into 5 fractions, each comprising 20% of the total primary dose, and each dose fraction (F1D1, F2D1, F3D1, F4D1, and F5D1) can be administered to the subject on five consecutive days during the first week of the administration regimen. In other cases, the percentage of the total dose (e.g., the primary dose) may vary among each dose fraction. For example, if the primary dose is split into 3 fractions, the first dose fraction (F1D1) may include 30% of the total primary dose, the second dose fraction (F2D1) may include 30% of the total primary dose, and the third dose fraction (F3D1) may include the remaining 40% of the total primary dose. Other combinations of the percentages and number of fractional doses that equal 100% of the total dose are expressly contemplated herein.

In one exemplary embodiment of the dosing regimen, the primary dose comprises 1 mg, each of the first dose fraction (F1D1) and the second dose fraction (F2D1) comprises 500 mcg, the secondary dose comprises 6 mg, each of the first dose fraction (F1D2) and the second dose fraction (F2D2) comprise 3 mg, the tertiary dose comprises 12 mg, each of the first dose fraction (F1D3) and the second dose fraction F2D3) comprise 6 mg, and the maximum weekly dose comprises 12 mg of the therapeutic protein.

In one exemplary embodiment of the dosing regimen, the primary dose comprises 1 mg, each of the first dose fraction (F1D1) and the second dose fraction (F2D1) comprises 500 mcg, the secondary dose comprises 9 mg, each of the first dose fraction (F1D2) and the second dose fraction (F2D2) comprise 4.5 mg, the tertiary dose comprises 18 mg, each of the first dose fraction (F1D3) and the second dose fraction F2D3) comprise 9 mg, and the maximum weekly dose comprises 18 mg of the therapeutic protein.

In one exemplary embodiment of the dosing regimen, the primary dose comprises 1 mg, each of the first dose fraction (F1D1) and the second dose fraction (F2D1) comprises 500 mcg, the secondary dose comprises 13.5 mg, each of the first dose fraction (F1D2) and the second dose fraction (F2D2) comprise 6.75 mg, the tertiary dose comprises 27 mg, each of the first dose fraction (F1D3) and the second dose fraction F2D3) comprise 13.5 mg, and the maximum weekly dose comprises 27 mg of the therapeutic protein.

In one exemplary embodiment of the dosing regimen, the primary dose comprises 1 mg, each of the first dose fraction (F1D1) and the second dose fraction (F2D1) comprises 500 mcg, the secondary dose comprises 20 mg, each of the first dose fraction (F1D2) and the second dose fraction (F2D2) comprise 10 mg, the tertiary dose comprises 40 mg, each of the first dose fraction (F1D3) and the second dose fraction F2D3) comprise 20 mg, and the maximum weekly dose comprises 40 mg of the therapeutic protein.

In one exemplary embodiment of the dosing regimen, the primary dose comprises 1 mg, each of the first dose fraction (F1D1) and the second dose fraction (F2D1) comprises 500 mcg, the secondary dose comprises 20 mg, each of the first dose fraction (F1D2) and the second dose fraction (F2D2) comprise 10 mg, the tertiary dose comprises 60 mg, each of the first dose fraction (F1D3) and the second dose fraction F2D3) comprise 30 mg, and the maximum weekly dose comprises 80 mg of the therapeutic protein.

In one exemplary embodiment of the dosing regimen, the primary dose comprises 1 mg, each of the first dose fraction (F1D1) and the second dose fraction (F2D1) comprises 500 mcg, the secondary dose comprises 20 mg, each of the first dose fraction (F1D2) and the second dose fraction (F2D2) comprise 10 mg, the tertiary dose comprises 80 mg, each of the first dose fraction (F1D3) and the second dose fraction F2D3) comprise 40 mg, and the maximum weekly dose comprises 160 mg of the therapeutic protein.

In one exemplary embodiment of the dosing regimen, the primary dose comprises 1 mg, each of the first dose fraction (F1D1) and the second dose fraction (F2D1) comprises 500 mcg, the secondary dose comprises 20 mg, each of the first dose fraction (F1D2) and the second dose fraction (F2D2) comprise 10 mg, the tertiary dose comprises 120 mg, each of the first dose fraction (F1D3) and the second dose fraction F2D3) comprise 60 mg, and the maximum weekly dose comprises 240 mg of the therapeutic protein.

In one exemplary embodiment of the dosing regimen, the primary dose comprises 1 mg, each of the first dose fraction (F1D1) and the second dose fraction (F2D1) comprises 500 mcg, the secondary dose comprises 20 mg, each of the first dose fraction (F1D2) and the second dose fraction (F2D2) comprise 10 mg, the tertiary dose comprises 160 mg, each of the first dose fraction (F1D3) and the second dose fraction F2D3) comprise 80 mg, and the maximum weekly dose comprises 320 mg of the therapeutic protein.

In one exemplary embodiment of the dosing regimen, the primary dose (D1) comprises 1 mg, each of the first dose fraction (F1D1) and the second dose fraction (F2D2) of the primary dose comprises 500 mcg, the secondary dose (D2) comprises 3 mg, each of the first dose fraction (F1D2) and the second dose fraction (F2D2) of the secondary dose comprises 1.5 mg, and the maximum weekly dose comprises 3 mg of the therapeutic protein.

In one exemplary embodiment of the dosing regimen, the primary dose (D1) comprises 3 mg, each of the first dose fraction (F1D1) and the second dose fraction (F2D2) of the primary dose comprises 1.5 mg, the secondary dose (D2) comprises 9 mg, each of the first dose fraction (F1D2) and the second dose fraction (F2D2) of the secondary dose comprises 4.5 mg, and the maximum weekly dose comprises 9 mg of the therapeutic protein.

In one exemplary embodiment of the dosing regimen, the primary dose (D1) comprises 5 mg, each of the first dose fraction (F1D1) and the second dose fraction (F2D2) of the primary dose comprises 2.5 mg, the secondary dose (D2) comprises 15 mg, each of the first dose fraction (F1D2) and the second dose fraction (F2D2) of the secondary dose comprises 7.5 mg, and the maximum weekly dose comprises 15 mg of the therapeutic protein.

In one exemplary embodiment of the dosing regimen, the primary dose (D1) comprises 10 mg, each of the first dose fraction (F1D1) and the second dose fraction (F2D2) of the primary dose comprises 5 mg, the secondary dose (D2) comprises 30 mg, each of the first dose fraction (F1D2) and the second dose fraction (F2D2) of the secondary dose comprises 15 mg, and the maximum weekly dose comprises 30 mg of the therapeutic protein.

In various embodiments, the therapeutic protein is administered at a dose to maintain a serum concentration of at least about 2000 mcg/L following administration of the maximum weekly dose for the duration of the dosing regimen. In some cases, the therapeutic protein is administered at a dose to maintain a serum concentration of at least about 2100, 2200, 2300, 2400, 2500, 2600, 2700, 2800, 2900, 3000, 3100, 3200, 3300, 3400, or 3500 mcg/L following administration of the maximum weekly dose for the duration of the dosing regimen.

In various embodiments, the therapeutic protein is administered at a dose to maintain an average serum concentration of at least about 2600 mcg/L following administration of the maximum weekly dose for the duration of the dosing regimen. In some cases, the therapeutic protein is administered at a dose to maintain an average serum concentration of at least about 2000, 2100, 2200, 2300, 2400, 2500, 2700, 2800, 2900, 3000, 3100, 3200, 3300, 3400, 3500, 3600, 3700, 3800, 3900 or 4000 mcg/L following administration of the maximum weekly dose for the duration of the dosing regimen.

In various embodiments, the subsequent week (Ws) of the dosing regimen is week 3 (W3), week 4 (W4), week 5 (W5), week 6 (W6), week 7 (W7), week 8 (W8), week 9 (W9), week 10 (W10), week 11 (W11), week 12 (W12), week 13 (W13), week 14 (W14), week 15 (W15), week 16 (W16), week 17 (W17), week 18 (W18), week 19 (W19), week 20 (W20), week 21 (W21), week 22 (W22), week 23 (W23), week 24 (W24), week 25 (W25), week 26 (W26), week 27 (W27), week 28 (W29), week 30 (W30), week 31 (31), week 32 (32), week 33 (33), week 34 (W34), week 35 (W35), or week 36 (W36).

In various embodiments, the second fractional dose in any given week of the dosing regimen is administered within 24, 36, 48, 60, 72, 84 or 96 hours following administration of the first fractional dose.

In various embodiments, the maximum weekly dose of the therapeutic protein is administered to the subject as a single dose for from 1 to 8 weeks, or for 1, 2, 3, 4, 5, 6, 7, 8, 9, 10, 11, 12, 13, 14, 15, 16, 17, 18, 19, 20, 21, 22, 23, 24, 25, 26 or more weeks during a weekly phase of the dosing regimen. In some cases, the maximum weekly dose of the therapeutic protein is administered to the subject as a single dose over a range of weeks including any of the values noted above as the upper or lower end of the range (e.g., 1-12 weeks).

In various embodiments, the maximum weekly dose of the therapeutic protein is administered to the subject as a single dose (maintenance dose) once every two weeks for up to 24 weeks, or for up to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 95, 100, 110, 120, 130, 140, 150, 160, 170, 180, 190, 200, 210, 220, 230, 240, 250, 260 or more weeks during a biweekly, triweekly, tetraweekly, or pentaweekly phase (maintenance phase) of the dosing regimen, which may follow completion of the weekly phase of the dosing regimen (i.e., either the weekly dosing of the maximum weekly dose or the split dosing of the primary, secondary and (optionally) tertiary doses. In some cases, the maximum weekly dose of the therapeutic protein is administered to the subject as a single dose (maintenance dose) once every two weeks, one every three weeks, or once every four weeks over a range of weeks including any of the values noted above as the upper or lower end of the range (e.g., 24-86 weeks).

In one exemplary embodiment of the dosing regimen, the primary dose comprises 1 mg, each of the first dose fraction (F1D1) and the second dose fraction (F2D1) comprises 500 mcg, the secondary dose comprises 20 mg, each of the first dose fraction (F1D2) and the second dose fraction (F2D2) comprise 10 mg, the tertiary dose comprises 80 mg, each of the first dose fraction (F1D3) and the second dose fraction F2D3) comprise 40 mg, and the maximum weekly dose comprises 160 mg of the therapeutic protein, wherein the tertiary dose is administered as a single dose (i.e., 80 mg) weekly (QW) during weeks 4 to 12 of the dosing regimen, and the maximum weekly dose is administered as a single dose (i.e., 160 mg) once every two weeks (Q2W) from week 14 onwards of the dosing regimen.

In some cases, the above-identified dosing regimen is for use in methods of treating an aggressive lymphoma (e.g., mantle cell lymphoma or marginal zone lymphoma).

In one exemplary embodiment of the dosing regimen, the primary dose comprises 1 mg, each of the first dose fraction (F1D1) and the second dose fraction (F2D1) comprises 500 mcg, the secondary dose comprises 20 mg, each of the first dose fraction (F1D2) and the second dose fraction (F2D2) comprise 10 mg, the tertiary dose comprises 160 mg, each of the first dose fraction (F1D3) and the second dose fraction F2D3) comprise 80 mg, and the maximum weekly dose comprises 320 mg of the therapeutic protein, wherein the tertiary dose is administered as a single dose (i.e., 160 mg) weekly (QW) during weeks 4 to 12 of the dosing regimen, and the maximum weekly dose is administered as a single dose (i.e., 320 mg) once every two weeks (Q2W) from week 14 onwards of the dosing regimen.

In some cases, the above-identified dosing regimen is for use in methods of treating an aggressive lymphoma (e.g., mantle cell lymphoma or marginal zone lymphoma). In some cases, the above-identified dosing regimen is for use in methods of treating follicular lymphoma (e.g., grade 1-3a). In some cases, the above-identified dosing regimen is for treating diffuse large B cell lymphoma (including relapsed or refractory DLBCL, e.g., in patients that have failed prior CAR-T therapy).

In various embodiments, each dose or fractional dose of the therapeutic protein is administered to the subject over a period of from 1-4, 1-5, or 1-6 hours (e.g., via infusion). In some cases, the dose or fractional dose is administered over a period of 1, 2, 3, 4, 5, 6, 7, 8, 9, 10, 11 or 12 or more hours. In some cases, each dose or fractional dose of the therapeutic protein is administered to the subject over a range of time including any of the values noted above as the upper or lower end of the range (e.g., 1-8 hours). In various embodiments, each maximum weekly dose is administered as a single infusion.

In some embodiments of the administration regimens discussed herein, a second agent is administered as a pre-treatment, or in combination with, the therapeutic protein. In some cases, a steroid, such as dexamethasone, is administered to the patient as a pretreatment prior to administration of the primary fractional doses and the secondary fractional doses, and optionally prior to the tertiary fractional doses. In some embodiments, the dexamethasone is administered to the patient about one to three hours prior to the first dose fraction (F1D1). In certain embodiments the dexamethasone dose is administered by intravenous infusion. In some cases, a cytokine antagonist, such an anti-IL-6 antibody or an anti-IL-6R antibody is administered in combination with the therapeutic protein during the primary, secondary, and optionally the tertiary dose administrations. In some cases, an anti-CD20 monospecific antibody (e.g., rituximab) is administered to the patient as a pretreatment prior to administration of the primary fractional doses and optionally the secondary fractional doses, and optionally prior to the tertiary fractional doses. These pretreatment or combination administrations of the second agent are discontinued, in an embodiment, with the single dose administration of the maximum weekly dose beginning at, e.g., week 3, week 4, week 5 or week 6 of the dosing regimen so as to not artificially dampen cytokine activity and thereby impede the therapeutic effects of the therapeutic protein.

The terms "primary dose," "secondary dose," and "tertiary doses," refer to the temporal sequence of administration of the antigen-binding molecule of the invention. Thus, the "primary dose" is the dose which is administered at the beginning of the treatment regimen; the "secondary dose" is the dose which is administered after the primary dose (including all dose fractions of the primary dose); and the "tertiary doses" are the doses which are administered after the secondary dose (including all dose fractions of the secondary dose). The primary, secondary, and tertiary doses (or their dose fractions) may contain an amount of the therapeutic protein as discussed herein. In some cases, the "primary dose" and "secondary dose," as well as the optional "tertiary dose" may be referred to as "loading doses," while the subsequent maximum weekly doses may be referred to as "maintenance doses". In some cases, the "primary dose" may be referred to as the "initial dose." In some cases, the "secondary dose" may be referred to as the "intermediate dose." In some cases, the "tertiary dose" may be referred to as the "step-up dose."

The phrase "the immediately preceding dose," refers to, in a sequence of multiple administrations, the dose of antigen-binding molecule which is administered to a patient prior to the administration of the very next dose in the sequence with no intervening doses.

Antigen-Binding Molecules

The antibodies for use in connection with the present invention may be monospecific, bi-specific, or multispecific. Multispecific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The antibodies and bispecific antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second or additional binding specificity.

The present invention includes antibodies having the HCVR, LCVR and/or CDR amino acid sequences of the antibodies set forth herein, the anti-CD3 antibodies disclosed in WO 2014/047231 or WO 2017/053856, the bispecific anti-CD20×anti-CD3 antibodies disclosed in WO 2014/047231, the anti-PSMA or anti-PSMA×anti-CD3 antibodies disclosed in WO 2017/023761, the anti-MUC16 or anti-MUC16×anti-CD3 antibodies disclosed in WO 2018/067331, the anti-STEAP2 or anti-STEAP2×anti-CD3 antibodies disclosed in WO 2018/058001, or the anti-BCMA or anti-BCMA×anti-CD3 antibodies disclosed in U.S. 62/700,596 (filed Jul. 19, 2018), each of which is incorporated herein by reference.

Use of the expression "anti-CD3 antibody," "anti-CD20 antibody," "anti-PSMA antibody," anti-MUC16 antibody," "anti-STEAP2 antibody," "anti-BCMA antibody," or the like herein is intended to include both monospecific antibodies as well as bispecific antibodies comprising the respective antigen-binding arm (e.g., CD3). Thus, the present invention includes bispecific antibodies wherein one arm of an immunoglobulin binds human CD3, and the other arm of the immunoglobulin is specific for, e.g., human CD20, human PSMA, human MUC16, human STEAP2, or human BCMA.

In certain embodiments, the CD3-binding arm binds to human CD3 and induces human T cell activation. In certain embodiments, the CD3-binding arm binds weakly to human CD3 and induces human T cell activation. In other embodiments, the CD3-binding arm binds weakly to human CD3 and induces tumor-associated antigen-expressing cell killing in the context of a bispecific or multispecific antibody. In other embodiments, the CD3-binding arm binds or associates weakly with human and cynomolgus (monkey) CD3, yet the binding interaction is not detectable by in vitro assays known in the art. In certain embodiments, the bispecific antibodies or antigen-binding fragments for use in the present invention comprise an antigen-binding arm that binds to CD28, ICOS, HVEM, CD27, 4-1BB, OX40, DR3, GITR, CD30, SLAM, CD2, 2B4, CD226, TIM1, or TIM2 to induce T cell activation.

In certain exemplary embodiments of the present invention, the bispecific antigen-binding molecule is a bispecific antibody. Each antigen-binding domain of a bispecific antibody comprises a heavy chain variable domain (HCVR) and a light chain variable domain (LCVR). In the context of a bispecific antigen-binding molecule comprising a first and a second antigen-binding domain (e.g., a bispecific antibody), the CDRs of the first antigen-binding domain may be designated with the prefix "A1" and the CDRs of the second antigen-binding domain may be designated with the prefix "A2". Thus, the CDRs of the first antigen-binding domain may be referred to herein as A1-HCDR1, A1-HCDR2, and A1-HCDR3; and the CDRs of the second antigen-binding domain may be referred to herein as A2-HCDR1, A2-HCDR2, and A2-HCDR3.

In one embodiment, the therapeutic protein is a bispecific anti-CD20×anti-CD3 antibody known as REGN1979. REGN1979 comprises an anti-CD20 binding arm comprising a heavy chain comprising the amino acid sequence of SEQ ID NO: 10, an anti-CD3 binding arm comprising a heavy chain comprising the amino acid sequence of SEQ ID NO: 11, and a common light chain (corresponding to both the anti-CD20 and anti-CD3 binding arms) comprising the amino acid sequence of SEQ ID NO: 12. In some cases, the mature form of the antibody may not include the C-terminal lysine residues of SEQ ID NOs: 10 and 11. Thus, in some cases the anti-CD20 binding arm of REGN1979 comprises a heavy chain comprising residues 1-452 of SEQ ID NO: 10, and the anti-CD3 binding arm of REGN1979 comprises a heavy chain comprising residues 1-448 of SEQ ID NO: 11. REGN1979 also comprises the HCVR, LCVR and CDR sequences set forth in the accompanying sequence listing. The anti-CD20 HCVR corresponds to SEQ ID NO: 13, the anti-CD3 HCVR corresponds to SEQ ID NO: 14, and the common LCVR corresponds to SEQ ID NO: 15. The anti-CD20 HCDR1-HCDR2-HCDR3 domains correspond to SEQ ID NOs: 16-17-18, respectively. The anti-CD3 HCDR1-HCDR2-HCDR3 domains correspond to SEQ ID NOs: 19-20-21, respectively. The common LCDR1-LCDR2-LCDR3 domains correspond to SEQ ID NOs: 22-23-24, respectively.

The bispecific antigen-binding molecules discussed above or herein may be bispecific antibodies. In some cases, the bispecific antibody comprises a human IgG heavy chain constant region. In some cases, the human IgG heavy chain constant region is isotype IgG1. In some cases, the human IgG heavy chain constant region is isotype IgG4. In various embodiments, the bispecific antibody comprises a chimeric hinge that reduces Fcγ receptor binding relative to a wild-type hinge of the same isotype. In some cases, the bispecific antigen-binding molecules of the present invention comprise any one of the formats discussed in Brinkmann et al., *MABS,* 9(2):182-212, 2017, which is incorporated herein by reference.

The first antigen-binding domain and the second antigen-binding domain may be directly or indirectly connected to one another to form a bispecific antigen-binding molecule of the present invention. Alternatively, the first antigen-binding domain and the second antigen-binding domain may each be connected to a separate multimerizing domain. The association of one multimerizing domain with another multimerizing domain facilitates the association between the two antigen-binding domains, thereby forming a bispecific antigen-binding molecule. A "multimerizing domain" is any macromolecule, protein, polypeptide, peptide, or amino acid that has the ability to associate with a second multimerizing domain of the same or similar structure or constitution. For example, a multimerizing domain may be a polypeptide comprising an immunoglobulin $C_H3$ domain. A non-limiting example of a multimerizing component is an Fc portion of an immunoglobulin (comprising a $C_H2$-$C_H3$ domain), e.g., an Fc domain of an IgG selected from the isotypes IgG1, IgG2, IgG3, and IgG4, as well as any allotype within each isotype group.

Bispecific antigen-binding molecules of the present invention will typically comprise two multimerizing domains, e.g., two Fc domains that are each individually part of a separate antibody heavy chain. The first and second multimerizing domains may be of the same IgG isotype such as, e.g., IgG1/IgG1, IgG2/IgG2, IgG4/IgG4. Alternatively, the first and second multimerizing domains may be of different IgG isotypes such as, e.g., IgG1/IgG2, IgG1/IgG4, IgG2/IgG4, etc.

In certain embodiments, the multimerizing domain is an Fc fragment or an amino acid sequence of from 1 to about 200 amino acids in length containing at least one cysteine residue. In other embodiments, the multimerizing domain is a cysteine residue, or a short cysteine-containing peptide. Other multimerizing domains include peptides or polypeptides comprising or consisting of a leucine zipper, a helix-loop motif, or a coiled-coil motif.

Any bispecific antibody format or technology may be used to make the bispecific antigen-binding molecules of the present invention. For example, an antibody or fragment thereof having a first antigen binding specificity can be functionally linked (e.g., by chemical coupling, genetic fusion, noncovalent association or otherwise) to one or more other molecular entities, such as another antibody or antibody fragment having a second antigen-binding specificity to produce a bispecific antigen-binding molecule. Specific exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED)body, leucine zipper, Duobody, IgG1/IgG2, dual acting Fab (DAF)-IgG, and $Mab^2$ bispecific formats (see, e.g., Klein et al. 2012, mAbs 4:6, 1-11, and references cited therein, for a review of the foregoing formats).

In the context of bispecific antigen-binding molecules of the present invention, the multimerizing domains, e.g., Fc domains, may comprise one or more amino acid changes (e.g., insertions, deletions or substitutions) as compared to the wild-type, naturally occurring version of the Fc domain. For example, the invention includes bispecific antigen-binding molecules comprising one or more modifications in the Fc domain that results in a modified Fc domain having a modified binding interaction (e.g., enhanced or diminished) between Fc and FcRn. In one embodiment, the bispecific antigen-binding molecule comprises a modification in a $C_H2$ or a $C_H3$ region, wherein the modification increases the affinity of the Fc domain to FcRn in an acidic environment (e.g., in an endosome where pH ranges from about 5.5 to about 6.0). Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

The present invention also includes bispecific antigen-binding molecules comprising a first $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). See, for example, U.S. Pat. No. 8,586,713. Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies.

In certain embodiments, the Fc domain may be chimeric, combining Fc sequences derived from more than one immunoglobulin isotype. For example, a chimeric Fc domain can comprise part or all of a $C_H2$ sequence derived from a human IgG1, human IgG2 or human IgG4 $C_H2$ region, and part or all of a $C_H3$ sequence derived from a human IgG1, human IgG2 or human IgG4. A chimeric Fc domain can also contain a chimeric hinge region. For example, a chimeric hinge may comprise an "upper hinge" sequence, derived from a human IgG1, a human IgG2 or a human IgG4 hinge region, combined with a "lower hinge" sequence, derived from a human IgG1, a human IgG2 or a human IgG4 hinge region. A particular example of a chimeric Fc domain that can be included in any of the antigen-binding molecules set forth herein comprises, from N- to C-terminus: [IgG4 $C_H1$]-[IgG4 upper hinge]-[IgG2 lower hinge]-[IgG4 $C_H2$]-[IgG4 $C_H3$]. Another example of a chimeric Fc domain that can be included in any of the antigen-binding molecules set forth herein comprises, from N- to C-terminus: [IgG1 $C_H1$]-[IgG1 upper hinge]-[IgG2 lower hinge]-[IgG4 $C_H2$]-[IgG1 $C_H3$]. These and other examples of chimeric Fc domains that can be included in any of the antigen-binding molecules of the present invention are described in US Publication 2014/0243504, published Aug. 28, 2014, which is herein incorporated in its entirety. Chimeric Fc domains having these general structural arrangements, and variants thereof, can have altered Fc receptor binding, which in turn affects Fc effector function.

Binding Properties of the Antigen-Binding Molecules

The term "binding" in the context of the binding of an antibody, immunoglobulin, antibody-binding fragment, or Fc-containing protein to either, e.g., a predetermined antigen, such as a cell surface protein or fragment thereof, typically refers to an interaction or association between a minimum of two entities or molecular structures, such as an antibody-antigen interaction.

For instance, binding affinity typically corresponds to a $K_D$ value of about $10^{-7}$ M or less, such as about $10^{-8}$ M or less, such as about $10^{-9}$ M or less when determined by, for instance, surface plasmon resonance (SPR) technology in a BIAcore 3000 instrument using the antigen as the ligand and the antibody, Ig, antibody-binding fragment, or Fc-containing protein as the analyte (or antiligand). Cell-based binding strategies, such as fluorescent-activated cell sorting (FACS) binding assays, are also routinely used, and FACS data correlates well with other methods such as radioligand competition binding and SPR (Benedict, C A, *J Immunol Methods.* 1997, 201(2):223-31; Geuijen, C A, et al. *J Immunol Methods.* 2005, 302(1-2):68-77).

Accordingly, the antibody or antigen-binding protein of the invention binds to the predetermined antigen or cell surface molecule (receptor) having an affinity corresponding to a $K_D$ value that is at least ten-fold lower than its affinity for binding to a non-specific antigen (e.g., BSA, casein). According to the present invention, the affinity of an antibody corresponding to a $K_D$ value that is equal to or less than ten-fold lower than a non-specific antigen may be considered non-detectable binding, however such an antibody may be paired with a second antigen binding arm for the production of a bispecific antibody of the invention.

The term "$K_D$" (M) refers to the dissociation equilibrium constant of a particular antibody-antigen interaction, or the dissociation equilibrium constant of an antibody or antibody-binding fragment binding to an antigen. There is an inverse relationship between $K_D$ and binding affinity, therefore the smaller the $K_D$ value, the higher, i.e. stronger, the affinity. Thus, the terms "higher affinity" or "stronger affinity" relate to a higher ability to form an interaction and therefore a smaller $K_D$ value, and conversely the terms "lower affinity" or "weaker affinity" relate to a lower ability to form an interaction and therefore a larger $K_D$ value. In some circumstances, a higher binding affinity (or $K_D$) of a particular molecule (e.g. antibody) to its interactive partner molecule (e.g. antigen X) compared to the binding affinity of the molecule (e.g. antibody) to another interactive partner molecule (e.g. antigen Y) may be expressed as a binding ratio determined by dividing the larger $K_D$ value (lower, or weaker, affinity) by the smaller $K_D$ (higher, or stronger, affinity), for example expressed as 5-fold or 10-fold greater binding affinity, as the case may be.

The term "$k_d$" (sec−1 or 1/s) refers to the dissociation rate constant of a particular antibody-antigen interaction, or the dissociation rate constant of an antibody or antibody-binding fragment. Said value is also referred to as the $k_{off}$ value.

The term "$k_a$" (M−1×sec−1 or 1/M) refers to the association rate constant of a particular antibody-antigen interaction, or the association rate constant of an antibody or antibody-binding fragment.

The term "$K_A$" (M−1 or 1/M) refers to the association equilibrium constant of a particular antibody-antigen interaction, or the association equilibrium constant of an antibody or antibody-binding fragment. The association equilibrium constant is obtained by dividing the $k_a$ by the $k_d$.

The term "EC50" or "$EC_{50}$" refers to the half maximal effective concentration, which includes the concentration of an antibody which induces a response halfway between the baseline and maximum after a specified exposure time. The $EC_{50}$ essentially represents the concentration of an antibody where 50% of its maximal effect is observed. In certain embodiments, the $EC_{50}$ value equals the concentration of an antibody of the invention that gives half-maximal binding to cells expressing, e.g., CD3 or a tumor-associated antigen (e.g., CD20), as determined by e.g. a FACS binding assay. Thus, reduced or weaker binding is observed with an increased $EC_{50}$, or half maximal effective concentration value.

In one embodiment, decreased binding can be defined as an increased $EC_{50}$ antibody concentration which enables binding to the half-maximal amount of target cells.

In another embodiment, the $EC_{50}$ value represents the concentration of an antibody of the invention that elicits half-maximal depletion of target cells by T cell cytotoxic activity. Thus, increased cytotoxic activity (e.g. T cell-mediated tumor cell killing) is observed with a decreased $EC_{50}$, or half maximal effective concentration value.

Sequence Variants

The antibodies and bispecific antigen-binding molecules of the present invention may comprise one or more amino acid substitutions, insertions and/or deletions in the framework and/or CDR regions of the heavy and light chain variable domains as compared to the corresponding germline sequences from which the individual antigen-binding domains were derived. Such mutations can be readily ascertained by comparing the amino acid sequences disclosed herein to germline sequences available from, for example, public antibody sequence databases. The antigen-binding molecules of the present invention may comprise antigen-binding domains which are derived from any of the exemplary amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antigen-binding domain was originally derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antigen-binding domain was originally derived). Furthermore, the antigen-binding domains may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antigen-binding domains that contain one or more germline mutations can be easily tested for one or more desired property such as, improved binding specificity, increased binding affinity, improved or enhanced antagonistic or agonistic biological properties (as the case may be), reduced immunogenicity, etc. Bispecific antigen-binding molecules comprising one or more antigen-binding domains obtained in this general manner are encompassed within the present invention.

pH-Dependent Binding

The present invention includes antibodies and bispecific antigen-binding molecules with pH-dependent binding characteristics. For example, an antibody of the present invention may exhibit reduced binding to, e.g., a tumor antigen such as CD20 at acidic pH as compared to neutral pH. Alternatively, antibodies of the invention may exhibit enhanced binding to, e.g., a tumor antigen such as CD20 at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. The expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding . . . at acidic pH as compared to neutral pH" is expressed in terms of a ratio of the $K_D$ value of the antibody binding to its antigen at acidic pH to the $K_D$ value of the antibody binding to its antigen at neutral pH (or vice versa). For example, an antibody or antigen-binding fragment thereof may be regarded as exhibiting "reduced binding to, e.g., CD20 at acidic pH as compared to neutral pH" for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0. 25.0, 30.0, 40.0, 50.0, 60.0, 70.0, 100.0 or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained.

Antibodies Comprising Fc Variants

According to certain embodiments of the present invention, antibodies and bispecific antigen-binding molecules are provided comprising an Fc domain comprising one or more mutations which enhance or diminish antibody binding to the FcRn receptor, e.g., at acidic pH as compared to neutral pH. For example, the present invention includes antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the present invention includes antibodies and bispecific antigen-binding molecules comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present invention.

Preparation of Antigen-Binding Domains and Construction of Bispecific Molecules

Antigen-binding domains specific for particular antigens can be prepared by any antibody generating technology known in the art. Once obtained, two different antigen-binding domains, specific for two different antigens (e.g., CD3 and CD20), can be appropriately arranged relative to one another to produce a bispecific antigen-binding molecule of the present invention using routine methods. (A discussion of exemplary bispecific antibody formats that can be used to construct the bispecific antigen-binding molecules of the present invention is provided elsewhere herein). In certain embodiments, one or more of the individual components (e.g., heavy and light chains) of the multispecific antigen-binding molecules of the invention are derived from chimeric, humanized or fully human antibodies. Methods for making such antibodies are well known in the art. For example, one or more of the heavy and/or light chains of the bispecific antigen-binding molecules of the present invention can be prepared using VELOCIMMUNE™ technology. Using VELOCIMMUNE™ technology (or any other human antibody generating technology), high affinity chimeric antibodies to a particular antigen (e.g., CD3 or CD20) are initially isolated having a human variable region and a mouse constant region. The antibodies are characterized and selected for desirable characteristics, including affinity, selectivity, epitope, etc. The mouse constant regions are replaced with a desired human constant region to generate fully human heavy and/or light chains that can be incorporated into the bispecific antigen-binding molecules of the present invention.

Genetically engineered animals may be used to make human bispecific antigen-binding molecules. For example, a genetically modified mouse can be used which is incapable of rearranging and expressing an endogenous mouse immunoglobulin light chain variable sequence, wherein the mouse expresses only one or two human light chain variable domains encoded by human immunoglobulin sequences operably linked to the mouse kappa constant gene at the endogenous mouse kappa locus. Such genetically modified mice can be used to produce fully human bispecific antigen-binding molecules comprising two different heavy chains that associate with an identical light chain that comprises a variable domain derived from one of two different human light chain variable region gene segments. (See, e.g., US 2011/0195454). Fully human refers to an antibody, or antigen-binding fragment or immunoglobulin domain thereof, comprising an amino acid sequence encoded by a DNA derived from a human sequence over the entire length of each polypeptide of the antibody or antigen-binding fragment or immunoglobulin domain thereof. In some instances, the fully human sequence is derived from a protein endogenous to a human. In other instances, the fully human protein or protein sequence comprises a chimeric sequence wherein each component sequence is derived from human sequence. While not being bound by any one theory, chimeric proteins or chimeric sequences are generally designed to minimize the creation of immunogenic epitopes in the junctions of component sequences, e.g. compared to any wild-type human immunoglobulin regions or domains.

Bioequivalents

The present invention encompasses antigen-binding molecules having amino acid sequences that vary from those of the exemplary molecules disclosed herein but that retain the ability to bind the same antigen or antigens. Such variant molecules may comprise one or more additions, deletions, or substitutions of amino acids when compared to parent sequence, but exhibit biological activity that is essentially equivalent to that of the described antibodies or bispecific antigen-binding molecules.

The present invention includes antigen-binding molecules that are bioequivalent to any of the exemplary antigen-binding molecules set forth herein. Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple dose. Some antigen-binding proteins will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antigen-binding protein.

Bioequivalent variants of the exemplary antibodies and bispecific antigen-binding molecules set forth herein may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antigen-binding proteins may include variants of the exemplary antibodies and bispecific antigen-binding molecules set forth herein comprising amino acid changes which modify the glycosylation characteristics of the molecules, e.g., mutations which eliminate or remove glycosylation.

Therapeutic Formulation and Delivery

The present invention provides pharmaceutical compositions comprising the antigen-binding molecules of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In one embodiment, the therapeutic proteins of the invention are administered via intravenous infusion.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Therapeutic Uses of the Antigen-Binding Molecules

The present invention includes methods comprising administering to a subject in need thereof a therapeutic composition comprising a therapeutic protein. The therapeutic composition can comprise any of the antibodies or bispecific antigen-binding molecules as disclosed herein and a pharmaceutically acceptable carrier or diluent. The expression "a subject in need thereof" means a human or non-human animal that exhibits one or more symptoms or indicia of cancer (e.g., a subject expressing a tumor or suffering from any of the cancers mentioned herein below).

The antibodies and bispecific antigen-binding molecules of the invention (and therapeutic compositions comprising the same) are useful, inter alia, for treating any disease or disorder in which stimulation, activation and/or targeting of an immune response would be beneficial. In particular, the antibodies or the bispecific antigen-binding molecules of the present invention may be used for the treatment, prevention and/or amelioration of any disease or disorder associated with or mediated by, e.g., CD20, PSMA, MUC16, STEAP2 or BCMA expression or activity or the proliferation of CD20+, PSMA+, MUC16+, STEAP2+, or BCMA+ cells. The mechanism of action by which the therapeutic methods of the invention are achieved include killing of the cells expressing such antigens in the presence of effector cells, for example, by CDC, apoptosis, ADCC, phagocytosis, or by a combination of two or more of these mechanisms.

The antigen-binding molecules of the present invention may be used to treat, e.g., primary and/or metastatic tumors arising in the brain and meninges, head and neck, oropharynx, lung and bronchial tree, gastrointestinal tract, male and female reproductive tract, muscle, bone, skin and appendages, connective tissue, spleen, immune system, blood forming cells and bone marrow, liver and urinary tract, kidney, bladder and/or special sensory organs such as the eye. In certain embodiments, the antibodies and bispecific antigen-binding molecules of the invention are used to treat one or more of, but not limited to, the following cancers: pancreatic carcinoma, head and neck cancer, prostate cancer, malignant gliomas, osteosarcoma, colorectal cancer, gastric cancer (e.g., gastric cancer with MET amplification), malignant mesothelioma, multiple myeloma, ovarian cancer, small cell lung cancer, non-small cell lung cancer, synovial sarcoma, thyroid cancer, breast cancer, melanomaglioma, breast cancer (e.g. ductal or intraductal breast carcinoma, squamous cell carcinoma, esophageal cancer, clear cell renal cell carcinoma, chromophobe renal cell carcinoma, (renal) oncocytoma, (renal) transitional cell carcinoma, urothelial carcinoma, (bladder) adenocarcinoma, or (bladder) small cell carcinoma. According to certain embodiments of the present invention, the antibodies or bispecific antibodies are useful for treating a patient afflicted with a refractory or treatment-resistant cancer, e.g. castrate-resistant prostate cancer.

In some embodiments, the antigen-binding molecule is a bispecific anti-CD3×anti-CD20 antibody useful for treating a CD20-expressing cancer including non-Hodgkin lymphoma, Hodgkin lymphoma, chronic lymphocytic leukemia, acute lymphoblastic leukemia, small lymphocytic lymphoma, diffuse large B-cell lymphoma, follicular lymphoma, mantle cell lymphoma, marginal zone lymphoma, Waldenstrom macroglobulinemia, primary mediastinal B-cell lymphoma, lymphoblastic lymphoma, or Burkitt lymphoma. In some embodiments, the cancer is follicular lymphoma. In some embodiments, the cancer is diffuse large B-cell lymphoma (DLBCL). In some embodiments, the cancer is mantle cell lymphoma. In some embodiments, the cancer is marginal zone lymphoma. In some embodiments, the cancer is follicular lymphoma and the maximum weekly dose of the bispecific antibody is 80 mg. In some embodiments, the cancer is DLBCL and the maximum weekly dose of the bispecific antibody is 80 mg. In some embodiments, the cancer is DLBCL and the maximum weekly dose of the bispecific antibody is 160 mg. In some embodiments, the cancer is DLBCL and the maximum weekly dose of the bispecific antibody is 320 mg. In any of these embodiments, or others discussed herein, the cancer patient may have been pretreated with an anti-CD20 monospecific antibody therapy.

Non-Hodgkin Lymphoma (NHL) is the most common hematological malignancy. Among a heterogeneous group of NHLs, 85-90% are of B-cell origin and include follicular lymphoma (FL), diffuse large B-cell lymphoma (DLBCL), mantle cell lymphoma (MCL), marginal zone lymphoma (MZL), and several other B-NHLs. Anti-CD20 antibodies in combination with chemotherapy are the standard of care for the treatment of B-NHLs; however, despite initial responses, many patients relapse, often with progressively shorter response durations in subsequent lines of therapy and poor outcomes. Thus, in some embodiments, the antigen-binding molecule is a bispecific anti-CD3×anti-CD20 that binds to CD3+ T cells and CD20+ B cells, targeting CD20+ tumor cells via T-cell mediated cytotoxicity. In some cases, the anti-CD3×CD20 bispecific antibody is for treatment of a B-cell cancer (e.g., a NHL) in a subject that has failed prior therapy with an anti-CD20 monospecific antibody.

For patients with less than a complete response to CAR-T therapy, the outcomes are generally poor, and there are no standard-of-care therapeutic options. Thus, in some cases, the anti-CD3×CD20 bispecific antibody of the present invention is for treatment of a B-cell cancer (e.g., a NHL such as DLBCL) in a subject that has failed prior CAR-T therapy or is not responsive to prior CAR-T therapy (e.g., anti-CD19 CAR-T therapy).

In some embodiments, the antigen-binding molecule is a bispecific anti-CD3×anti-PSMA antibody useful for treating a PSMA-expressing cancer including prostate cancer, kidney cancer, bladder cancer, colorectal cancer, and gastric cancer. In some embodiments, the cancer is prostate cancer (e.g., castrate-resistant prostate cancer).

In some embodiments, the antigen-binding molecule is a bispecific anti-CD3×anti-MUC16 antibody useful for treating a MUC16-expressing cancer including ovarian cancer, breast cancer, pancreatic cancer, non-small-cell lung cancer, intrahepatic cholangiocarcinoma-mass forming type, adenocarcinoma of the uterine cervix, and adenocarcinoma of the gastric tract. In some embodiments, the cancer is ovarian cancer.

In some embodiments, the antigen-binding molecule is a bispecific anti-CD3×anti-STEAP2 antibody useful for treating a STEAP2-expressing cancer including prostate cancer, bladder cancer, cervical cancer, lung cancer, colon cancer, kidney cancer, breast cancer, pancreatic cancer, stomach cancer, uterine cancer, and ovarian cancer. In some embodiments, the cancer is prostate cancer (e.g., castrate-resistant prostate cancer).

In some embodiments, the antigen-binding molecule is a bispecific anti-CD3×anti-BCMA antibody useful for treating a BCMA-expressing cancer including multiple myeloma or other B-cell or plasma cell cancers, such as Waldenström's macroglobulinemia, Burkitt lymphoma, and diffuse large B-Cell lymphoma, Non-Hodgkin's lymphoma, chronic lymphocytic leukemia, follicular lymphoma, mantle cell lymphoma, marginal zone lymphoma, lymphoplasmacytic lymphoma, and Hodgkin's lymphoma. In some embodiments, the cancer is multiple myeloma.

Combination Therapies

The present invention provides methods which comprise administering a pharmaceutical composition comprising any of the exemplary antibodies and bispecific antigen-binding molecules described herein in combination with one or more additional therapeutic agents. Exemplary additional therapeutic agents that may be combined with or administered in combination with an antigen-binding molecule of the present invention include, e.g., an anti-tumor agent (e.g. chemotherapeutic agents including melphalan, vincristine (Oncovin), cyclophosphamide (Cytoxan), etoposide (VP-16), doxorubicin (Adriamycin), liposomal doxorubicin (Doxil), obendamustine (Treanda), or any others known to be effective in treating a plasma cell tumor in a subject.). In certain embodiments the second therapeutic agent is a regimen comprising radiotherapy or a hematopoietic stem cell transplant. In certain embodiments, the second therapeutic agent may be an immunomodulatory agent. In certain embodiments, the second therapeutic agent may be a proteasome inhibitor, including bortezomib (Velcade), carfilzomib (Kyprolis), ixazomib (Ninlaro). In certain embodiments the second therapeutic agent may be a histone deacetylase inhibitor such as panobinostat (Farydak). In certain embodiments, the second therapeutic agent may be a monoclonal antibody, an antibody drug conjugate, a bispecific antibody conjugated to an anti-tumor agent, an immune checkpoint inhibitor, or combinations thereof. The pharmaceutical compositions of the present invention (e.g., pharmaceutical compositions comprising bispecific antigen-binding molecule as disclosed herein) may also be administered as part of a therapeutic regimen comprising one or more therapeutic combinations selected from a monoclonal antibody other than those described herein, which may interact with a different antigen on the plasma cell surface, a bispecific antibody, which has one arm that binds to an antigen on the tumor cell surface and the other arm binds to an antigen on a T cell, an antibody drug conjugate, a bispecific antibody conjugated with an anti-tumor agent, a checkpoint inhibitor, for example, one that targets, PD-1 or CTLA-4, or combinations thereof. In certain embodiments, the checkpoint inhibitors may be selected from PD-1 inhibitors, such as pembrolizumab (Keytruda), nivolumab (Opdivo), or cemiplimab. In certain embodiments, the checkpoint inhibitors may be selected from PD-L1 inhibitors, such as atezolizumab (Tecentriq), avelumab (Bavencio), or Durvalumab (Imfinzi)). In certain embodiments, the checkpoint inhibitors may be selected from CTLA-4 inhibitors, such as ipilimumab (Yervoy). Other combinations that may be used in conjunction with an antibody of the invention are described above.

The present invention also includes therapeutic combinations comprising any of the antigen-binding molecules mentioned herein and an inhibitor of one or more of VEGF, Ang2, DLL4, EGFR, ErbB2, ErbB3, ErbB4, EGFRvIII, cMet, IGF1R, B-raf, PDGFR-α, PDGFR-β, FOLH1 (PSMA), PRLR, STEAP1, STEAP2, TMPRSS2, MSLN, CA9, or uroplakin, wherein the inhibitor is an aptamer, an antisense molecule, a ribozyme, an siRNA, a peptibody, a nanobody or an antibody fragment (e.g., Fab fragment; $F(ab')_2$ fragment; Fd fragment; Fv fragment; scFv; dAb fragment; or other engineered molecules, such as diabodies, triabodies, tetrabodies, minibodies and minimal recognition units). The antigen-binding molecules of the invention may also be administered and/or co-formulated in combination with antivirals, antibiotics, analgesics, and/or NSAIDs. The antigen-binding molecules of the invention may also be administered as part of a treatment regimen that also includes radiation treatment and/or conventional chemotherapy.

The additional therapeutically active component(s) may be administered just prior to, concurrent with, or shortly after the administration of an antigen-binding molecule of the present invention; (for purposes of the present disclosure, such administration regimens are considered the administration of an antigen-binding molecule "in combination with" an additional therapeutically active component).

The present invention includes pharmaceutical compositions in which an antigen-binding molecule of the present invention is co-formulated with one or more of the additional therapeutically active component(s) as described elsewhere herein.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Clinical Evaluation and Dose Escalation of a Bispecific Antibody

The below-described clinical study is an open-label, multi-center phase 1 study to investigate the safety and tolerability of REGN1979, an anti-CD20×anti-CD3 bispecific monoclonal antibody, in patients with CD20+ B-cell malignancies previously treated with CD20-directed antibody therapy.

Objectives: The primary objectives of the study were to assess the safety, tolerability, and dose-limiting toxicities (DLTs) of REGN1979 administered intravenously (IV), and to study the antitumor activity of REGN1979 in expansion cohorts comprising diffuse large B-cell lymphoma (DLBCL) after failure of chimeric antigen receptor T cell (CAR-T) therapy, aggressive lymphoma (other than DLBCL after failure of CAR-T therapy), follicular lymphoma (FL) grade 1-3a, and chronic lymphocytic leukemia (CLL). The secondary objectives of the study were: (1) to characterize the pharmacokinetic (PK) profile of REGN1979; (2) to assess the immunogenicity of REGN1979; (3) to study the preliminary antitumor activity of REGN1979 administered to patients with CD20+ B-cell malignancies (non-Hodgkin lymphoma [NHL] previously treated with anti-CD20 antibody therapy, or chronic lymphocytic leukemia [CLL]); and (4) to study the preliminary antitumor activity of REGN1979 in the dose escalation portion of the study. Minimal residual disease (MRD) assessments were made in patients with CLL. The exploratory objectives of the study were to evaluate biomarkers that may correlate with mechanism of action, observed toxicity, and potential anti-tumor activity including, but not limited, to: (1) cytokine profiling and assessment of inflammatory markers (e.g., C-reactive protein [CRP]); (2) peripheral blood B-cell and T-cell subsets and immune phenotyping; and (3) changes in gene expression in peripheral blood.

Study Design: Patients were assigned to a dose level (DL) cohort that consists of an initial starting dose, followed by higher step-up doses for second and subsequent dose administrations. Patients were enrolled based on indication (NHL or CLL). At each DL, there were 2 cohorts (one for each indication), with 3 to 6 patients per NHL cohort, and 1 to 6 patients per CLL cohort. Patients with small lymphocytic lymphoma (SLL) were enrolled in the CLL arm and follow NHL assessments.

Patients who initially showed a clinical benefit and who subsequently relapsed or progressed or had a suboptimal response to treatment may have been re-treated with REGN1979 at the highest DL that was deemed tolerable at the time of relapse or progression.

Patients underwent screening procedures to determine eligibility within 28 days prior to the initial administration of REGN1979. Patients were enrolled sequentially based on indication (NHL or CLL) in order of confirmation of eligibility by the sponsor until each cohort was filled per protocol criteria.

There were separate independent dose escalation cohorts for NHL and CLL at each DL. Each DL consisted of an initial dose and a second and subsequent dose, which was higher than the starting dose, provided the initial dose was tolerated.

Dose escalation followed a traditional 3+3 dose escalation design for patients with NHL. Three to 6 patients were planned per cohort based on observed toxicity.

Dose escalation followed a modified 3+3 with an accelerated titration component for patients with CLL. Based on observed toxicity, 1 to 6 patients were planned per cohort.

Upon completion of the dose escalation phase, and upon determination of a recommended dose for further study in patients with NHL, three expansion cohorts were to be opened for 1) patients with DLBCL after failure of CAR-T therapy (20 patients), 2) aggressive lymphoma (other than DLBCL after failure of CAR-T therapy) (40 patients; among whom 20 patients were to be enrolled each into aggressive lymphoma cohort 1 [160 mg step-up dose]), and cohort 2 [80 mg step-up dose]), and 3) patients with relapsed/refractory follicular lymphoma grade 1-3a (60 patients; among whom 30 were to be enrolled each into cohort 1 [80 mg step-up dose] and cohort 2 [160 mg step-up dose]). The weekly step-up dose of REGN1979 for each of these expansion cohorts (except for aggressive lymphoma cohort 2 and follicular lymphoma cohort 1) was set at 160 mg weekly, followed by Q2W maintenance treatment with 320 mg REGN1979. In the aggressive lymphoma cohort 2 and follicular lymphoma cohort 1, the weekly step-up dose of REGN1979 was 80 mg, and the Q2W maintenance dose of REGN1979 was 160 mg For patients assigned to a step-up dose of 80 mg, patients received 80 mg weekly during a 4-week induction period, after the initial dose escalation, followed by an additional 8 weekly doses, and 160 mg Q2W treatment through progression, with an option to discontinue treatment after the patient has shown a durable response for at least 9 months after the initial demonstration of a CR. For patients assigned to a step-up dose of 160 mg, patients received 160 mg weekly during a 4-week induction period, after the initial dose escalation, followed by an additional 8 weekly doses, and 320 mg Q2W treatment through progression, with an option to discontinue treatment after the patient has shown a durable response for at least 9 months after the initial demonstration of a CR.

The utility of a rituximab lead-in dose prior to the first administration of REGN1979 was studied in patients with NHL to determine whether this intervention can decrease the incidence and severity of infusion-related reaction (IRR) and cytokine release syndrome (CRS). In the rituximab lead-in cohort, REGN1979 was administered using a step-up dose of 160 mg during weekly treatment and 320 mg during Q2W maintenance treatment. Subsequently, an additional 24 patients were to be treated with the optimal dose regimen and dose; together with the 6 patients in the rituximab lead-in group treated at the optimal dose a total of 30 patients were reviewed for safety and tolerability.

In the first DL for the dose escalation portion, there was a required 48-hour waiting period between initial study drug administrations for the first 3 patients within the same indication. Subsequent patients in the first DL were not treated on the same day, regardless of indication. In subsequent cohorts, provided there was no unexpected toxicity observed in previous cohorts or within the cohort, the initial infusions for the first 3 patients were administered at least 24 hours apart.

After each cohort of patients was enrolled, treated, and completed the DLT observation period, opening of subsequent DL cohorts for enrollment (or expansion of the current open DL cohort) was determined once the safety data had been reviewed by both the sponsor and the investigator(s).

The DLT observation period was defined as the first 28 days of treatment, which in this study corresponds with the induction period. During induction, patients were treated with 4 weekly administrations of REGN1979.

In order to be DLT evaluable, an individual patient must have received at least the first 2 administrations of REGN1979 (week 1 day 1 ["initial or primary dose"] and week 2 day 1 ["secondary and subsequent dose"]), or experienced a DLT. Patients enrolled to DL11 and above must have received at least the first 3 administrations of REGN1979 (week 1 initial dose, week 2 intermediate or secondary dose, and week 3 higher tertiary or step-up dose), or experienced a DLT. Additionally, the patient must have been evaluated for at least 28 days from the first administration, and at least 21 days from the second administration.

Dose escalation and cohorts for the NHL and CLL patients are shown in Table 1, below.

TABLE 1

Dose Escalation and Cohorts

| Dose Level | Initial Dose (mcg) | Inter-mediate Dose (mcg) | Maximum Dose (Step-up dose) (mcg) | NHL | n | CLL | n |
|---|---|---|---|---|---|---|---|
| DL1 | 30 | — | 100 | Cohort 1 | 3-6 | Cohort 1 | 1-6 |
| DL2 | 100 | — | 300 | Cohort 2 | 3-6 | Cohort 2 | 1-6 |
| DL3 | 300 | — | 1000 | Cohort 3 | 3-6 | Cohort 3 | 1-6 |
| DL4 | 1000 | — | 2000 | Cohort 4 | 3-6 | Cohort 4 | 1-6 |
| DL5 | 1000 | — | 3000 | Cohort 5 | 3-6 | Cohort 5 | 1-6 |
| DL6 | 1000 | — | 4000 | Cohort 6 | 3-6 | Cohort 6 | 1-6 |
| DL7 | 1000 | — | 5000 | Cohort 7 | 3-6 | Cohort 7 | 1-6 |
| DL8 | 1000 | — | 6000 | Cohort 8 | 3-6 | Cohort 8 | 1-6 |
| DL9 | 1000 | — | 7000 | Cohort 9 | 3-6 | Cohort 9 | 1-6 |
| DL10 | 1000 | — | 8000 | Cohort 10 | 3-6 | Cohort 10 | 1-6 |
| DL11 | 1000 | 6,000 | 12,000 | Cohort 11 | 3-6 | Cohort 11 | 1-6 |
| DL12 | 1000 | 9,000 | 18,000 | Cohort 12 | 3-6 | Cohort 12 | 1-6 |
| DL13 | 1000 | 13,500 | 27,000 | Cohort 13 | 3-6 | Cohort 13 | 1-6 |
| DL14 | 1000 | 20,000 | 40,000 | Cohort 14 | 3-6 | Cohort 14 | 1-6 |
| DL15 | 1000 | 20,000 | 80,000 | Cohort 15 | 3-6 | Cohort 15 | 1-6 |
| DL16 | 1000 | 20,000 | 160,000 | Cohort 16 | 3-6 | Cohort 16 | 1-6 |
| DL17 | 1000 | 20,000 | 320,000 | Cohort 17 | 3-6 | Cohort 17 | 1-6 |

In this study, each dose level comprises an initial REGN1979 dose followed by a step-up dose; for cohorts DL11 and above, a secondary dose has been added prior to reaching the step-up dose (see Table 1). The initial (primary) dose, the intermediate (secondary) dose (if applicable), and the first administration of the step-up (tertiary) dose are each optionally split over at least 2 days. All patients in the DL7 and higher maximum dose cohorts received split dosing (e.g., fractionated dosing) for initial (primary) and intermediate (secondary) doses. Patients in DL11 and higher maximum dose cohorts received split dosing (e.g., fractionated dosing) for initial (primary), intermediate (secondary) and first step-up (tertiary) doses, followed by step-up doses (maximum weekly dose) thereafter.

Study Duration: The treatment period is 9 months. Patients will be treated with up to 24 doses of REGN1979—4 weekly doses during a 4-week induction period, followed by an additional 8 weekly doses, and 12 or more doses administered twice-monthly (Q2W) during a maintenance period through progression, with an option to discontinue treatment following 9 months after patient achieved a complete response. Patients may be followed for efficacy and safety for up to 15 months after end of treatment.

Study Population: Assuming enrollment through DL17 and complete enrollment into all expansion cohorts, up to 370 patients are planned at approximately 15 sites across the United States and Germany. Up to 204 patients will be enrolled in the dose escalation cohorts through DL17 for both indications (NHL and CLL) during the dose escalation phase. Up to 100 patients comprising 90 NHL patients (20 DLBCL patients after failure of CAR-T therapy, 40 aggressive lymphoma patients [other than DLBCL after failure of CAR-T therapy], 30 FL grade 1-3a patients), and 10 CLL patients will be enrolled in the disease-specific expansion cohorts. Up to 42 patients will be enrolled in the rituximab lead-in cohort to determine the optimal dose regimen. Once the optimal rituximab lead-in dose regimen is determined, an additional 24 patients will be enrolled into the rituximab lead-in expansion and will be combined with the 6 patients from the above rituximab lead-in group treated with the optimal dose regimen and dose. Thus, a total of 30 patients will be evaluated at the optimal rituximab lead-in dose regimen and dose.

Patients must have documented CD20+ B-cell malignancy, with active disease not responsive to prior therapy, for whom no standard of care options exists, and for whom treatment with an anti-CD20 antibody may be appropriate. Patients with NHL must have previously been treated with CD20-directed antibody therapy.

Inclusion Criteria: A patient must meet the following criteria to be eligible for inclusion in the study:

1. Have documented CD20+ B-cell malignancy, with active disease not responsive to prior therapy, for whom no standard of care options exists, and for whom treatment with an anti-CD20 antibody may be appropriate:

B-NHL confirmed by NCI working group criteria, 2007 (Cheson 2007, Appendix 2); and CLL confirmed by the International Workshop on Chronic Lymphocytic Leukemia (IWCLL) working group criteria, 2008 (Hallek 2008, Appendix 3)—Patients with small lymphocytic lymphoma (SLL) will be enrolled in the CLL arm and follow NHL assessments.

Note—A patient with CD20-negative lymph node (NHL) biopsy performed as standard of care just prior to enrollment, remains eligible for the study provided the patient had previously documented CD20+ disease AND was previously treated with rituximab or other CD20-directed antibody therapy within approximately 6 months. Individual cases may be discussed with the medical monitor.

2. Patients with NHL must have had prior treatment with an anti-CD20 antibody therapy. Patients with CLL are not required to have received prior treatment with an anti-CD20 antibody therapy, provided the patient has failed either a BTK inhibitor or PI3K inhibitor and the treating physician deems it appropriate for the patient to be entered into a phase 1 trial. For inclusion in FL grade 1-3a expansion cohort, patients must have received at least 2 prior lines of systemic therapy, including an anti-CD20 antibody and an alkylating agent. For the inclusion in the disease-specific expansion cohort enrolling DLBCL patients after failure of CAR-T therapy, the patient must have recovered from the toxicities of the lymphodepletion therapy and CAR-T infusion. There is no requirement for the prior CAR-T therapy to be the most recent line of therapy before study enrollment.

3. All patients (B-cell NHL and CLL) must have at least one bi-dimensionally measurable lesion ≥1.5 cm) documented by CT or MRI scan, if CT scan is not feasible.

4. Patients with CLL must have white blood cell (WBC) ≤200×109/L

5. Age ≥18 years

6. Eastern Cooperative Oncology Group (ECOG) performance status ≤1

7. Life expectancy of at least 6 months

8. Adequate bone marrow function documented by: a. Platelet counts ≥75×109/L; b. Hb level ≥9 g/dL; c. ANC ≥1×109/L Note—Patients with cell counts below thresholds listed above may be considered for enrollment if, in the opinion of the investigator, the reason is believed to be due to bone marrow infiltration by underlying disease. In such cases, the investigator must discuss the eligibility with the sponsor and receive approval for enrollment in writing.

9. Adequate organ function documented by:

Aspartate aminotransferase (AST) and alanine aminotransferase (ALT) ≤2.5×ULN

Total bilirubin ≤1.5×ULN

Note—Patients with Gilbert's syndrome do not need to meet this requirement provided their total bilirubin is unchanged from their baseline.

Calculated creatinine clearance by Cockcroft-Gault 50 mL/min

Note—Patients may be considered for enrollment if, in the opinion of the investigator, the abnormal laboratory results are due to underlying disease. In such cases, the investigator must discuss the eligibility with the sponsor and receive approval for enrollment in writing.

Note—Patients with borderline creatinine clearance by Cockcroft-Gault may be considered for enrollment if a measured creatinine clearance (based on 24-hour urine or other reliable method) is ≥50 mL/min.

10. Willingness to undergo mandatory tumor biopsy pre-treatment, if in the opinion of the investigator, the patient has an accessible lesion that can be biopsied without significant risk to the patient.

11. Willing and able to comply with clinic visits and study-related procedures

12. Provide signed informed consent.

Exclusion Criteria: A patient who meets any of the following criteria will be excluded from the study:

1. Primary central nervous system (CNS) lymphoma or known or suspected CNS involvement by non-primary CNS NHL 2. History of or current relevant CNS pathology such as Epilepsy, seizure, paresis, aphasia, apoplexia, severe brain injuries, cerebellar disease, organic brain syndrome, psychosis, or Evidence for presence of inflammatory lesions and/or vasculitis on cerebral MRI 3. Standard anti-neoplastic chemotherapy (non-biologic) within 5-times the half-life or within 28 days, whichever is shorter, prior to first administration of study drug.

4. Standard radiotherapy within 14 days of first administration of study drug.

Note—Palliative radiotherapy to a symptomatic lymph node/lesion is allowed provided the irradiated lesion(s) or node(s) is not included as a target lesion for tumor assessments 5. Allogeneic stem cell transplantation 6. Treatment with rituximab, alemtuzumab or other investigational or commercial biologic agent within 12 weeks prior to first administration of study drug.

Note—for patients with aggressive lymphoma for which immediate treatment is required, the wash-out period may be reduced to 28 days. This will require discussion with and approval by the sponsor in writing.

7. Immunosuppressive therapy (other than biologic) within 28 days of first administration of study drug.

8. Treatment with an investigational non-biologic agent within 28 days of first administration of study drug.

9. History of allergic reactions attributed to compounds of similar chemical or biologic composition of study drug.

10. History of hypersensitivity to any compound in the tetracycline antibiotics group.

11. Concurrent active malignancy for which the patient is receiving treatment.

12. Known active bacterial, viral, fungal, mycobacterial or other infection or any major episode of infection requiring hospitalization or treatment with IV anti-infectives within 4 weeks of first administration.

13. Evidence of significant concurrent disease or medical condition that could interfere with the conduct of the study, or put the patient at significant risk including, but not limited to, significant cardiovascular disease (eg, New York Heart Association Class III or IV cardiac disease, myocardial infarction within the previous 6 months, unstable arrhythmias or unstable angina) and/or significant pulmonary disease (eg, obstructive pulmonary disease and history of symptomatic bronchospasm).

Note—Patients with a medical history of cardiac disease should be evaluated by ECHO or multigated acquisition scan (MUGA) prior to first administration of REGN1979 to ensure adequate cardiac reserves and function.

14. Ongoing systemic corticosteroid treatment, with the exception of corticosteroid use for other (non-tumor and non-immunosuppressive) indications up to a maximum of 10 mg/day of prednisone or equivalent.

15. Infection with human immunodeficiency virus (HIV) or chronic infection with hepatitis B virus (HBV) or hepatitis C virus (HCV). Patients with hepatitis B (HepBsAg+) who have controlled infection (serum hepatitis B virus DNA that is below the limit of detection AND receiving anti-viral therapy for hepatitis B) are permitted upon consultation with the physician managing the infection.

16. Known hypersensitivity to both allopurinol and rasburicase.

17. Pregnant or breast-feeding women.

18. Women of childbearing potential* who are unwilling to practice highly effective contraception prior to the initial study drug treatment, during the study, and for at least 6 months after the last dose. Highly effective contraceptive measures include stable use of combined (estrogen and progestogen containing) hormonal contraception (oral, intravaginal, transdermal) or progestogen-only hormonal contraception (oral, injectable, implantable) associated with inhibition of ovulation initiated 2 or more menstrual cycles prior to screening; intrauterine device; intrauterine hormone-releasing system; bilateral tubal ligation; vasectomized partner; and or sexual abstinence†, ‡.

* Postmenopausal women must be amenorrheic for at least 12 months in order not to be considered of child bearing potential. Pregnancy testing and contraception are not required for women with documented hysterectomy or tubal ligation.

† Sexual abstinence is considered a highly effective method only if defined as refraining from heterosexual intercourse during the entire period of risk associated with the study treatments. The reliability of sexual abstinence needs to be evaluated in relation to the duration of the clinical trial and the preferred and usual lifestyle of the patient.

‡ Periodic abstinence (calendar, symptothermal, post-ovulation methods), withdrawal (coitus interruptus), spermicides only, and lactational amenorrhoea method (LAM) are not acceptable methods of contraception. Female condom and male condom should not be used together.

19. Administration of live vaccination within 28 days of first administration of study drug 20. Member of the clinical site study team and/or his/her immediate family, unless prior approval is granted by the Sponsor.

Treatments: REGN1979 was supplied as a liquid in sterile, single-use vials. Each vial contained REGN1979 at a concentration of 2 mg/mL. Detailed preparation and administration instructions were provided to the sites in the pharmacy manual. Diluent was supplied for REGN1979 study drug preparation.

Patients received REGN1979 weekly during a 4-week induction period, followed by another 8 weekly doses, and Q2W doses until progression, at a dose per their assigned cohort.

In the rituximab lead-in cohort and expansion only, a single dose of rituximab (375 mg/m$^2$) was administered one day prior to the first dose of REGN1979 [i.e, on study day (−1)]. REGN1979 was started on Week 1 Day 1, and the treatment period for REGN1979 was 9 months. Patients were treated with up to 24 doses of REGN1979: 4 weekly doses during a 4-week induction period, followed by an additional 8 weekly doses, and 12 or more doses administered Q2W during a maintenance period, until progression. In the rituximab lead-in cohort, REGN1979 was administered using a step-up dose of 160 mg during weekly treatment and 320 mg during Q2W maintenance treatment. Dose groups with step-up doses of REGN1979 below 160 mg weekly treatment and below 320 mg REGN1979 Q2W maintenance treatment may be evaluated also. Subsequently, an additional 24 patients were evaluated with the optimal dose regimen and dose; together with the 6 patients in the rituximab lead-in group treated with the optimal dose regimen and dose, a total of 30 patients were reviewed for safety and tolerability.

Endpoints

Primary: The primary endpoints were safety (specifically, adverse events [AEs] and DLTs) to determine the maximum tolerated dose (MTD) and/or optimal biological dose (OBD) as recommended phase 2 dose (RP2D) of REGN1979; and efficacy as measured by the objective response rate (ORR) in the expansion cohort of DLBCL patients after failure of CAR-T therapy, aggressive lymphoma (other than DLBCL after failure of CAR-T therapy) expansion cohorts 1 and 2, the FL grade 1-3a expansion cohort, and the CLL expansion cohort.

Secondary: The secondary endpoints were:

Pharmacokinetics: Concentration of REGN1979

Immunogenicity: Anti-REGN1979 antibodies

Antitumor activity:

Objective response rate (ORR)

- Tumor response assessment per the Revised Response Criteria for Malignant Lymphoma of the NCI-International Working Group (NCI-WG)
- Tumor response assessment as per the International Workshop on Chronic Lymphocytic Leukemia Guidelines for the Diagnosis and treatment of CLL
- For patients enrolled into NHL expansion cohorts, tumor response assessment as per the Lugano Classification Progression free survival (PFS) and overall survival (OS)

Minimal residual disease (MRD) for patients with CLL

The exploratory endpoints include:

Pharmacodynamic (PD) measures including:

B-cell and T-cell subsets and phenotype

Circulating cytokine levels

CRP

Changes in gene expression in peripheral blood

Procedures and Assessments

Baseline procedures: Brain MRI, electrocardiogram (ECG), human immunodeficiency virus (HIV), hepatitis C virus (HCV), and hepatitis B virus (HBV) testing, and coagulation.

Safety procedures: Medical history, physical examination, assessment of symptoms, evaluation of performance status, clinical laboratory tests, vital signs, AEs, and concomitant medications.

Efficacy procedures: Tumor assessments, including CT or MRI scans, 18F-fluorodeoxyglucose-positron emission tomography (FDG-PET) scans, bone marrow aspirate and biopsies, lymph node and/or tumor biopsies, and peripheral blood samples (CLL patients only). Blood samples for PK and anti-drug antibody (ADA) assessment were collected. Biomarkers samples were collected to monitor for changes in cytokine production, serum levels of pro-inflammatory cytokines, and changes in lymphocyte subsets and activation status. In addition, these samples permitted tumor or somatic genetic analyses for variations that impact the clinical course of underlying disease or modulate treatment side effects.

Statistical Plan: The study design was based on a traditional 3+3 design with 3 to 6 patients per DL for patients with NHL, and a modified 3+3 design with an accelerated titration component with 1 to 6 patients per DL for patients with CLL. The exact number of patients enrolled will depend on the number of patients (NHL and CLL) observed with protocol-defined DLTs and grade 2 or higher treatment-related toxicity in which acute effects (with the exception of associated laboratory abnormalities) resolve to grade 1 or baseline within 72 hours (CLL during the accelerated titration component), and the need to expand currently defined DLs, or open additional cohorts at lower DLs.

Patient enrolment is on-going and up to 370 patients are planned. Up to 204 patients will be enrolled in the dose escalation cohorts through DL17 for both indications (NHL and CLL) during the dose escalation phase. Up to 100 patients comprising 90 NHL patients (20 DLBCL patients after failure of CAR-T therapy, 40 aggressive lymphoma patients [other than DLBCL after failure of CAR-T therapy], and 30 FL grade 1-3a patients), and 10 CLL patients will be enrolled in the disease-specific expansion cohorts. Up to 42 patients will be enrolled in the rituximab lead-in cohort to determine the optimal dose regimen. An additional 24 patients will be enrolled into a rituximab lead-in expansion and will be combined with the 6 patients from the above rituximab lead-in cohort treated with the optimal dose regimen and dose. Thus, a total of 30 patients will be evaluated at the at the optimal rituximab lead-in dose regimen and dose.

Data is summarized using descriptive statistics only. In general, data is summarized by DL, and by indication (NHL or CLL). Within the NHL indication, data will also by summarized by the subgroups and dose of DLBCL after failure of CAR-T therapy, aggressive lymphoma (other than DLBCL after failure of CAR-T therapy) cohorts 1 and 2, and FL grade 1-3a. Within the NHL indication, data is also summarized by the subgroups of indolent and aggressive NHL. Demographic and baseline characteristics is summarized descriptively by group.

The safety summaries and analyses were performed on the safety analysis set (SAF). The primary analysis of safety was based on treatment-emergent AEs (TEAEs). This analysis comprised the basis upon which conclusions were drawn regarding the safety profile of REGN1979. All AEs reported in this study were coded using the currently available version of the Medical Dictionary for Regulatory Activities (MedDRA®). Coding will be to lowest level terms. The verbatim text, the preferred term (PT), and the primary system organ class (SOC) was listed. The analysis for efficacy and baseline variables is performed on the efficacy analysis set (FAS). The efficacy analyses for the expansion cohorts comprising DLBCL after failure of CAR-T therapy, aggressive lymphoma (other than DLBCL after failure of CAR-T therapy) cohorts 1 and 2, FL grade 1-3a, and CLL will be performed separately after all the patients in the respective cohort have completed the 24-week visit or have discontinued from the study prior to this time.

Results: Results for patients that were administered a maximum weekly dose of 5 to 320 mg indicate a low incidence of CRS. Serum concentrations of REGN1979 in patients receiving a maximum weekly dose of as little as 12 mg were observed to approach or exceed serum concentration levels that have been demonstrated to be effective in Raji tumor xenograft mouse models (data not shown). Patients receiving a maximum weekly dose of as little as 40 mg maintained a serum concentration exceeding the minimum concentration level (2000 μg/L) demonstrated to be effective in the Raji tumor xenograft mouse models (data not shown). In addition, numerous partial and complete responses were also observed in the patients treated at these levels, as shown in Tables 2-9, below. The cumulative REGN1979 safety and PK experience through the DLT evaluation period of Cohort 13N (27,000 mcg REGN1979) demonstrates that the management algorithm for CRS or IRR reactions (i.e., incremental dose escalation, split dosing during the initial weeks of REGN1979 administration, and premedication with corticosteroid) has proved effective in preventing severe CRS or IRR despite incremental increases in dosing in successive dose cohorts. Split dosing provided a benefit to patient safety in weeks 1 through 4 (the available data), wherein less overall incidents of severe CRS/IRR were observed. Particularly, the dosing strategy discussed herein provided a safer strategy for escalating doses to levels greater than 80 mg, even 160 mg or greater, with less severe events occurring in weeks 3 and 4 when higher doses reached and exceeded the desired serum concentrations discussed above. FIG. 1 illustrates the incidence of CRS/IRR for patients receiving up to a maximum dose of 320 mg. To date, no patients have been discontinued due to a CRS/IRR adverse event.

TABLE 2

Observed Response in Follicular Lymphoma Grade 1-3a

| | CD20xCD3† | | | |
|---|---|---|---|---|
| | <5 mg (N = 7) | 5-12 mg (N = 5) | 18-40 mg (N = 6) | 160 mg (N = 1) |
| Overall response rate, n (%) | 1 (14.3) | 5 (100) | 5 (83.4) | 1 (100) |
| Complete response, n (%) | 1 (14.3) | 4 (80) | 4 (66.7) | 0 |
| Partial response, n (%) | 0 | 1 (20) | 1 (16.7) | 1 (100) |
| Stable disease, n (%) | 4 (57.1) | 0 | 1 (16.7) | 0 |
| Progressive disease, n (%) | 2 (28.6) | 0 | 0 | 0 |
| Duration of response, median (95% Cl), months | 5.3 N/A | N/A (5.75-not reached) | 11.8 (4.37-11.83) | N/A |

†No patients dosed at 80 mg REGN1979

After data cut-off (Table 2), two additional evaluable patients showed complete responses (CRs), one at 40 mg and the second at 320 mg.

TABLE 3

| Observed Response in Diffuse Large B-Cell Lymphoma | CD20xCD3† | | | | | |
|---|---|---|---|---|---|---|
| | <5 mg (N = 15) | 5-12 mg (N = 11) | 18-40 mg (N = 11) | 80 mg (N = 3) | 160 mg (N = 3) | 320 mg (N = 2) |
| Overall response rate, n (%) | 2 (13.3) | 2 (18.2) | 6 (54.5) | 3 (100) | 1 (33.3) | 1 (50.0) |
| Complete response, n (%) | 0 | 1 (9.1) | 2 (18.2) | 3 (100) | 1 (33.3) | 1 (50.0) |
| Partial response, n (%) | 2 (13.3) | 1 (9.1) | 4 (36.4) | 0 | 0 | 0 |
| Stable disease, n (%) | 4 (26.7) | 4 (36.4) | 3 (27.3) | 0 | 1 (33.3) | 1 (50.0) |
| Progressive disease, n (%) | 8 (53.3) | 4 (36.4) | 1 (9.1) | 0 | 1 (33.3) | 0 |
| Missing/Unable to Evaluate, n (%) | 1 (6.7) | 1 (9.1) | 1 (9.1) | 0 | 0 | 0 |
| Duration of response, median (95% CI), months | 2.1 (1.5-2.6) | N/A | 4.4 (2.5-not reached) | N/A | N/A | N/A |

Two of three 80 mg patients with CR were CAR T-cell therapy failures. All of the complete responses noted in Table 3 were complete metabolic responses.

All CRs at 80 mg, 160 mg and 320 mg doses are on-going CRs on study treatment, pointing to the durability of response.

TABLE 4

| Observed Response in DLBCL After CAR-T Therapy Failure | CD20xCD3 | | | | |
|---|---|---|---|---|---|
| | 3 mg (N = 1) | 27 mg (N = 1) | 40 mg (N = 1) | 80 mg (N = 3) | 160 mg (N = 1) |
| Overall response rate, n (%) | 0 | 0 | | 2 (66.7) | |
| Complete response, n (%) | 0 | 0 | | 2 (66.7) | |
| Partial response, n (%) | 0 | 0 | | 0 | |
| Stable disease, n (%) | 0 | 1 (100) | | 0 | |
| Progressive disease, n (%) | 1 (100) | 0 | 1 (100) | 1 (33.3) | 1 (100) |
| Missing/Unable to Evaluate, n (%) | 0 | 0 | | 0 | |

TABLE 5

| Observed Response in Mantle Cell Lymphoma | CD20xCD3 | | |
|---|---|---|---|
| | 5-12 mg (N = 1) | 18-40 mg (N = 1) | 160 mg (N = 1) |
| Objective Response (CR/PR) | 1 (100%) | 1 (100%) | 0 |
| Complete response | 0 | 1 (100%) | 0 |
| Partial response | 1 (100%) | 0 | 0 |
| Stable disease | 0 | 0 | 0 |
| Progressive disease | 0 | 0 | 0 |
| Missing/Unable to Evaluate | 0 | 0 | 1 (100%) |

TABLE 6

| Observed Response in Marginal Zone Lymphoma | CD20xCD3 | | |
|---|---|---|---|
| | 5-12 mg (N = 1) | 18-40 mg (N = 1) | 80 mg (N = 3) |
| Objective Response (CR/PR) | 0 | 1 (100%) | 2 (66.7%) |
| Complete response | 0 | 0 | 2 (66.7%) |
| Partial response | 0 | 1 (100%) | 0 |
| Stable disease | 0 | 0 | 0 |
| Progressive disease | 1 (100%) | 0 | 1 (33.3%) |

TABLE 7

| Responses in Patients with MCL by Dose Level | CD20xCD3 | | | | | |
|---|---|---|---|---|---|---|
| | 0.3 mg (N = 1) | 2 mg (N = 1) | 4 mg (N = 1) | 8 mg (N = 1) | 27 mg (N = 1) | 160 mg (N = 1) |
| Objective Response (CR/PR) | 0 | 1 (100%) | 0 | 1 (100%) | 1 (100%) | 1 (100%) |
| Complete Response | 0 | 0 | 0 | 0 | 1 (100%) | 1 (100%) |
| Partial Response | 0 | 1 (100%) | 0 | 1 (100%) | 0 | 0 |
| Stable disease | 0 | 0 | 0 | 0 | 0 | 0 |
| Progressive disease | 1 (100%) | 0 | 1 (100%) | 0 | 0 | 0 |
| Missing/Unable to Evaluate | 0 | 0 | 0 | 0 | 0 | 0 |

TABLE 8

| Responses in Patients with MZL by Dose Level | CD20xCD3 | | | |
|---|---|---|---|---|
| | 4 mg (N = 1) | 5 mg (N = 1) | 27 mg (N = 1) | 80 mg (N = 3) |
| Objective Response (CR/PR) | 1 (100%) | 0 | 1 (100%) | 2 (66.7%) |
| Complete Response | 0 | 0 | 0 | 2 (66.7%) |
| Partial Response | 1 (100%) | 0 | 1 (100%) | 0 |
| Stable disease | 0 | 0 | 0 | 0 |
| Progressive disease | 0 | 1 (100%) | 0 | 1 (33.3%) |
| Missing/Unable to Evaluate | 0 | 0 | 0 | 0 |

TABLE 9

| Responses in Patients with Other-NHL by Dose Level | CD20xCD3 | | | |
|---|---|---|---|---|
| NHL Subtype | 4 mg (N = 1) FL grade unknown | 12 mg (N = 1) Waldenstrom Macroglobulinemia | 18 mg (N = 1) FL grade 3b | 27 mg (N = 1) FL grade unknown |
| Objective Response (CR/PR) | 0 | 0 | 1 (100%) | 0 |

TABLE 9-continued

Responses in Patients with Other-NHL by Dose Level

| NHL Subtype | CD20xCD3 4 mg (N = 1) FL grade unknown | 12 mg (N = 1) Waldenstrom Macroglobulinemia | 18 mg (N = 1) FL grade 3b | 27 mg (N = 1) FL grade unknown |
|---|---|---|---|---|
| Complete Response | 0 | 0 | 1 (100%) | 0 |
| Partial Response | 0 | 0 | 0 | 0 |
| Stable disease | 1 (100%) | 0 | 0 | 0 |
| Progressive disease | 0 | 0 | 0 | 0 |
| Missing/Unable to Evaluate | 0 | 1 (100%) | 0 | 1 (100%) |

In general, activity observed broadly in heavily pretreated relapsed/refractory B-NHL patients treated with REGN1979, including some with progression after prior CAR T-cell therapy, included:

(i) FL Grade 1-3a: 12/13 (92.3%) ORR; 8/13 CR (61.5%) at doses ≥5 mg;

(ii) DLBCL: 4/6 (66.7%) ORR (all CR) at doses of 80-160 mg, with two patients achieving CR after failure of CD19 directed CAR T-cell therapy;

(iii) MCL: 3/3 responses at doses ≥5 mg, including one CR;

(iv) MZL: 3/5 response at doses ≥5 mg, including two CRs;

(v) Tolerability in patients with B-NHL has been demonstrated up to doses of 320 mg weekly, with no observed DLTs in patients with B-NHL;

(vi) Majority of adverse events with mild to moderate in severity;

(vii) Infections were reported in 49.4% of patients (14.8% Grade 3-4, with two deaths (2.5%));

(viii) No patient discontinued treatment due to CRS or neurologic adverse events. Of 96 initial patients, only seven patients experienced Grade 3 CRS; and (ix) Dexamethasone did not inhibit cytotoxicity of REGN1979, modestly affected upregulation of T-cell activation, and inhibited cytokine release.

Example 2: Clinical Evaluation of a Bispecific Antibody

The below-described clinical study is an open-label multicenter phase 2 study to assess the anti-tumor activity and safety of REGN1979, an anti-CD20×anti-CD3 bispecific antibody, in patients with relapsed or refractory follicular lymphoma.

Objectives: The primary objective of this study is to assess the anti-tumor activity of single agent REGN1979, as measured by objective response rate (ORR) according to the Lugano Classification of response in malignant lymphoma (Cheson, 2014) by independent central review, in patients with follicular lymphoma (FL) that has relapsed or is refractory to at least 2 prior lines of systemic therapy, including an anti-CD20 antibody and an alkylating agent. The secondary objectives in this study are: (1) to assess the anti-tumor activity of single agent REGN1979 in patients with relapsed or refractory FL, as measured by (a) ORR according to the Lugano Classification (Cheson, 2014) as assessed by local investigator evaluation, (b) complete response (CR) rate according to the Lugano Classification as assessed by independent central review, and local investigator evaluation, (c) progression free survival (PFS) according to Lugano Classification as assessed by independent central review, and local investigator evaluation, (d) overall survival (OS), (e) duration of response (DOR) according to the Lugano Classification as assessed by independent central review, and local investigator evaluation, (f) disease control rate (DCR) according to the Lugano Classification as assessed by independent central review, and local investigator evaluation, (g) duration of disease control (DDC) according to the Lugano Classification as assessed by independent central review, and local investigator evaluation; (2) to evaluate the safety and tolerability of REGN1979; (3) to assess the pharmacokinetics (PK) of REGN1979; (4) to assess the immunogenicity of REGN1979; and (5) to assess the effect of REGN1979 on quality of life as measured by the validated instruments European Organisation for Research and Treatment of Cancer Quality of Life Questionnaire (EORTC QLQ-C30) and EuroQoL 5 Dimensions 3 Levels (EQ-5D-3L).

Study Design: the study consists of a screening period of up to 28 days, a total treatment period of up to 98 weeks that includes 12 weekly (QW) doses followed by every 2-week (Q2W) dosing of up to 86 weeks, and a post-treatment follow-up period of 96 weeks.

REGN1979 is administered as a single agent intravenously (IV) at an initial (primary) dose of 1 mg, followed by an intermediate (secondary) dose of 20 mg, and subsequently by a nominal (tertiary and maximum weekly) dose of 80 mg in a dosing regimen of 12 QW treatments, followed by dosing of 80 mg REGN1979 Q2W.

Enrollment follows an open-label, single-arm design.

The screening period begins with the signing of the informed consent form (ICF) and ends when the patient has been confirmed to be eligible for the study and initiates treatment, or with the determination that the patient is ineligible and has been designated as a screen failure.

The treatment period begins with the initial administration of REGN1979 and consists of 12 QW infusions of REGN1979 followed by Q2W dosing for 86 weeks for a total treatment period of 98 weeks of study drug dosing, unless the patient discontinues study treatment due to disease progression, start of subsequent lymphoma therapy, adverse event (AE), or any other reason.

The post-treatment follow-up period will be for 96 weeks after the last dose of study treatment. All patients will be followed every 12 weeks for survival status until death, loss to follow-up, patient withdrawal of consent for follow-up, or study termination by the sponsor, whichever is sooner. For patients who have discontinued study treatment for any reason other than disease progression, start of subsequent lymphoma therapy, or death, disease response will be assessed every 12 weeks during the post-treatment follow-up period until the time of disease progression, death, start of a subsequent lymphoma therapy, or patient withdrawal of consent for follow-up, whichever is sooner.

Study Duration: The duration of the study for each patient, excluding the screening period, will be approximately 194 weeks unless the patient has disease progression or starts subsequent therapy, or until the time of death, loss to follow-up, patient withdrawal of consent for follow-up, or study termination by the sponsor. The end of study is defined as the last visit of the last patient.

Study Population: Up to 481 patients will be enrolled at up to 100 sites. The study population will consist of patients aged 18 years and older with previously treated FL grade 1 to 3a that has relapsed or is refractory to at least 2 prior lines of systemic therapy, including an anti-CD20 antibody and an alkylating agent. Central histopathologic confirmation of the FL diagnosis will be required prior to enrollment. Patients with FL grade 3b are ineligible. Refractory disease is defined as lack of response to a standard regimen or progression within 6 months of last treatment.

Inclusion Criteria: Each patient must meet the following criteria to be eligible for inclusion in the study:

1. Age 18 years or greater

2. Central histopathologic confirmation of the FL Grade 1 to 3a diagnosis must be obtained before study enrollment. Patients with FL grade 3b are ineligible. Follicular lymphoma subtyping is based on the World Health Organization (WHO) classification (Swerdlow, 2017).

3. Disease must have relapsed or must be refractory to ≥2 prior lines of systemic therapy, including an anti-CD20 antibody and an alkylating agent. Patients should in the opinion of the investigator require therapy for FL at the time of study enrollment.

4. Measurable disease on cross sectional imaging (defined as at least 1 bi-dimensionally measurable nodal lesion of ≥1.5 cm in the greatest transverse diameter (GTD) regardless of the short axis diameter) documented by diagnostic imaging (computed tomography [CT], or magnetic resonance imaging [MRI]).

5. Eastern Cooperative Oncology Group (ECOG) performance status 0 or 1.

6. Adequate bone marrow function as documented by: (a) Platelet count ≥50×$10^9$/L. A patient may not have received platelet transfusion within 7 days prior to first dose of REGN1979 in order to meet the platelet eligibility criterion; (b) Hemoglobin ≥9.0 g/dL; (c) Absolute neutrophil count (ANC) ≥1.0×$10^9$/L. A patient may not have received granulocyte colony stimulating factor within 2 days prior to first dose of REGN1979 in order to meet the ANC eligibility criterion.

7. Adequate hepatic function: (a) Total bilirubin ≤1.5× upper limit of normal (ULN) (≤3×ULN if attributed to lymphoma infiltration of liver); (b) Alanine aminotransferase (ALT) and aspartate aminotransferase (AST) ≤2.5×ULN (≤5×ULN if attributed to lymphoma infiltration of liver); (c) Alkaline phosphatase (ALP) ≤2.5×ULN (≤5×ULN if attributed to lymphoma infiltration of liver); NOTES—Irrespective of the presence of lymphoma infiltration of the liver, a patient with an AST >2.5×ULN and/or ALT >2.5×ULN concurrent with a total bilirubin >1.5×ULN will be excluded, and Patients with known Gilbert syndrome are not required to meet this total bilirubin requirement provided that the value is unchanged from the baseline level.

8. Serum creatinine ≤1.5×ULN, or calculated creatinine clearance by Cockcroft-Gault formula ≥50 mL/min; NOTE—Patients with a calculated creatinine clearance <50 mL/min may be considered for enrollment if a measured creatinine clearance (based on 24-hour urine collection or other reliable method) is ≥50 mL/min.

9. Willingness to undergo tumor biopsy at baseline. If an investigator has determined that a baseline tumor biopsy cannot be obtained safely, the sponsor may grant an exception to the requirement for biopsy only after discussion with and approval by the medical monitor.

10. Ability to understand the purpose and risks of the study and provide signed and dated informed consent and authorization to use protected health information (in accordance with national and local subject privacy regulations).

11. Willing and able to comply with clinic visits and study-related procedures.

12. Provide informed consent signed by study patient or legally acceptable representative.

13. Able to understand and complete study-related questionnaires.

Exclusion Criteria: A patient who meets any of the following criteria will be excluded from the study:

1. Primary central nervous system (CNS) lymphoma or known involvement by non-primary CNS NHL (suspected CNS lymphoma should be evaluated by lumbar puncture, as appropriate, in addition to the mandatory head CT or MRI).

2. Treatment with any systemic anti-lymphoma therapy within 5 half-lives or within 28 days prior to first administration of study drug, whichever is shorter.

3. History of allogeneic stem cell transplantation.

4. Prior treatment with any chimeric antigen receptor T-cell (CAR-T) therapy.

5. Continuous systemic corticosteroid treatment with more than 10 mg per day of prednisone or anti-inflammatory equivalent within 72 hours of start of study drug.

6. History of neurodegenerative condition or CNS movement disorder. History of uncontrolled seizure disorder, defined as any seizure within 12 months prior to study enrollment.

7. Vaccination within 28 days prior to first study drug administration with a vector that has replicative potential.

8. Another malignancy except FL in the past 5 years, with the exception of non-melanoma skin cancer that has undergone potentially curative therapy or in situ cervical carcinoma, or any other tumor that has been deemed to be effectively treated with definitive local control and with curative intent.

9. Evidence of significant concurrent disease or medical condition that could interfere with the conduct of the study or put the patient at significant risk, including but not limited to significant cardiovascular disease (e.g., New York Heart Association Class III or IV cardiac disease, myocardial infarction within the previous 6 months, unstable arrhythmias, or unstable angina) and/or significant pulmonary disease (e.g., obstructive pulmonary disease and history of symptomatic bronchospasm).

10. Cardiac ejection fraction <40% by echocardiogram or multigated acquisition (MUGA) scan.

11. Any infection requiring hospitalization or treatment with IV anti-infectives within 2 weeks of first administration of study drug.

12. Uncontrolled infection with human immunodeficiency virus (HIV), hepatitis B or hepatitis C infection; or other uncontrolled infection, except: (a) Patients with HIV who have controlled infection (undetectable viral load and CD4 count above 350 cells/microliter either spontaneously or on a stable antiviral regimen) are permitted; (b) Patients with hepatitis B (HepBsAg+) who have controlled infection (serum hepatitis B virus DNA polymerase chain reaction [PCR] that is below the limit of detection AND receiving anti-viral therapy for hepatitis B) are permitted; (c) Patients who are hepatitis C virus antibody positive (HCV Ab+) who have controlled infection (undetectable HCV RNA by PCR either spontaneously or in response to a successful prior course of anti-HCV therapy) are permitted.

13. History of severe allergic reaction attributed to compounds with a similar chemical or biologic composition as that of the study drug or excipient. A severe allergic reaction is defined for this purpose as that requiring hospitalization and/or treatment with epinephrine.

14. Known hypersensitivity to both allopurinol and rasburicase.

15. Member of the clinical site study team or his/her immediate family, unless prior approval granted by the sponsor.

16. Women with a positive serum β-hCG pregnancy test at the screening visit. If positive, pregnancy must be ruled out by ultrasound for patient to be eligible.

17. Patients who are committed to an institution by virtue of an order issued either by the judicial or the administrative authorities.

18. Pregnant or breastfeeding women.

19. Women of childbearing potential* or men who are unwilling to practice highly effective contraception prior to the initial dose/start of the first treatment, during the study, and for at least 6 months after the last dose. Highly effective contraceptive measures include: (a) stable use of combined (estrogen and progestogen containing) hormonal contraception (oral, intravaginal, transdermal) or progestogen-only hormonal contraception (oral, injectable, implantable) associated with inhibition of ovulation initiated 2 or more menstrual cycles prior to screening; (b) intrauterine device (IUD); intrauterine hormone-releasing system (IUS); (c) bilateral tubal ligation; (d) vasectomized partner; (e) and/or sexual abstinences[†, ‡].

Postmenopausal women must be amenorrheic for at least 12 months in order not to be considered of childbearing potential. Pregnancy testing and contraception are not required for women with documented hysterectomy or tubal ligation.

[†] Sexual abstinence is considered a highly effective method only if defined as refraining from heterosexual intercourse during the entire period of risk associated with the study drugs. The reliability of sexual abstinence needs to be evaluated in relation to the duration of the clinical trial and the preferred and usual lifestyle of the subject.

[‡] Periodic abstinence (calendar, symptothermal, post-ovulation methods), withdrawal (coitus interruptus), spermicides only, and lactational amenorrhoea method (LAM) are not acceptable methods of contraception. Female condom and male condom should not be used together.

Treatment: REGN1979 will be administered by IV infusion at an initial dose of 1 mg during week 1, an intermediate dose of 20 mg during week 2, and a nominal dose of 80 mg or 160 mg during subsequent administrations. For the initial dose, intermediate dose and first nominal dose (primary, secondary and tertiary doses, respectively), the treatments will be split into 2 separate infusions, each over 4 hours on each of 2 days that are preferably consecutive but no more than 3 days apart (e.g., week 1 day 1 and week 1 day 2). Subsequent treatments (maximum weekly doses; e.g., 320 mg) may be administered as a single infusion or as 2 separate infusions and may be administered over 1 to 4 hours depending on tolerability. Study treatment comprises 12 QW administrations followed by Q2W dosing for 86 weeks, for a total of 98 weeks of study drug dosing.

Endpoints: The primary endpoint of the study is ORR from first dose until 194 weeks following the first dose, as measured by the Lugano Classification of response in malignant lymphoma (Cheson, 2014) and according to independent central review, in patients with FL that has relapsed or is refractory to at least 2 prior lines of systemic therapy, including an anti-CD20 antibody and an alkylating agent. The secondary endpoints are: (1) ORR according to the Lugano Classification as assessed by local investigator evaluation from first dose up to 194 weeks following the first dose; (2) CR rate from first dose until 194 weeks following the first dose, according to the Lugano Classification, as assessed by independent central review, and local investigator evaluation; (3) PFS from first dose until 194 weeks following the first dose, according to the Lugano Classification, as assessed by independent central review, and local investigator evaluation; (4) OS from first dose up to until 194 weeks following the first dose; (5) DOR from first dose until 194 weeks following the first dose, according to the Lugano Classification, as assessed by independent central review, and local investigator evaluation; (6) DCR from first dose until 194 weeks following first dose, according to the Lugano Classification, as assessed by independent central review, and local investigator evaluation; (7) DDC from first dose until 194 weeks following the first dose, according to the Lugano Classification, as assessed by independent central review, and local investigator evaluation; (8) Incidence and severity of treatment-emergent adverse events (TEAEs) from first dose until 194 weeks following the first dose; and (9) Changes in scores of patient-reported outcomes from first dose until 194 weeks following the first dose as measured by the validated instruments EORTC QLQ-C30 and EQ-5D-3L.

Procedures and Assessments: For all patients, disease will be assessed radiologically using computed tomography (CT) or magnetic resonance imaging (MRI) and by $^{18}$F-fluorodeoxyglucose-positron emission tomography (FDG-PET) imaging. Tumor response according to the Lugano Classification criteria will be adjudicated by independent central radiology review. Bone marrow aspirate, bone marrow biopsy, and lymph node and/or tumor biopsy will be performed, and samples will be evaluated histologically and may be used for other studies, including for immunohistochemistry. Safety will be evaluated by the assessment of vital signs, physical examination, Eastern Cooperative Oncology Group (ECOG) performance status, electrocardiogram (ECG), incidence of AEs, and reporting of concomitant medications. Laboratory evaluations include complete blood count with differential, blood chemistry values, serum immunoglobulins G (IgG), serum pregnancy testing (if relevant), ferritin, and C-reactive protein (CRP). Blood samples for PK and anti-drug antibody (ADA) assessment will be collected. Peripheral blood samples will be collected to assess changes in biomarkers (e.g., cytokine production, serum levels of pro-inflammatory cytokines, and changes in lymphocyte subsets and activation status). In addition, these samples will permit tumor or somatic genetic analyses for variations that impact the clinical course of underlying disease or modulate treatment side effects. Quality of life assessments will be performed using the self-administered EORTC QLQ-C30 and EQ-5D-3L questionnaires.

Statistical Plan: This study is designed to evaluate the efficacy and safety of REGN1979 for patients with FL that has relapsed or is refractory to at least 2 prior lines of systemic therapies. The analysis for the primary efficacy endpoint will be performed after all the patients completed 28 weeks of study treatment period to assessments and have had an assessment of tumor responses or have withdrawn from the study. Justification of Sample Size—a single-stage exact binomial design is adopted for the primary endpoint of ORR. The 2-sided 95% confidence intervals for the observed ORRs were calculated based on the sample size 100. With 100 patients, if the observed ORR is at least 60%, 66%, 70%, and 75%, the lower limit of 95% CI will exclude the ORR of 49%, 55%, 60%, and 65% respectively; ie, the ORR is significantly different from 49%, 55%, 60%, and 65% as shown in Table 10, below.

TABLE 10

The 2-sided 95% Exact Confidence Intervals for Observed ORR Given a Sample Size of 100 Patients

| Number of Responders | Observed ORR | 95% CI-lower | 95% CI-upper |
|---|---|---|---|
| 60 | 0.60 | 0.497 | 0.697 |
| 66 | 0.66 | 0.558 | 0.752 |
| 70 | 0.70 | 0.6002 | 0.788 |
| 75 | 0.75 | 0.653 | 0.831 |

With the sample size of 100 patients, if the true treatment effect of REGN1979 is 64%, 70%, 75%, or 80%, the probability is 82%, 83%, 89%, or 91% for observed lower bound of 95% CI to exclude 49%, 55%, 60%, or 65% respectively. The sample size will be further increased by 10% to account for patients who withdraw prematurely from the study. Hence, the total sample size will be 112 patients.

Statistical Methods: Demographic and baseline characteristics will be summarized descriptively. The primary efficacy endpoint is the ORR according to the Lugano Classification based on independent central review. The ORR along with the 2-sided 95% confidence interval will be summarized. Patients who are not evaluable for the best overall response will be considered as non-responders. The secondary efficacy endpoints of ORR as determined by investigator review according to Lugano Classification, and the CR rate and DCR by local investigator evaluation and by independent central review according to the Lugano Classification will be summarized along with 2-sided 95% confidence interval. The other secondary efficacy endpoints, including DOR, DDC, PFS, and OS will be summarized by median and its 95% confidence interval using the Kaplan-Meier method according to Lugano Classification. Disease control rate will be summarized along with 2-sided confidence interval. Quality of life measured by validated instruments EORTC QLQ-C30 and EQ-5D-3L will be summarized by descriptive statistics. Safety observations and measurements including drug exposure, AEs, laboratory data, vital signs, and ECOG performance status will be summarized and presented in tables and listings.

Interim Analysis: An interim analysis will be performed after the first 50 patients have completed tumor assessments at 28 weeks or have withdrawn from the study earlier. The ORR and associated 95% confidence interval will be summarized. As the primary objective of this interim analysis is point estimation on ORR and characterizing the precision of point estimation, there is no hypothesis testing associated with this interim analysis. Therefore, Type I error adjustment is not applicable for this planned interim analysis. For other efficacy endpoints, 2-sided 95% confidence interval will also be presented.

Additional efficacy investigations of REGN1979 may be included in the present study, or in additional studies, including in (a) patients with follicular lymphoma (grade 1-3a) as third line or greater (3L+) therapy, (b) patients with follicular lymphoma (grade 1-3a) that are fit for full dose chemotherapy as second line or greater (2L+) therapy, (c) patients with follicular lymphoma (grade 1-3a) that are unfit for full dose chemotherapy as 2L+ therapy, (d) patients with follicular lymphoma (grade 1-3a) that are previously untreated and fit for full dose chemo-immunotherapy, (e) patients with follicular lymphoma (grade 1-3a) that are previously untreated and unfit for full dose chemo-immunotherapy, (f) patients with follicular lymphoma (grade 1-3a) fit for full dose chemo-immunotherapy as first line (1L) therapy versus standard of care, (g) patients with follicular lymphoma (grade 1-3a) unfit for full dose chemo-immunotherapy as 1L therapy versus standard of care, (h) patients with follicular lymphoma (grade 1-3a) fit for full dose chemo-immunotherapy as 2L+ therapy versus standard of care, (i) patients with follicular lymphoma (grade 1-3a) unfit for full dose chemo-immunotherapy as 2L+ therapy versus standard of care, and/or (j) patients with follicular lymphoma in combination with standard of care.

Additional efficacy investigations of REGN1979 may be included in the present study, or in additional studies, including in (a) patients with diffuse large B-cell lymphoma (DLBCL) that is de novo or transformed as 3L+ therapy, (b) patients with DLBCL following failure of CAR-T therapy, (c) patients with DLBCL eligible for autologous HSCT (hematopoietic stem cell transplantation) as 2L+ therapy, (d) patients with DLBCL ineligible for HSCT as 2L+ therapy, (e) patients with DLBCL that are previously untreated, with poor molecular prognostic factors (non-germinal center B, double hit or triple hit) and fit for full dose chemo-immunotherapy, (f) patients with DLBCL that are previously untreated, poor molecular prognostic factors (non-germinal center B, double hit or triple hit) and unfit for full dose chemo-immunotherapy, (g) patients with DLBCL that are CAR-T naïve, (h) patients with DLBCL at a maximum weekly dose of 320 mg, (i) patients with DLBCLin combination with standard of care, (j) patients with DLBCL for for full dose chemo-immunotherapy as 1L therapy versus standard of care, (k) patients with DLBCL unfit for full dose chemo-immunotherapy as 1L therapy versus standard of care, (l) patients with DLBCL that are eligible for auto-HSCT as 2L+ therapy versus standard of care, and/or (m) patients with DLBCL that are ineligible for auto-HSCT as 2L+ therapy versus standard of care.

Additional efficacy investigations of REGN1979 may be included in the present study, or in additional studies, including in (a) patients with mantle cell lymphoma (MCL) following BTK inhibitor failure as 2L+ therapy, (b) in patients with marginal zone lymphoma (MZL) as 2L+ therapy, and/or (c) in patients with lymphoblastic lymphoma, lymphoplasmacytic lymphoma, Burkitt lymphoma, or other B-NHL subtypes as 2L+ therapy.

Additional efficacy investigations of REGN1979 may be included in the present study, or in additional studies, including in (a) patients with a CD20+ B-cell malignancy that have received a single dose of rituximab one day prior to the first dose of REGN1979. In this rituximab lead-in cohort and expansion only, a single dose of rituximab (375 $mg/m^2$) will be administered one day prior to the first dose of REGN1979 [i.e, on study day (−1)]. REGN1979 will be started on Week 1 Day 1, and the treatment period for REGN1979 will be 9 months. Patients will be treated with up to 24 doses of REGN1979: 4 weekly doses during a 4-week induction period, followed by an additional 8 weekly doses, and 12 doses administered Q2W during a 6-month maintenance period. In the first part of this rituximab lead-in cohort, REGN1979 will be administered using a step-up dose of 80 mg. Once an optimal dose regimen is identified, one additional dose group of 6 patients at a step-up dose of 320 mg REGN1979 will be evaluated with the optimal dose regimen. Dose groups with step-up doses of REGN1979 between 80 mg and 320 mg may be evaluated also. Subsequently, an additional 24 patients will be evaluated with this optimal dose regimen and optimal dose, and together with the 6 patients in the rituximab lead-in group treated at the optimal dose a total of 30 patients will be reviewed for safety and tolerability.

In any of the combination studies with standard of care, the combination may include REGN1979 plus CHOP (cyclophosphamide, doxorubicin, vincristine and prednisone), ICE (ifosfamide, carboplatin and etoposide), Gem-Ox (gemcitabine and oxaliplatin), lenalidomide, or lenalidomide plus rituximab.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

TABLE 11

| Sequences Excluded from ST.26-Formatted Sequence Listing | |
|---|---|
| SEQID NO: | Sequence |
| 23 | GAS |

SEQUENCE LISTING

```
Sequence total quantity: 24
SEQ ID NO: 1          moltype = AA  length = 207
FEATURE               Location/Qualifiers
REGION                1..207
                      note = human CD3 Epsilon Protein (NP_000724.1 T-cell
                       surface glycoprotein CD3 epsilon chain precursor
source                1..207
                      mol_type = protein
                      organism = synthetic construct
SEQUENCE: 1
MQSGTHWRVL GLCLLSVGVW GQDGNEEMGG ITQTPYKVSI SGTTVILTCP QYPGSEILWQ  60
HNDKNIGGDE DDKNIGSDED HLSLKEFSEL EQSGYYVCYP RGSKPEDANF YLYLRARVCE  120
NCMEMDVMSV ATIVIVDICI TGGLLLLVYY WSKNRKAKAK PVTRGAGAGG RQRGQNKERP  180
PPVPNPDYEP IRKGQRDLYS GLNQRRI                                    207

SEQ ID NO: 2          moltype = AA  length = 171
FEATURE               Location/Qualifiers
REGION                1..171
                      note = human CD3 Delta Protein (NP_000723.1 T-cell surface
                       glycoprotein CD3 delta chain isoform A precursor
source                1..171
                      mol_type = protein
                      organism = synthetic construct
SEQUENCE: 2
MEHSTFLSGL VLATLLSQVS PFKIPIEELE DRVFVNCNTS ITWVEGTVGT LLSDITRLDL  60
GKRILDPRGI YRCNGTDIYK DKESTVQVHY RMCQSCVELD PATVAGIIVT DVIATLLLAL  120
GVFCFAGHET GRLSGAADTQ ALLRNDQVYQ PLRDRDDAQY SHLGGNWARN K          171

SEQ ID NO: 3          moltype = AA  length = 164
FEATURE               Location/Qualifiers
REGION                1..164
                      note = human CD3 Zeta Protein (NP_932170.1 T-cell surface
                       glycoprotein CD3 zeta chain isoform 1 precursor
source                1..164
                      mol_type = protein
                      organism = synthetic construct
SEQUENCE: 3
MKWKALFTAA ILQAQLPITE AQSFGLLDPK LCYLLDGILF IYGVILTALF LRVKFSRSAD  60
APAYQQGQNQ LYNELNLGRR EEYDVLDKRR GRDPEMGGKP QRRKNPQEGL YNELQKDKMA  120
EAYSEIGMKG ERRRGKGHDG LYQGLSTATK DTYDALHMQA LPPR                  164

SEQ ID NO: 4          moltype = AA  length = 182
FEATURE               Location/Qualifiers
REGION                1..182
                      note = human CD3 Gamma Protein (NP_000064.1 T-cell surface
                       glycoprotein CD3 gamma chain precursor
source                1..182
                      mol_type = protein
                      organism = synthetic construct
SEQUENCE: 4
MEQGKGLAVL ILAIILLQGT LAQSIKGNHL VKVYDYQEDG SVLLTCDAEA KNITWFKDGK  60
MIGFLTEDKK KWNLGSNAKD PRGMYQCKGS QNKSKPLQVY YRMCQNCIEL NAATISGFLF  120
AEIVSIFVLA VGVYFIAGQD GVRQSRASDK QTLLPNDQLY QPLKDREDDQ YSHLQGNQLR  180
RN                                                               182

SEQ ID NO: 5          moltype = AA  length = 297
FEATURE               Location/Qualifiers
REGION                1..297
                      note = human CD20 Protein
source                1..297
                      mol_type = protein
                      organism = synthetic construct
SEQUENCE: 5
MTTPRNSVNG TFPAEPMKGP IAMQSGPKPL FRRMSSLVGP TQSFFMRESK TLGAVQIMNG  60
```

```
LFHIALGGLL MIPAGIYAPI CVTVWYPLWG GIMYIISGSL LAATEKNSRK CLVKGKMIMN  120
SLSLFAAISG MILSIMDILN IKISHFLKME SLNFIRAHTP YINIYNCEPA NPSEKNSPST  180
QYCYSIQSLF LGILSVMLIF AFFQELVIAG IVENEWKRTC SRPKSNIVLL SAEEKKEQTI  240
EIKEEVVGLT ETSSQPKNEE DIEIIPIQEE EEEETETNFP EPPQDQESSP IENDSSP     297

SEQ ID NO: 6           moltype = AA  length = 184
FEATURE                Location/Qualifiers
REGION                 1..184
                       note = human BCMA (TNFRSF17) Protein NP_001183.2
source                 1..184
                       mol_type = protein
                       organism = synthetic construct
SEQUENCE: 6
MLQMAGQCSQ NEYFDSLLHA CIPCQLRCSS NTPPLTCQRY CNASVTNSVK GTNAILWTCL  60
GLSLIISLAV FVLMFLLRKI NSEPLKDEFK NTGSGLLGMA NIDLEKSRTG DEIILPRGLE  120
YTVEECTCED CIKSKPKVDS DHCFPLPAME EGATILVTTK TNDYCKSLPA ALSATEIEKS  180
ISAR                                                              184

SEQ ID NO: 7           moltype = AA  length = 750
FEATURE                Location/Qualifiers
REGION                 1..750
                       note = human PSMA (FOLH1) Protein
source                 1..750
                       mol_type = protein
                       organism = synthetic construct
SEQUENCE: 7
MWNLLHETDS AVATARRPRW LCAGALVLAG GFFLLGFLFG WFIKSSNEAT NITPKHNMKA  60
FLDELKAENI KKFLYNFTQI PHLAGTEQNF QLAKQIQSQW KEFGLDSVEL AHYDVLLSYP  120
NKTHPNYISI INEDGNEIFN TSLFEPPPPG YENVSDIVPP FSAFSPQGMP EGDLVYVNYA  180
RTEDFFKLER DMKINCSGKI VIARYGKVFR GNKVKNAQLA GAKGVILYSD PADYFAPGVK  240
SYPDGWNLPG GGVQRGNILN LNGAGDPLTP GYPANEYAYR RGIAEAVGLP SIPVHPIGYY  300
DAQKLLEKMG GSAPPDSSWR GSLKVPYNVG PGFTGNFSTQ KVKMHIHSTN EVTRIYNVIG  360
TLRGAVEPDR YVILGGHRDS WVFGGIDPQS GAAVVHEIVR SFGTLKKEGW RPRRTILFAS  420
WDAEEFGLLG STEWAEENSR LLQERGVAYI NADSSIEGNY TLRVDCTPLM YSLVHNLTKE  480
LKSPDEGFEG KSLYESWTKK SPSPEFSGMP RISKLGSGND FEVFFQRLGI ASGRARYTKN  540
WETNKFSGYP LYHSVYETYE LVEKFYDPMF KYHLTVAQVR GGMVFELANS IVLPFDCRDY  600
AVVLRKYADK IYSISMKHPQ EMKTYSVSFD SLFSAVKNFT EIASKFSERL QDFDKSNPIV  660
LRMMNDQLMF LERAFIDPLG LPDRPFYRHV IYAPSSHNKY AGESFPGIYD ALFDIESKVD  720
PSKAWGEVKR QIYVAAFTVQ AAAETLSEVA                                  750

SEQ ID NO: 8           moltype = AA  length = 14507
FEATURE                Location/Qualifiers
REGION                 1..14507
                       note = human MUC16 (CA-125) Protein
source                 1..14507
                       mol_type = protein
                       organism = synthetic construct
SEQUENCE: 8
MLKPSGLPGS SSPTRSLMTG SRSTKATPEM DSGLTGATLS PKTSTGAIVV TEHTLPFTSP  60
DKTLASPTSS VVGRTTQSLG VMSSALPEST SRGMTHSEQR TSPSLSPQVN GTPSRNYPAT  120
SMVSGLSSPR TRTSSTEGNF TKEASTYTLT VETTSGPVTE KYTVPTETST TEGDSTETPW  180
DTRYIPVKIT SPMKTFADST ASKENAPVSM TPAETTVTDS HTPGRTNPSF GTLYSSFLDL  240
SPKGTPNSRG ETSLELILST TGYPFSSPEP GSAGHSRIST SAPLSSSASV LDNKISETSI  300
FSGQSLTSPL SPGVPEARAS TMPNSAIPFS MTLSNAETSA ERVRSTISSL GTPSISTKQT  360
AETILTFHAF AETMDIPSTH IAKTLASEWL GSPGTLGGTS TSALTTTSPS TTLVSEETNT  420
HHSTSGKETE GTLNTSMTPL ETSAPGEESE MTATLVPTLG FTTLDSKIRS PSQVSSSHPT  480
RELRTTGSTS GRQSSSTAAH GSSDILRATT SSTSKASSWT SESTAQQFSE PQHTQWVETS  540
PSMKTERPPA STSVAAPITT SVPSVVSGFT TLKTSSTKGI WLEETSADTL IGESTAGPTT  600
HQFAVPTGIS MTGGSSTRGS QGTTHLLTRA TASSETSADL TLATNGVPVS VSPAVSKTAA  660
GSSPPGGTKP SYTMVSSVIP ETSSLQSSAF REGTSLGLTP LNTRHPFSSP EPDSAGHTKI  720
STSIPLLSSA SVLEDKVSAT STFSHHKATS SITTGTPEIS TKTKPSSAVL SSMTLSNAAT  780
SPERVRNATS PLTHPSPSGE ETAGSVLTLS TSAETTDSPN IHPTGTLTSE SSESPSTLSL  840
PSVSGVKTTF SSSTPSTHLF TSGEETEETS NPSVSQPETS VSRVRTTLAS TSVPTPVFPT  900
MDTWPTRSAQ FSSSHLVSEL RATSSTSVTN STGSALPKIS HLTGTATMSQ TNRDTFNDSA  960
APQSTTWPET SPRFKTGLPS ATTTVSTSAT SLSATVMVSK FTSPATSSME ATSIREPSTT  1020
ILTTETTNGP GSMAVASTNI PIGKGYITEG RLDTSHLPIG TTASSETSMD FTMAKESVSM  1080
SVSPSQSMDA AGSSTPGRTS QFVDTFSDDV YHLTSREITI PRDGTSSALT PQMTATHPPS  1140
PDPGSARSTW LGILSSSPSS PTPKVTMSST FSTQRVTTSM IMDTVETSRW NMPNLPSTTS  1200
LTPSNIPTSG AIGKSTLVPL DTPSPATSLE ASEGGLPTLS TYPESTNTPS IHLGAHASSE  1260
SPSTIKLTMA SVVKPGSYTP LTFPSIETHI HVSTARMAYS SGSSPEMTAP GETNTGSTWD  1320
PTTYITTTDP KDTSSAQVST PHSVRTLRTT ENHPKTESAT PAAYSGSPKI SSSPNLTSPA  1380
TKAWTITDTT EHSTQLHYTK LAEKSSGFET QSAPGPVSVV IPTSPTIGSS TLELTSDVPG  1440
EPLVLAPSEQ TTITLPMATW LSTSLTEEMA STDLDISSPS SPMSTFAIFP PMSTPSHELS  1500
KSEADTSAIR NTDSTTLDQH LGIRSLGRTG DLTTVPITPL TTTWTSVIEH STQAQDTLSA  1560
TMSPTHVTQS LKDQTSIPAS ASPSHLTEVY PELGTQGRSS SEATTFWKPS TDTLSREIET  1620
GPTNIQSTPP MDNTTTGSSS SGVTLGIAHL PIGTSSPAET STNMALERRS STATVSMAGT  1680
MGLLVTSAPG RSISQSLGRV SSVLSESTTE GVTDSSKGSS PRLNTQGNTA LSSSLEPSYA  1740
EGSQMSTSIP LTSSPTTPDV EFIGGSTFWT KEVTTVMTSD ISKSSARTES SSATLMSTAL  1800
GSTENTGKEK LRTASMDLPS PTPSMEVTPW ISLTLSNAPN TTDSLDLSHG VHTSSAGTLA  1860
```

-continued

```
TDRSLNTGVT RASRLENGSD TSSKSLSMGN STHTSMTYTE KSEVSSSIHP RPETSAPGAE  1920
TTLTSTPGNR AISLTLPFSS IPVEEVISTG ITSGPDINSA PMTHSPITPP TIVWTSTGTI  1980
EQSTQPLHAV SSEKVSVQTQ STPYVNSVAV SASPTHENSV SSGSSTSSPY SSASLESLDS  2040
TISRRNAITS WLWDLTTSLP TTTWPSTSLS EALSSGHSGV SNPSSTTTEF PLFSAASTSA  2100
AKQRNPETET HGPQNTAAST LNTDASSVTG LSETPVGASI SSEVPLPMAI TSRSDVSGLT  2160
SESTANPSLG TASSAGTKLT RTISLPTSES LVSFRMNKDP WTVSIPLGSH PTTNTETSIP  2220
VNSAGPPGLS TVASDVIDTP SDGAESIPTV SFSPSPDTEV TTISHFPEKT THSFRTISSL  2280
THELTSRVTP IPGDWMSSAM STKPTGASPS ITLGERRTIT SAAPTTSPIV LTASFTETST  2340
VSLDNETTVK TSDILDARKT NELPSDSSSS SDLINTSIAS STMDVTKTAS ISPTSISGMT  2400
ASSSPSLFSS DRPQVPTSTT ETNTATSPSV SSNTYSLDGG SNVGGTPSTL PPFTITHPVE  2460
TSSALLAWSR PVRTFSTMVS TDTASGENPT SSNSVVTSVP APGTWTSVGS TTDLPAMGFL  2520
KTSPAGEAHS LLASTIEPAT AFTPHLSAAV VTGSSATSEA SLLTTSESKA IHSSPQTPTT  2580
PTSGANWETS ATPESLLVVT ETSDTTLTSK ILVTDTILFS TVSTPPSKFP STGTLSGASF  2640
PTLLPDTPAI PLTATEPTSS LATSFDSTPL VTIASDSLGT VPETTLTMSE TSNGDALVLK  2700
TVSNPDRSIP GITIQGVTES PLHPSSTSPS KIVAPRNTTY EGSITVALST LPAGTTGSLV  2760
FSQSSENSET TALVDSSAGL ERASVMPLTT GSQGMASSGG IRSGSTHSTG TKTFSSLPLT  2820
MNPGEVTAMS EITTNRLTAT QSTAPKGIPV KPTSAESGLL TPVSASSSPS KAFASLTTAP  2880
PTWGIPQSTL TFEFSEVPSL DTKSASLPTP GQSLNTIPDS DASTASSSLS KSPEKNPRAR  2940
MMTSTKAISA SSFQSTGFTE TPEGSASPSM AGHEPRVPTS GTGDPRYASE SMSYPDPSKA  3000
SSAMTSTSLA SKLTTLFSTG QAARSGSSSS PISLSTEKET SFLSPTASTS RKTSLFLGPS  3060
MARQPNILVH LQTSALTLSP TSTLNMSQEE PPELTSSQTI AEEEGTTAET QTLTFTPSET  3120
PTSLLPVSSP TEPTARRKSS PETWASSISV PAKTSLVETT DGTLVTTIKM SSQAAQGNST  3180
WPAPAEETGS SPAGTSPGSP EMSTTLKIMS SKEPSISPEI RSTVRNSPWK TPETTVPMET  3240
TVEPVTLQST ALGSGSTSIS HLPTGTTSPT KSPTENMLAT ERVSLSPSPP EAWTNLYSGT  3300
PGGTRQSLAT MSSVSLESPT ARSITGTGQQ SSPELVSKTT GMEFSMWHGS TGGTTGDTHV  3360
SLSTSSNILE DPVTSPNSVS SLTDKSKHKT ETWVSTTAIP STVLNNKIMA AEQQTSRSVD  3420
EAYSSTSSWS DQTSGSDITL GASPDVTNTL YITSTAQTTS LVSLPSGDQG ITSLTNPSGG  3480
KTSSASSVTS PSIGLETLRA NVSAVKSDIA PTAGHLSQTS SPAEVSILDV TTAPTPGIST  3540
TITTMGTNSI STTTPNPEVG MSTMDSTPAT ERRTTSTEHP STWSSTAASD SWTVTDMTSN  3600
LKVARSPGTI STMHTTSFLA SSTELDSMST PHGRITVIGT SLVTPSSDAS AVKTETSTSE  3660
RTLSPSDTTA STPISTFSRV QRMSISVPDI LSTSWTPSST EAEDVPVSMV STDHASTKTD  3720
PNTPLSTFLF DSLSTLDWDT GRSLSSATAT TSAPQGATTP QELTLETMIS PATSQLPFSI  3780
GHITSAVTPA AMARSSGVTF SRPDPTSKKA EQTSTQLPTT TSAHPGQVPR SAATTLDVIP  3840
HTAKTPDATF QRQGQTALTT EARATSDSWN EKEKSTPSAP WITEMMNSVS EDTIKEVTSS  3900
SSVLRTLNTL DINLESGTTS SPSWKSSPYE RIAPSESTTD KEAIHPSTNT VETTGWVTSS  3960
EHASHSTIPA HSASSKLTSP VVTTSTREQA IVSMSTTTWP ESTRARTEPN SFLTIELRDV  4020
SPYMDTSSTT QTSIISSPGS TAITKGPRTE ITSSKRISSS FLAQSMRSSD SPSEAITRLS  4080
NFPAMTESGG MILAMQTSPP GATSLSAPTL DTSATASWTG TPLATTQRFT YSEKTTLFSK  4140
GPEDTSQPSP PSVEETSSSS SLVPIHATTS PSNILLTSQG HSPSSTPPVT SVFLSETSGL  4200
GKTTDMSRIS LEPGTSLPPN LSSTAGEALS TYEASRDTKA IHHSADTAVT NMEATSSEYS  4260
PIPGHTKPSK ATSPLVTSHI MGDITSSTSV FGSSETTEIE TVSSVNQGLQ ERSTSQVASS  4320
ATETSTVITH VSSGDATTHV TKTQATFSSG TSISSPHQFI TSTNTFTDVS TNPSTSLIMT  4380
ESSGVTITTQ TGPTGAATQG PYLLDTSTMP YLTETPLAVT PDFMQSEKTT LISKGPKDVS  4440
WTSPPSVAET SYPSSLTPFL VTTIPPATST LQGQHTSSPV SATSVLTSGL VKTTDMLNTS  4500
MEPVTNSPQN LNNPSNEILA TLAATTDIET IHPSINKAVT NMGTASSAHV LHSTLPVSSE  4560
PSTATSPMVP ASSMGDALAS ISIPGSETTD IEGEPTSSLT AGRKENSTLQ EMNSTTESNI  4620
ILSNVSVGAI TEATKMEVPS FDATFIPTPA QSTKFPDIFS VASSRLSNSP PMTISTHMTT  4680
TQTGSSGATS KIPLALDTST LETSAGTPSV VTEGFAHSKI TTAMNNDVKD VSQTNPPFQD  4740
EASSPSSQAP VLVTTLPSSV AFTPQWHSTS SPVSMSSVLT SSLVKTAGKV DTSLETVTSS  4800
PQSMSNTLDD ISVTSAATTD IETTHPSINT VVTNVGTTGS AFESHSTVSA YPEPSKVTSP  4860
NVTTSTMEDT TISRSIPKSS KTTRTETETT SSLTPKLRET SISQEITSST ETSTVPYKEL  4920
TGATTEVSRT DVTSSSSTSF PGPDQSTVSL DISTETNTRL STSPIMTESA EITITTQTGP  4980
HGATSQDTFT MDPSNTTPQA GIHSAMTHGF SQLDVTTLMS RIPQDVSWTS PPSVDKTSSP  5040
SSFLSSPAMT TPSLISSTLP EDKLSSPMTS LLTSGLVKIT DILRTRLEPV TSSLPNFSST  5100
SDKILATSKD SKDTKEIFPS INTEETNVKA NNSGHESHSP ALADSETPKA TTQMVITTTV  5160
GDPAPSTSMP VHGSSETTNI KREPTYFLTP RLRETSTSQE SSFPTDTSFL LSKVPTGTIT  5220
EVSSTGVNSS SKISTPDHDK STVPPDTFTG EIPRVFTSSI KTKSAEMTIT TQASPPESAS  5280
HSTLPLDTST TLSQGGTHST VTQGFPYSEV TTLMGMGPGN VSWMTTPPVE ETSSVSSLMS  5340
SPAMTSPSPV SSTSPQSIPS SPLPVTALPT SVLVTTTDVL GTTSPESVTS SPPNLSSITH  5400
ERPATYKDTA HTEAAMHHST NTAVTNVGTS GSGHKSQSSV LADSETSKAT PLMSTTSTLG  5460
DTSVSTSTPN ISQTNQIQTE PTASLSPRLR ESSTSEKTSS TTETNTAFSY VPTGAITQAS  5520
RTEISSSRTS ISDLDRPTIA PDISTGMITR LFTSPIMTKS AEMTVTTQTT TPGATSQGIL  5580
PWDTSTTLFQ GGTHSTVSQG FPHSEITTLR SRTPGDVSWM TTPPVEETSS GFSLMSPSMT  5640
SPSPVSSTSP ESIPSSPLPV TALLTSVLVT TTNVLGTTSP EPVTSSPPNL SSPTQERLTT  5700
YKDTAHTEAM HASMHTNTAV ANVGTSISGH ESQSSVPADS HTSKATSPMG ITFAMGDTSV  5760
STSTPAFFET RIQTESTSSL IPGLRDTRTS EEINTVTETS TVLSEVPTTT TTEVSRTEVI  5820
TSSRTTISGP DHSKMSPYIS TETITRLSTF PFVTGSTEMA ITNQTGPIGT ISQATLTLDT  5880
SSTASWEGTH SPVTQRFPHS EETTTMSRST KGVSWQSPPS VEETSSPSSP VPLPAITSHS  5940
SLYSAVSGSS PTSALPVTSL LTSGRRKTID MLDTHSELVT SSLPSASSFS GEILTSEAST  6000
NTETIHFSEN TAETNMGTTN SMHKLHSSVS IHSQPSGHTP PKVTGSMMED AIVSTSTPGS  6060
PETKNVDRDS TSPLTPELKE DSTALVMNST TESNTVFSSV SLDAATEVSR AEVTYYDPTF  6120
MPASAQSTKS PDISPEASSS HSNSPPLTIS THKTIATQTG PSGVTSLGQL TLDTSTIATS  6180
AGTPSARTQD FVDSETTSVM NNDLNDVLKT SPFSAEEANS LSSQAPLLVT TSPSPVTSTL  6240
QEHSTSSLVS VTSVPTPTLA KITDMDTNLE PVTRSPQNLR NTLATSEATT DTHTMHPSIN  6300
TAVANVGTTS SPNEFYFTVS PDSDPYKATS AVVITSTSGD SIVSTSMPRS SAMKKIESET  6360
TFSLIFRLRE TSTSQKIGSS SDTSTVFDKA FTAATTEVSR TELTSSSRTS IQGTEKPTMS  6420
PDTSTRSVTM LSTFAGLTKS EERTIATQTG PHRATSQGTL TWDTSITTSQ AGTHSAMTHG  6480
FSQLDLSTLT SRVPEYISGT SPPSVEKTSS SSSLLSLPAI TSPSPVPTTL PESRPSSPVH  6540
LTSLPTSGLV KTTDMLASVA SLPPNLGSTS HKIPTTSEDI KDTEKMYPST NIAVTNVGTT  6600
```

-continued

```
TSEKESYSSV PAYSEPPKVT SPMVTSFNIR DTIVSTSMPG SSEITRIEME STFSLAHGLK  6660
GTSTSQDPIV STEKSAVLHK LTTGATETSR TEVASSRRTS IPGPDHSTES PDISTEVIPS  6720
LPISLGITES SNMTIITRTG PPLGSTSQGT FTLDTPTTSS RAGTHSMATQ EFPHSEMTTV  6780
MNKDPEILSW TIPPSIEKTS FSSSLMPSPA MTSPPVSSTL PKTIHTTPSP MTSLLTPSLV  6840
MTTDTLGTSP EPTTSSPPNL SSTSHEILTT DEDTTAIEAM HPSTSTAATN VETTSSGHGS  6900
QSSVLADSEK TKATAPMDTT STMGHTTVST SMSVSSETTK IKRESTYSLT PGLRETSISQ  6960
NASFSTDTSI VLSEVPTGTT AEVSRTEVTS SGRTSIPGPS QSTVLPEIST RTMTRLFASP  7020
TMTESAEMTI PTQTGPSGST SQDTLTLDTS TTKSQAKTHS TLTQRFPHSE MTTLMSRGPG  7080
DMSWQSSPSL ENPSSLPSLL SLPATTSPPP ISSTLPVTIS SSPLPVTSLL TSSPVTTTDM  7140
LHTSPELVTS SPPKLSHTSD ERLTTGKDTT NTEAVHPSTN TAASNVEIPS SGHESPSSAL  7200
ADSETSKATS PMFITSTQED TTVAISTPHF LETSRIQKES ISSLSPKLRE TGSSVETSSA  7260
IETSAVLSEV SIGATTEISR TEVTSSSRTS ISGSAESTML PEISTTRKII KFPTSPILAE  7320
SSEMTIKTQT SPPGSTSEST FTLDTSTTPS LVITHSTMTQ RLPHSEITTL VSRGAGDVPR  7380
PSSLPVEETS PPSSQLSLSA MISPSPVSST LPASSHSSSA SVTSLLTPGQ VKTTEVLDAS  7440
AEPETSSPPS LSSTSVEILA TSEVTTDTEK IHPFSNTAVT KVGTSSSGHE SPSSVLPDSE  7500
TTKATSAMGT ISIMGDTSVS TLTPALSNTR KIQSEPASSL TTRLRETSTS EETSLATEAN  7560
TVLSKVSTGA TTEVSRTEAI SFSRTSMSGP EQSTMSQDIS IGTIPRISAS SVLTESAKMT  7620
ITTQTGPSES TLESTLNLNT ATTPSWVETH SIVIQGFPHP EMTTSMGRGP GGVSWPSPPF  7680
VKETSPPSSP LSLPAVTSPH PVSTTFLAHI PPSPLPVTSL LTSGPATTTD ILGTSTEPGT  7740
SSSSSLSTTS HERLTTYKDT AHTEAVHPST NTGGTNVATT SSGYKSQSSV LADSSPMCTT  7800
STMGDTSVLT STPAFLETRR IQTELASSLT PGLRESSGSE GTSSGTKMST VLSKVPTGAT  7860
TEISKEDVTS IPGPAQSTIS PDISTRTVSW FSTSPVMTES AEITMNTHTS PLGATTQGTS  7920
TLDTSSTTSL TMTHSTISQG FSHSQMSTLM RRGPEDVSWM SPPLLEKTRP SFSLMSSPAT  7980
TSPSPVSSTL PESISSSPLP VTSLLTSGLA KTTDMLHKSS EPVTNSPANL SSTSSVEILAT  8040
SEVTTDTEKT HPSSNRTVTD VGTSSSGHES TSFVLADSQT SKVTSPMVIT STMEDTSVST  8100
STPGFFETSR IQTEPTSSLT LGLRKTSSSE GTSLATEMST VLSGVPTGAT AEVSRTEVTS  8160
SSRTSISGFA QLTVSPETST ETITRLPTSS IMTESAEMMI KTQTDPPGST PESTHTVDIS  8220
TTPNWVETHS TVTQRFSHSE MTTLVSRSPG DMLWPSQSSV EETSSASSLL SLPATTSPSP  8280
VSSTLVEDFP SASLPVTSLL NPGLVITTDR MGISREPGTS STSNLSSTSH ERLTTLEDTV  8340
DTEDMQPSTH TAVTNVRTSI SGHESQSSVL SDSETPKATS PMGTTYTMGE TSVSISTSDF  8400
FETSRIQIEP TSSLTSGLRE TSSSERISSA TEGSTVLSEV PSGATTEVSR TEVISSRGTS  8460
MSGPDQFTIS PDISTEAITR LSTSPIMTES AESAITIETG SPGATSEGTL TLDTSTTTFW  8520
SGTHSTASPG FSHSEMTTLM SRTPGDVPWP SLPSVEEASS VSSSLSSPAM TSTSFFSTLP  8580
ESISSSPHPV TALLTLGPVK TTDMLRTSSE PETSSPPNLS STSAEILATS EVTKDREKIH  8640
PSSNTPVVNV GTVIYKHLSP SSVLADLVTT KPTSPMATTS TLGNTSVSTS TPAFPETMMT  8700
QPTSSLTSGL REISTSQETS SATERSASLS GMPTGATTKV SRTEALSLGR TSTPGPAQST  8760
ISPEISTETI TRISTPLTTT GSAEMTITPK TGHSGASSQG TFTLDTSSRA SWPGTHSAAT  8820
HRSPHSGMTT PMSRGPEDVS WPSRPSVEKT SPPSSLVSLS AVTSPSPLYS TPSESSHSSP  8880
LRVTSLFTPV MMKTTDMLDT SLEPVTTSPP SMNITSDESL ATSKATMETE AIQLSENTAV  8940
TQMGTISARQ EFYSSYPGLP EPSKVTSPVV TSSTIKDIVS TTIPASSEIT RIEMESTSTL  9000
TPTPRETSTS QEIHSATKPS TVPYKALTSA TIEDSMTQVM SSSRGPSPDQ STMSQDISTE  9060
VITRLSTSPI KTESTEMTIT TQTGSPGATS RGTLTLDTST TFMSGTHSTA SQGFSHSQMT  9120
ALMSRTPGDV PWLSHPSVEE ASSASFSLSS PVMTSSSPVS STLPDSIHSS SLPVTSLLTS  9180
GLVKTTELLG TSSEPETSSP PNLSSTSAEI LAITEVTTDT EKLEMTNVVT SGYTHESPSS  9240
VLADSVTTKA TSSMGITYPT GDTNVLTSTP AFSDTSRIQT KSKLSLTPGL METSISEETS  9300
SATEKSTVLS SVPTGATTEV SRTEAISSSR TSIPGPAQST MSSDTSMETI TRISTPLTRK  9360
ESTDMAITPK TGPSGATSQG TFTLDSSSTA SWPGTHSATT QRFPQSVVTT PMSRGPEDVS  9420
WPSPLSVEKN SPPSSLVSSS SVTSPSPLYS TPSGSSHSSP VPVTSLFTSI MMKATDMLDA  9480
SLEPETTSAP NMNITSDESL AASKATTETE AIHVFENTAA SHVETTSATE ELYSSSPGFS  9540
EPTKVISPVV TSSSIRDNMV STTMPGSSGI TRIEIESMSS LTPGLRETRT SQDITSSTET  9600
STVLYKMPSG ATPEVSRTEV MPSSRTSIPG PAQSTMSLDI SDEVVTRLST SPIMTESAEI  9660
TITTQTGYSL ATSQVTLPLG TSMTFLSGTH STMSQGLSHS EMTNLMSRGP ESLSWTSPRF  9720
VETTRSSSSL TSLPLTTSLS PVSSTLLDSS PSSPLPVTSL ILPGLVKTTE VLDTSSEPKT  9780
SSSPNLSSTS VEIPATSEIM TDTEKIHPSS NTAVAKVRTS SSVHESHSSV LADSETTITI  9840
PSMGITSAVD DTTVFTSNPA FSETRRIPTE PTFSLTPGFR ETSTSEETTS ITETSAVLYG  9900
VPTSATTEVS MTEIMSSNRI HIPDSDQSTM SPDIITEVIT RLSSSSMMSE STQMTITTQK  9960
SSPGATAQST LTLATTTAPL ARTHSTVPPR FLHSEMTTLM SRSPENPSWK SSLFVEKTSS  10020
SSSLLSLPVT TSPSVSSTLP QSIPSSSFSV TSLLTPGMVK TTDTSTEPGT SLSPNLSGTS  10080
VEILAASEVT TDTEKIHPSS SMAVTNVGTT SSGHELYSSV SIHSEPSKAT YPVGTPSSMA  10140
ETSISTSMPA NFETTGFEAE PFSHLTSGFR KTNMSLDTSS VTPTNTPSSP GSTHLLQSSK  10200
TDFTSSAKTS SPDWPPASQY TEIPVDIITP FNASPSITES TGITSFPESR FTMSVTESTH  10260
HLSTDLLPSA ETISTGTVMP SLSEAMTSFA TTGVPRAISG SGSPFSRTES GPGDATLSTI  10320
AESLPSSTPV PFSSSTFTTT DSSTIPALHE ITSSSATPYR VDTSLGTESS TTEGRLVMVS  10380
TLDTSSQPGR TSSSPILDTR MTESVELGTV TSAYQVPSLS TRLTRTDGIM EHITKIPNEA  10440
AHRGTIRPVK GPQTSTSPAS PKGLHTGGTK RMETTTTALK TTTTALKTTS RATLTTSVYT  10500
PTLGTLTPLN ASMQMASTIP TEMMITTPYV FPDVPETTSS LATSLGAETS TALPRTTPSV  10560
FNRESETTAS LVSRSGAERS PVIQTLDVSS SEPDTTASWV IHPAETIPTV SKTTPNFFHS  10620
ELDTVSSTAT SHGADVSSAI PTNISPSELD ALTPLVTISG TDTSTTFPTL TKSPHETETR  10680
TTWLTHPAET SSTIPRTIPN FSHHESDATP SIATSPGAET SSAIPIMTVS PGAEDLVTSQ  10740
VTSSGTDRNM TIPTLTLSPG EPKTIASLVT HPEAQTSSAI PTSTISPAVS RLVTSMVTSL  10800
AAKTSTTNRA LTNSPGEPAT TVSLVTHPAQ TSPTVPWTTS IFFHSKSDTT PSMTTSHGAE  10860
SSSAVPTPTV STEVPGVVTP LVTSSRAVIS TTIPILTLSP GEPETTPSMA TSHGEEASSA  10920
IPTPTVSPGV PGVVTSLVTS SRAVTSTTIP ILTFSLGEPE TTPSMATSHG TEAGSAVPTV  10980
LPEVPGMVTS LVASSRAVTS TTLPTLTLSP GEPETTPSMA TSHGAEASST VPTVSPEVPG  11040
VVTSLVTSSS GVNSTSIPTL ILSPGELETT PSMATSHGAE ASSAVPTPTV SPGVSGVVTP  11100
LVTSSRAVTS TTIPILTLSS SEPETTPSMA TSHGVEASSA VLTVSPEVPG MVTSLVTSSR  11160
AVTSTTIPTL TISSDEPETT TSLVTHSEAK MISAIPTLAV SPTVQGLVTS LVTSSGSETS  11220
AFSNLTVASS QPETIDSWVA HPGTEASSVV PTLTVSTGEP FTNISLVTHP AESSSTLPRT  11280
TSRFSHSELD TMPSTVTSPE AESSSAISTT ISPGIPGVLT SLVTSSGRDI SATFPTVPES  11340
```

-continued

```
PHESEATASW VTHPAVTSTT VPRTTPNYSH SEPDTTPSIA TSPGAEATSD FPTITVSPDV  11400
PDMVTSQVTS SGTDTSITIP TLTLSSGEPE TTTSFITYSE THTSSAIPTL PVSPGASKML  11460
TSLVISSGTD STTTFPTLTE TPYEPETTAI QLIHPAETNT MVPRTTPKFS HSKSDTTLPV  11520
AITSPGPEAS SAVSTTTISP DMSDLVTSLV PSSGTDTSTT FPTLSETPYE PETTATWLTH  11580
PAETSTTVSG TIPNFSHRGS DTAPSMVTSP GVDTRSGVPT TTIPPSIPGV VTSQVTSSAT  11640
DTSTAIPTLT PSPGEPETTA SSATHPGTQT GFTVPIRTVP SSEPDTMASW VTHPPQTSTP  11700
VSRTTSSFSH SSPDATPVMA TSPRTEASSA VLTTISPGAP EMVTSQITSS GAATSTTVPT  11760
LTHSPGMPET TALLSTHPRT ETSKTFPAST VFPQVSETTA SLTIRPGAET STALPTQTTS  11820
SLFTLLVTGT SRVDLSPTAS PGVSAKTAPL STHPGTETST MIPTSTLSLG LLETTGLLAT  11880
SSSAETSTST LTLTVSPAVS GLSSASITTD KPQTVTSWNT ETSPSVTSVG PPEFSRTVTG  11940
TTMTLIPSEM PTPPKTSHGE GVSPTTILRT TMVEATNLAT TGSSPTVAKT TTTFNTLAGS  12000
LFTPLTTPGM STLASESVTS RTSYNHRSWI STTSSYNRRY WTPATSTPVT STFSPGISTS  12060
SIPSSTAATV PFMVPFTLNF TITNLQYEED MRHPGSRKFN ATERELQGLL KPLFRNSSLE  12120
YLYSGCRLAS LRPEKDSSAT AVDAICTHRP DPEDLGLDRE RLYWELSNLT NGIQELGPYT  12180
LDRNSLYVNG FTHRSSMPTT STPGTSTVDV GTSGTPSSSP SPTTAGPLLM PFTLNFTITN  12240
LQYEEDMRRT GSRKFNTMES VLQGLLKPLF KNTSVGPLYS GCRLTLLRPE KDGAATGVDA  12300
ICTHRLDPKS PGLNREQLYW ELSKLTNDIE ELGPYTLDRN SLYVNGFTHQ SSVSTTSTPG  12360
TSTVDLRTSG TPSSLSSPTI MAAGPLLVPF TLNFTITNLQ YGEDMGHPGS RKFNTTERVL  12420
QGLLGPIFKN TSVGPLYSGC RLTSLRSEKD GAATGVDAIC IHHLDPKSPG LNRERLYWEL  12480
SQLTNGIKEL GPYTLDRNSL YVNGFTHRTS VPTSSTPGTS TVDLGTSGTP FSLPSPATAG  12540
PLLVLFTLNF TITNLKYEED MHRPGSRKFN TTERVLQTLL GPMFKNTSVG LLYSGCRLTL  12600
LRSEKDGAAT GVDAICTHRL DPKSPGVDRE QLYWELSQLT NGIKELGPYT LDRNSLYVNG  12660
FTHWIPVPTS STPGTSTVDL GSGTPSSLPS PTTAGPLLVP FTLNFTITNL KYEEDMHCPG  12720
SRKFNTTERV LQSLLGPMFK NTSVGPLYSG CRLTLLRSEK DGAATGVDAI CTHRLDPKSP  12780
GVDREQLYWE LSQLTNGIKE LGPYTLDRNS LYVNGFTHQT SAPNTSTPGT STVDLGTSGT  12840
PSSLPSPTSA GPLLVPFTLN FTITNLQYEE DMHHPGSRKF NTTERVLQGL LGPMFKNTSV  12900
GLLYSGCRLT LLRPEKNGAA TGMDAICSHR LDPKSPGLNR EQLYWELSQL THGIKELGPY  12960
TLDRNSLYVN GFTHRSSVAP TSTPGTSTVD LGTSGTPSSL PSPTTAVPLL VPFTLNFTIT  13020
NLQYGEDMRH PGSRKFNTTE RVLQGLLGPL FKNSSVGPLY SGCRLISLRS EKDGAATGVD  13080
AICTHHLNPQ SPGLDREQLY WQLSQMTNGI KELGPYTLDR NSLYVNGFTH RSSGLTTSTP  13140
WTSTVDLGTS GTPSPVPSPT TTGPLLVPFT LNFTITNLQY EENMGHPGSR KFNITESVLQ  13200
GLLKPLFKST SVGPLYSGCR LTLLRPEKDG VATRVDAICT HRPDPKIPGL DRQQLYWELS  13260
QLTHSITELG PYTLDRDSLY VNGFTQRSSV PTTSTPGTFT VQPETSETPS SLPGPTATGP  13320
VLLPFTLNFT ITNLQYEEDM RRPGSRKFNT TERVLQGLLM PLFKNTSVSS LYSGCRLTLL  13380
RPEKDGAATR VDAVCTHRPD PKSPGLDRER LYWKLSQLTH GITELGPYTL DRHSLYVNGF  13440
THQSSMTTTR TPDTSTMHLA TSRTPASLSG PMTASPLLVL FTINFTITNL RYEENMHHPG  13500
SRKFNTTERV LQGLLRPVFK NTSVGPLYSG CRLTLLRPKK DGAATKVDAI CTYRPDPKSP  13560
GLDREQLYWE LSQLTHSITE LGPYTLDRDS LYVNGFTQRS SVPTTSIPGT PTVDLGTSGT  13620
PVSKPGPSAA SPLLVLFTLN FTITNLRYEE NMQHPGSRKF NTTERVLQGL LRSLFKSTSV  13680
GPLYSGCRLT LLRPEKDGTA TGVDAICTHH PDPKSPRLDR EQLYWELSQL THNITELGPY  13740
ALDNDSLFVN GFTHRSSVST TSTPGTPTVY LGASKTPASI FGPSAASHLL ILFTLNFTIT  13800
NLRYEENMWP GSRKFNTTER VLQGLLRPLF KNTSVGPLYS GCRLTLLRPE KDGEATGVDA  13860
ICTHRPDPTG PGLDREQLYL ELSQLTHSIT ELGPYTLDRD SLYVNGFTHR SSVPTTSTGV  13920
VSEEPFTLNF TINNLRYMAD MGQPGSLKFN ITDNVMQHLL SPLFQRSSLG ARYTGCRVIA  13980
LRSVKNGAET RVDLLCTYLQ PLSGPGLPIK QVFHELSQQT HGITRLGPYS LDKDSLYLNG  14040
YNEPGPDEPP TTPKPATTFL PPLSEATTAM GYHLKTLTLN FTISNLQYSP DMGKGSATFN  14100
STEGVLQHLL RPLFQKSSMG PFYLGCQLIS LRPEKDGAAT GVDTTCTYHP DPVGPGLDIQ  14160
QLYWELSQLT HGVTQLGFYV LDRDSLFING YAPQNLSIRG EYQINFHIVN WNLSNPDPTS  14220
SEYITLLRDI QDKVTTLYKG SQLHDTFRFC LVTNLTMDSV LVTVKALFSS NLDPSLVEQV  14280
FLDKTLNASF HWLGSTYQLV DIHVTEMESS VYQPTSSSST QHFYLNFTIT NLPYSQDKAQ  14340
PGTTNYQRNK RNIEDALNQL FRNSSIKSYF SDCQVSTFRS VPNRHHTGVD SLCNFSPLAR  14400
RVDRVAIYEE FLRMTRNGTQ LQNFTLDRSS VLVDGYSPNR NEPLTGNSDL PFWAVILIGL  14460
AGLLGVITCL ICGVLVTTRR RKKEGEYNVQ QQCPGYYQSH LDLEDLQ                14507
```

```
SEQ ID NO: 9          moltype = AA  length = 490
FEATURE               Location/Qualifiers
REGION                1..490
                      note = human STEAP2 (STAMP1) Protein
source                1..490
                      mol_type = protein
                      organism = Homo sapiens
SEQUENCE: 9
MESISMMGSP KSLSETFLPN GINGIKDARK VTVGVIGSGD FAKSLTIRLI RCGYHVVIGS  60
RNPKFASEFF PHVVDVTHHE DALTKTNIIF VAIHREHYTS LWDLRHLLVG KILIDVSNNM  120
RINQYPESNA EYLASLFPDS LIVKGFNVVS AWALQLGPKD ASRQVYICSN NIQARQQVIE  180
LARQLNFIPI DLGSLSSARE IENLPLRLFT LWRGPVVVAI SLATFFFLYS FVRDVIHPYA  240
RNQQSDFYKI PIEIVNKTLP IVAITLLSLV YLAGLLAAAY QLYYGTKYRR FPPWLETWLQ  300
CRKQLGLLSF FFAMVHVAYS LCLPMRRSER YLFLNMAYQQ VHANIENSWN EEEVWRIEMY  360
ISFGIMSLGL LSLLAVTSIP SVSNALNWRE FSFIQSTLGY VALLISTFHV LIYGWKRAFE  420
EEYYRFYTPP NFVLALVLPS IVILGKIILF LPCISRKLKR IKKGWEKSQF LEEGMGGTIP  480
HVSPERVTVM                                                        490
```

```
SEQ ID NO: 10         moltype = AA  length = 453
FEATURE               Location/Qualifiers
REGION                1..453
                      note = Anti-CD20 REGN1979 Heavy Chain
source                1..453
                      mol_type = protein
                      organism = synthetic construct
```

```
SEQUENCE: 10
EVQLVESGGG LVQPGRSLRL SCVASGFTFN DYAMHWVRQA PGKGLEWVSV ISWNSDSIGY  60
ADSVKGRFTI SRDNAKNSLY LQMHSLRAED TALYYCAKDN HYGSGSYYYY QYGMDVWGQG  120
TTVTVSSAST KGPSVFPLAP CSRSTSESTA ALGCLVKDYF PEPVTVSWNS GALTSGVHTF  180
PAVLQSSGLY SLSSVVTVPS SSLGTKTYTC NVDHKPSNTK VDKRVESKYG PPCPPCPAPP  240
VAGPSVFLFP PKPKDTLMIS RTPEVTCVVV DVSQEDPEVQ FNWYVDGVEV HNAKTKPREE  300
QFNSTYRVVS VLTVLHQDWL NGKEYKCKVS NKGLPSSIEK TISKAKGQPR EPQVYTLPPS  360
QEEMTKNQVS LTCLVKGFYP SDIAVEWESN GQPENNYKTT PPVLDSDGSF FLYSRLTVDK  420
SRWQEGNVFS CSVMHEALHN HYTQKSLSLS LGK                              453

SEQ ID NO: 11          moltype = AA  length = 449
FEATURE                Location/Qualifiers
REGION                 1..449
                       note = Anti-CD3 REGN1979 Heavy Chain
source                 1..449
                       mol_type = protein
                       organism = synthetic construct
SEQUENCE: 11
EVQLVESGGG LVQPGRSLRL SCAASGFTFD DYTMHWVRQA PGKGLEWVSG ISWNSGSIGY  60
ADSVKGRFTI SRDNAKKSLY LQMNSLRAED TALYYCAKDN SGYGHYYYGM DVWGQGTTVT  120
VASASTKGPS VFPLAPCSRS TSESTAALGC LVKDYFPEPV TVSWNSGALT SGVHTFPAVL  180
QSSGLYSLSS VVTVPSSSLG TKTYTCNVDH KPSNTKVDKR VESKYGPPCP PCPAPPVAGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNRFTQ KSLSLSLGK                                   449

SEQ ID NO: 12          moltype = AA  length = 214
FEATURE                Location/Qualifiers
REGION                 1..214
                       note = Common REGN1979 Light Chain
source                 1..214
                       mol_type = protein
                       organism = synthetic construct
SEQUENCE: 12
EIVMTQSPAT LSVSPGERAT LSCRASQSVS SNLAWYQQKP GQAPRLLIYG ASTRATGIPA  60
RFSGSGSGTE FTLTISSLQS EDFAVYYCQH YINWPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 13          moltype = AA  length = 127
FEATURE                Location/Qualifiers
REGION                 1..127
                       note = Anti-CD20 REGN1979 HCVR
source                 1..127
                       mol_type = protein
                       organism = synthetic construct
SEQUENCE: 13
EVQLVESGGG LVQPGRSLRL SCVASGFTFN DYAMHWVRQA PGKGLEWVSV ISWNSDSIGY  60
ADSVKGRFTI SRDNAKNSLY LQMHSLRAED TALYYCAKDN HYGSGSYYYY QYGMDVWGQG  120
TTVTVSS                                                           127

SEQ ID NO: 14          moltype = AA  length = 123
FEATURE                Location/Qualifiers
REGION                 1..123
                       note = Anti-CD3 REGN1979 HCVR
source                 1..123
                       mol_type = protein
                       organism = synthetic construct
SEQUENCE: 14
EVQLVESGGG LVQPGRSLRL SCAASGFTFD DYTMHWVRQA PGKGLEWVSG ISWNSGSIGY  60
ADSVKGRFTI SRDNAKKSLY LQMNSLRAED TALYYCAKDN SGYGHYYYGM DVWGQGTTVT  120
VAS                                                               123

SEQ ID NO: 15          moltype = AA  length = 108
FEATURE                Location/Qualifiers
REGION                 1..108
                       note = Common REGN1979 LCVR
source                 1..108
                       mol_type = protein
                       organism = synthetic construct
SEQUENCE: 15
EIVMTQSPAT LSVSPGERAT LSCRASQSVS SNLAWYQQKP GQAPRLLIYG ASTRATGIPA  60
RFSGSGSGTE FTLTISSLQS EDFAVYYCQH YINWPLTFGG GTKVEIKR               108

SEQ ID NO: 16          moltype = AA  length = 8
FEATURE                Location/Qualifiers
REGION                 1..8
                       note = Anti-CD20 REGN1979 HCDR1
```

-continued

```
source                  1..8
                        mol_type = protein
                        organism = synthetic construct
SEQUENCE: 16
GFTFNDYA                                                                    8

SEQ ID NO: 17           moltype = AA  length = 8
FEATURE                 Location/Qualifiers
REGION                  1..8
                        note = Anti-CD20 REGN1979 HCDR2
source                  1..8
                        mol_type = protein
                        organism = synthetic construct
SEQUENCE: 17
ISWNSDSI                                                                    8

SEQ ID NO: 18           moltype = AA  length = 20
FEATURE                 Location/Qualifiers
REGION                  1..20
                        note = Anti-CD20 REGN1979 HCDR3
source                  1..20
                        mol_type = protein
                        organism = synthetic construct
SEQUENCE: 18
AKDNHYGSGS YYYYQYGMDV                                                       20

SEQ ID NO: 19           moltype = AA  length = 8
FEATURE                 Location/Qualifiers
REGION                  1..8
                        note = Anti-CD3 REGN1979 HCDR1
source                  1..8
                        mol_type = protein
                        organism = synthetic construct
SEQUENCE: 19
GFTFDDYT                                                                    8

SEQ ID NO: 20           moltype = AA  length = 8
FEATURE                 Location/Qualifiers
REGION                  1..8
                        note = Anti-CD3 REGN1979 HCDR2
source                  1..8
                        mol_type = protein
                        organism = synthetic construct
SEQUENCE: 20
ISWNSGSI                                                                    8

SEQ ID NO: 21           moltype = AA  length = 16
FEATURE                 Location/Qualifiers
REGION                  1..16
                        note = Anti-CD3 REGN1979 HCDR3
source                  1..16
                        mol_type = protein
                        organism = synthetic construct
SEQUENCE: 21
AKDNSGYGHY YYGMDV                                                           16

SEQ ID NO: 22           moltype = AA  length = 6
FEATURE                 Location/Qualifiers
REGION                  1..6
                        note = Common REGN1979 LCDR1
source                  1..6
                        mol_type = protein
                        organism = synthetic construct
SEQUENCE: 22
QSVSSN                                                                      6

SEQ ID NO: 23           moltype =   length =
SEQUENCE: 23
000
```

-continued

```
SEQ ID NO: 24         moltype = AA  length = 9
FEATURE               Location/Qualifiers
REGION                1..9
                      note = Common REGN1979 LCDR3
source                1..9
                      mol_type = protein
                      organism = synthetic construct
SEQUENCE: 24
QHYINWPLT                                                     9
```

What is claimed is:

1. A method of administering a therapeutic protein to a subject in a dosing regimen to mitigate adverse effects of cytokine release syndrome (CRS) or infusion-related reaction (IRR) in the treatment of a CD20-expressing B-cell malignancy, comprising:

administering fractions of a primary dose (D1) of the therapeutic protein in week 1 of the dosing regimen, wherein the primary dose comprises no more than 10 mg of the therapeutic protein, a first dose fraction (F1D1) comprises 10% to 90% of the total primary dose and is administered to the subject on day 1 of week 1, and a second dose fraction (F2D1) comprises the remaining 10% to 90% of the total primary dose and is administered to the subject from 12 to 96 hours following administration of the F1D1;

administering fractions of a secondary dose (D2) of the therapeutic protein in week 2 of the dosing regimen, wherein the secondary dose is greater than the primary dose and no more than one-half of a maximum weekly dose of the therapeutic protein, a first dose fraction (F1D2) comprises 10% to 90% of the total secondary dose, a second dose fraction (F2D2) comprises the remaining 10% to 90% of the total secondary dose, and the F2D2 is administered to the subject from 12 to 96 hours following administration of the F1D2 during week 2 of the dosing regimen; and administering the maximum weekly dose of the therapeutic protein to the subject as a single dose in a subsequent week of the dosing regimen, wherein the administration of the therapeutic protein to the subject in the dosing regimen reduces the prevalence or severity, or both the prevalence and severity, of CRR or IRR compared to a dosing regimen not including split administration of the primary dose and the secondary dose, and wherein the therapeutic protein is a bispecific antibody or antigen-binding fragment thereof comprising a first antigen-binding arm that binds human CD3 and comprises complementarity determining regions HCDR1-HCDR2-HCDR3-LCDR1-LCDR2-LCDR3 comprising the amino acid sequences, respectively, of SEQ ID NOs: 19-20-21-22-23-24, and a second antigen-binding arm that binds human CD20 and comprises complementarity determining regions HCDR1-HCDR2-HCDR3-LCDR1-LCDR2-LCDR3 comprising the amino acid sequences, respectively, of SEQ ID NOs: 16-17-18-22-23-24.

2. The method of claim 1, further comprising:

administering fractions of a tertiary dose (D3) of the therapeutic protein in week 3 of the dosing regimen, wherein the tertiary dose is no less than one-half of the maximum weekly dose of the therapeutic protein and no more than the maximum weekly dose of the therapeutic protein, a first dose fraction (F1D3) comprises 10% to 90% of the total tertiary dose, a second dose fraction (F2D3) comprises the remaining 10% to 90% of the total tertiary dose, and the F2D3 is administered to the subject from 12 to 96 hours following administration of the F1D3 during week 3 of the dosing regimen; and administering the maximum weekly dose of the therapeutic protein to the subject as a single dose in the subsequent week of the dosing regimen.

3. The method of claim 1, wherein:

(a) the first dose fraction (F1D1) comprises 15% to 85% of the total primary dose and the second dose fraction (F2D1) comprises the remaining 15% to 85% of the total primary dose;

(b) the first dose fraction (F1D1) comprises 20% to 80% of the total primary dose and the second dose fraction (F2D1) comprises the remaining 20% to 80% of the total primary dose;

(c) the first dose fraction (F1D1) comprises 25% to 75% of the total primary dose and the second dose fraction (F2D1) comprises the remaining 25% to 75% of the total primary dose:

(d) the first dose fraction (F1D1) comprises 30% to 70% of the total primary dose and the second dose fraction (F2D1) comprises the remaining 30% to 70% of the total primary dose; or (e) the first dose fraction (F1D1) comprises 35% to 65% of the total primary dose and the second dose fraction (F2D1) comprises the remaining 35% to 65% of the total primary dose.

4. The method of claim 1, wherein:

(a) the first dose fraction (F1D2) comprises 15% to 85% of the total secondary dose and the second dose fraction (F2D2) comprises the remaining 15% to 85% of the total secondary dose;

(b) the first dose fraction (F1D2) comprises 20% to 80% of the total secondary dose and the second dose fraction (F2D2) comprises the remaining 20% to 80% of the total secondary dose;

(c) the first dose fraction (F1D2) comprises 25% to 75% of the total secondary dose and the second dose fraction (F2D2) comprises the remaining 25% to 75% of the total secondary dose;

(d) the first dose fraction (F1D2) comprises 30% to 70% of the total secondary dose and the second dose fraction (F2D2) comprises the remaining 30% to 70% of the total secondary dose; or (e) the first dose fraction (F1D2) comprises 35% to 65% of the total secondary dose and the second dose fraction (F2D2) comprises the remaining 35% to 65% of the total secondary dose.

5. The method of claim 2, wherein:
(a) the first dose fraction (F1D3) comprises 15% to 85% of the total tertiary dose and the second dose fraction (F2D3) comprises the remaining 15% to 85% of the total tertiary dose;
(b) the first dose fraction (F1D3) comprises 20% to 80% of the total tertiary dose and the second dose fraction (F2D3) comprises the remaining 20% to 80% of the total tertiary dose;
(c) the first dose fraction (F1D3) comprises 25% to 75% of the total tertiary dose and the second dose fraction (F2D3) comprises the remaining 25% to 75% of the total tertiary dose;
(d) the first dose fraction (F1D3) comprises 30% to 70% of the total tertiary dose and the second dose fraction (F2D3) comprises the remaining 30% to 70% of the total tertiary dose; or
(e) the first dose fraction (F1D3) comprises 35% to 65% of the total tertiary dose and the second dose fraction (F2D3) comprises the remaining 35% to 65% of the total tertiary dose.

6. The method of claim 1, wherein the F2D1 is administered to the subject from 24 to 96 hours following administration of the F1D1, or F2D1 is administered to the subject from 18 to 72 hours following administration of F1D1.

7. The method of claim 1, wherein the F2D2 is administered to the subject from 24 to 96 hours following administration of the F1D2, or F2D2 is administered to the subject from 18 to 72 hours following administration of F1D2.

8. The method of claim 1, wherein the subsequent week is week 3 of the dosing regimen, the subsequent week is week 4 of the dosing regimen, or the subsequent week is week 14 of the dosing regimen.

9. The method of claim 1, wherein the subsequent week is any one of weeks 4 to 36 of the dosing regimen.

10. The method of claim 1, wherein the primary dose (D1) is 1 mg.

11. The method of claim 1, wherein the primary dose (D1) is from 0.5 mg to 1 mg.

12. The method of claim 1, wherein the secondary dose (D2) is 20 mg.

13. The method of claim 1, wherein the maximum weekly dose of the therapeutic protein is from 5 mg to 320 mg.

14. The method of claim 1, wherein the maximum weekly dose is 40 mg, 80 mg, 160 mg, or 320 mg.

15. The method of claim 1, wherein the maximum weekly dose of the therapeutic protein is administered to the subject as a single dose during a weekly phase of the dosing regimen.

16. The method of claim 1, further comprising administering the maximum weekly dose of the therapeutic protein to the subject as a single dose once every two weeks, one every three weeks, or one every four weeks during a maintenance phase of the dosing regimen, which follows completion of a weekly phase of the dosing regimen, wherein the maximum weekly dose is from 80 mg to 320 mg.

17. The method of claim 1, wherein the therapeutic protein is maintained at a serum concentration at or above about 2000 mcg/L, at or above about 2600 mcg/L, or at least about 3700 mcg/L following administration of the maximum weekly dose for the duration of the dosing regimen.

18. The method of claim 1, wherein:
(a) the therapeutic protein is administered to the subject in combination with a second agent selected from a steroid, an anti-histamine, acetaminophen, a non-steroidal anti-inflammatory drug (NSAID), an IL-6 antagonist, or an IL-6R antagonist;
(b) the therapeutic protein is administered to the subject in combination with dexamethasone or indomethacin;
(c) the therapeutic protein is administered to the subject in combination with dexamethasone, and the dexamethasone is administered to the subject about one to three hours prior to at least one of the F1D1, the F2D1, the F1D2, and the F2D2; or
(d) the therapeutic protein is administered to the subject in combination with an anti-IL-6 antibody, an anti-IL-6R antibody, or sarilumab.

19. The method of claim 18, wherein administration of the second agent is eliminated following a first administration of the maximum weekly dose for the duration of the dosing regimen.

20. The method of claim 1, wherein the therapeutic protein is administered to the subject in combination with a second therapeutic agent, wherein the second therapeutic agent comprises at least one of rituximab, obinutuzumab, cyclophophamide, doxorubicin, vincristine, prednisone, prednisolone, bendamustine, lenalidomide, chlorambucil, ibritumomab tiuxetan, idelalisib, copanlisib, duvelisib, etoposide, methylprednisolone, cytarabine, cisplatin, mesna, ifosfamide, mitoxantrone, and procarbazine.

21. The method of claim 1, wherein the CD20-expressing B-cell malignancy is non-Hodgkin lymphoma, Hodgkin lymphoma, chronic lymphocytic leukemia, acute lymphoblastic leukemia, small lymphocytic lymphoma, diffuse large B-cell lymphoma, follicular lymphoma, mantle cell lymphoma, marginal zone lymphoma, Burkitt lymphoma, primary mediastinal B-cell lymphoma, lymphoblastic lymphoma, or Waldenstrom macroglobulinemia.

22. The method of claim 1, wherein the subject:
(a) has been diagnosed with follicular lymphoma (FL);
(b) has been diagnosed with FL that is grade 1-3a;
(c) has been diagnosed with diffuse large B-cell lymphoma (DLBCL);
(d) has been diagnosed with DLBCL, and has failed prior CAR-T therapy;
(e) has been diagnosed with mantle cell lymphoma (MCL);
(f) has been diagnosed with mantle cell lymphoma (MCL), and has failed prior Bruton tyrosine kinase (BTK) inhibitor therapy; or
(g) has been diagnosed with marginal zone lymphoma (MZL).

23. The method of claim 1, wherein the subject:
(a) has been treated previously with an anti-cancer therapy;
(b) is refractory to previous treatment or has relapsed after previous treatment;
(c) has previously been treated with an anti-CD20 antibody therapy; or
(d) has previously been treated with ritiximab.

24. The method of claim 1, wherein the incidence of grade 3 CRS and IRR is less than 10%.

25. The method of claim 24, wherein the incidence of grade 3 CRS and IRR is less than 7.5% or less than 7%.

26. The method of claim 1, wherein the first antigen-binding arm that binds human CD3 comprises a heavy chain variable region (HCVR) comprising the amino acid sequence of SEQ ID NO: 14 and a light chain variable region (LCVR) comprising the amino acid sequence of SEQ ID NO: 15.

27. The method of claim 1, wherein the second antigen-binding arm that binds human CD20 comprises a heavy chain variable region (HCVR) comprising the amino acid sequence of SEQ ID NO: 13 and a light chain variable region (LCVR) comprising the amino acid sequence of SEQ ID NO: 15.

28. The method of claim 1, wherein the first antigen-binding arm that binds human CD3 comprises a heavy chain variable region (HCVR) comprising the amino acid sequence of SEQ ID NO: 14 and a light chain variable region (LCVR) comprising the amino acid sequence of SEQ ID NO: 15, and the second antigen-binding arm that binds human CD20 comprises a heavy chain variable region (HCVR) comprising the amino acid sequence of SEQ ID NO: 13 and a light chain variable region (LCVR) comprising the amino acid sequence of SEQ ID NO: 15.

29. The method of claim 1, wherein the therapeutic protein is a bispecific anti-CD3 x anti-CD20 antibody.

30. The method of claim 29, wherein the bispecific anti-CD3 x anti-CD20 antibody comprises a first heavy chain comprising the amino acid sequence of SEQ ID NO: 11 or an amino acid sequence comprising residues 1-448 of SEQ ID NO: 11, and a light chain comprising the amino acid sequence of SEQ ID NO: 12.

31. The method of claim 29, wherein the bispecific anti-CD3 x anti-CD20 antibody comprises a second heavy chain comprising the amino acid sequence of SEQ ID NO: 10 or an amino acid sequence comprising residues 1-452 of SEQ ID NO: 10, and a light chain comprising the amino acid sequence of SEQ ID NO: 12.

32. The method of claim 29, wherein the bispecific anti-CD3 x anti-CD20 antibody comprises a first heavy chain comprising the amino acid sequence of SEQ ID NO: 11 or an amino acid sequence comprising residues 1-448 of SEQ ID NO: 11, a second heavy chain comprising the amino acid sequence of SEQ ID NO: 10 or an amino acid sequence comprising residues 1-452 of SEQ ID NO: 10, and a common light chain comprising the amino acid sequence of SEQ ID NO: 12.

33. The method of claim 2, wherein the F2D3 is administered to the subject from 24 to 96 hours following administration of the F1D3, or F2D3 is administered to the subject from 18 to 72 hours following administration of F1D3.

34. The method of claim 2, wherein the subsequent week is week 4 of the dosing regimen, or the subsequent week is any one of weeks 4 to 36 of the dosing regimen.

35. The method of claim 2, wherein the tertiary dose is 40 mg, 80 mg, 160 mg, or 320 mg.

36. The method of claim 2, wherein the tertiary dose is administered as a single dose in weeks 4 to 12 of the dosing regimen.

37. The method of claim 2, wherein the primary dose (D1) of the therapeutic protein is from 0.5 mg to 1 mg.

38. The method of claim 37, wherein the maximum weekly dose of the therapeutic protein is 40 mg, 80 mg, 160 mg, or 320 mg.

39. The method of claim 38, further comprising administering at least one maintenance dose of the therapeutic protein once every two weeks following one or more doses of the maximum weekly dose.

40. The method of claim 39, wherein the maintenance dose of the therapeutic protein is 160 mg or 320 mg.

41. The method of claim 2, wherein:

(a) the therapeutic protein is administered to the subject in combination with a second agent selected from a steroid, an anti-histamine, acetaminophen, a non-steroidal anti-inflammatory drug (NSAID), an IL-6 antagonist, or an IL-6R antagonist;

(b) the therapeutic protein is administered to the subject in combination with dexamethasone or indomethacin; or (c) the therapeutic protein is administered to the subject in combination with dexamethasone, and the dexamethasone is administered to the subject about one to three hours prior to at least one of the F1D3 and the F2D3.

42. The method of claim 38, wherein the therapeutic protein is administered to the subject in combination with a second therapeutic agent, wherein the second therapeutic agent comprises at least one of rituximab, obinutuzumab, cyclophophamide, doxorubicin, vincristine, prednisone, prednisolone, bendamustine, lenalidomide, chlorambucil, ibritumomab tiuxetan, idelalisib, copanlisib, duvelisib, etoposide, methylprednisolone, cytarabine, cisplatin, mesna, ifosfamide, mitoxantrone, and procarbazine.

43. The method of claim 42, wherein the second therapeutic agent is lenalidomide.

44. The method of claim 38, wherein the therapeutic protein is a bispecific antibody comprising a first heavy chain comprising the amino acid sequence of SEQ ID NO: 11 or an amino acid sequence comprising residues 1-448 of SEQ ID NO: 11, a second heavy chain comprising the amino acid sequence of SEQ ID NO: 10 or an amino acid sequence comprising residues 1-452 of SEQ ID NO: 10, and a common light chain comprising the amino acid sequence of SEQ ID NO: 12.

45. A method of administering a bispecific antibody to a subject in a dosing regimen to mitigate adverse effects of cytokine release syndrome (CRS) or infusion-related reaction (IRR) in the treatment of a CD20-expressing B-cell malignancy, comprising:

administering fractions of a primary dose (D1) of the bispecific antibody in week 1 of the dosing regimen, wherein the primary dose comprises no more than 10 mg of the bispecific antibody, a first dose fraction (F1D1) comprises 25% to 30% of the total primary dose and is administered to the subject on day 1 of week 1, and a second dose fraction (F2D1) comprises the remaining 70% to 75% of the total primary dose and is administered to the subject from 18 to 72 hours following administration of the F1D1;

administering fractions of a secondary dose (D2) of the bispecific antibody in week 2 of the dosing regimen, wherein the secondary dose is greater than the primary dose and no more than one-half of a maximum weekly dose of the bispecific antibody, a first dose fraction (F1D2) comprises 50% of the total secondary dose, a second dose fraction (F2D2) comprises the remaining 50% of the total secondary dose, and the F2D2 is administered to the subject from 18 to 72 hours following administration of the F1D2 during week 2 of the dosing regimen; and administering the maximum weekly dose of the bispecific antibody to the subject as a single dose in a subsequent week of the dosing regimen, wherein the administration of the bispecific antibody to the subject in the dosing regimen reduces the prevalence or severity, or both the prevalence and severity, of CRR or IRR compared to a dosing regimen not including split administration of the primary dose and the secondary dose, and wherein the bispecific antibody comprises a first antigen-binding arm that binds human CD3 and comprises complementarity determining regions HCDR1-

HCDR2-HCDR3-LCDR1-LCDR2-LCDR3 comprising the amino acid sequences, respectively, of SEQ ID NOs: 19-20-21-22-23-24, and a second antigen-binding arm that binds human CD20 and comprises complementarity determining regions HCDR1-HCDR2-HCDR3-LCDR1-LCDR2-LCDR3 comprising the amino acid sequences, respectively, of SEQ ID NOs: 16-17-18-22-23-24.

46. The method of claim 45, wherein the primary dose of the bispecific antibody is 0.5 mg to 1 mg.

47. The method of claim 46, wherein the maximum weekly dose of the bispecific antibody is 80 mg.

48. The method of claim 46, wherein the maximum weekly dose of the bispecific antibody is 160 mg.

49. The method of claim 47, wherein the subsequent week is week 4 of the dosing regimen.

50. The method of claim 48, wherein the subsequent week is week 4 of the dosing regimen.

51. The method of claim 49, wherein the maximum weekly dose is administered weekly for 9 weeks during a weekly phase of the dosing regimen.

52. The method of claim 50, wherein the maximum weekly dose is administered weekly for 9 weeks during a weekly phase of the dosing regimen.

53. The method of claim 51, further comprising administering a maintenance dose of the bispecific antibody once every two weeks during a maintenance phase of the dosing regimen that follows completion of the weekly phase of the dosing regimen.

54. The method of claim 52, further comprising administering a maintenance dose of the bispecific antibody once every two weeks during a maintenance phase of the dosing regimen that follows completion of the weekly phase of the dosing regimen.

55. The method of claim 53, wherein the maintenance dose of the bispecific antibody is 160 mg.

56. The method of claim 54, wherein the maintenance dose of the bispecific antibody is 320 mg.

57. The method of claim 55, wherein the subject has been diagnosed with follicular lymphoma.

58. The method of claim 56, wherein the subject has been diagnosed with diffuse large B-cell lymphoma.

59. The method of claim 45, wherein the first antigen-binding arm of the bispecific antibody comprises a heavy chain variable region (HCVR) comprising the amino acid sequence of SEQ ID NO: 14 and a light chain variable region (LCVR) comprising the amino acid sequence of SEQ ID NO: 15, and the second antigen-binding arm of the bispecific antibody comprises a heavy chain variable region (HCVR) comprising the amino acid sequence of SEQ ID NO: 13 and a light chain variable region (LCVR) comprising the amino acid sequence of SEQ ID NO: 15.

60. The method of claim 59, wherein the bispecific antibody comprises a first heavy chain comprising the amino acid sequence of SEQ ID NO: 11 or an amino acid sequence comprising residues 1-448 of SEQ ID NO: 11, a second heavy chain comprising the amino acid sequence of SEQ ID NO: 10 or an amino acid sequence comprising residues 1-452 of SEQ ID NO: 10, and a common light chain comprising the amino acid sequence of SEQ ID NO: 12.

* * * * *